(12) United States Patent
Messersmith et al.

(10) Patent No.: US 7,858,679 B2
(45) Date of Patent: Dec. 28, 2010

(54) POLYMERIC COMPOSITIONS AND RELATED METHODS OF USE

(75) Inventors: Phillip B. Messersmith, Clarendon Hills, IL (US); Xiaowu Fan, Evanston, IL (US); Lijun Lin, Stafford, TX (US)

(73) Assignee: Northwestern University, Evanston, IL (US)

( * ) Notice: Subject to any disclaimer, the term of this patent is extended or adjusted under 35 U.S.C. 154(b) by 515 days.

(21) Appl. No.: 11/179,218

(22) Filed: Jul. 11, 2005

(65) Prior Publication Data

US 2006/0009550 A1 Jan. 12, 2006

Related U.S. Application Data

(63) Continuation-in-part of application No. 11/068,298, filed on Feb. 28, 2005, which is a continuation-in-part of application No. 10/199,960, filed on Jul. 19, 2002, now abandoned.

(60) Provisional application No. 60/586,742, filed on Jul. 9, 2004, provisional application No. 60/306,750, filed on Jul. 20, 2001, provisional application No. 60/373,919, filed on Apr. 19, 2002, provisional application No. 60/549,259, filed on Mar. 2, 2004, provisional application No. 60/548,314, filed on Feb. 27, 2004.

(51) Int. Cl.
| | |
|---|---|
| *C08L 89/00* | (2006.01) |
| *D21H 19/50* | (2006.01) |
| *A61K 38/00* | (2006.01) |
| *A01N 37/18* | (2006.01) |
| *A61M 36/14* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. ............................ 524/17; 514/2; 530/300; 424/1.69

(58) Field of Classification Search ....................... 514/2
See application file for complete search history.

(56) References Cited

U.S. PATENT DOCUMENTS

| | | |
|---|---|---|
| 4,339,561 A | 7/1982 | Jacquet et al. |
| 4,496,397 A | 1/1985 | Waite |
| 4,585,585 A | 4/1986 | Waite |
| 4,615,697 A | 10/1986 | Robinson |
| 4,687,740 A | 8/1987 | Waite |
| 4,795,436 A | 1/1989 | Robinson |
| 4,808,702 A | 2/1989 | Waite |
| 4,908,404 A * | 3/1990 | Benedict et al. .......... 525/54.11 |
| 4,978,336 A | 12/1990 | Capozzi et al. |
| 4,983,392 A | 1/1991 | Robinson |
| 5,015,677 A | 5/1991 | Benedict et al. |
| 5,024,933 A | 6/1991 | Yang et al. |
| 5,030,230 A | 7/1991 | White |
| 5,049,504 A | 9/1991 | Maugh et al. |
| 5,098,999 A | 3/1992 | Yamamoto et al. |
| 5,108,923 A | 4/1992 | Benedict et al. |
| 5,116,315 A | 5/1992 | Capozzi et al. |
| 5,156,956 A | 10/1992 | Motoki et al. |
| 5,192,316 A | 3/1993 | Ting |
| 5,197,973 A | 3/1993 | Pang et al. |
| 5,202,236 A | 4/1993 | Maugh et al. |
| 5,202,256 A | 4/1993 | Maugh et al. |
| 5,225,196 A | 7/1993 | Robinson |
| 5,242,808 A | 9/1993 | Maugh et al. |
| 5,260,194 A | 11/1993 | Olson |
| 5,374,431 A | 12/1994 | Pang et al. |
| 5,410,023 A | 4/1995 | Burzio |
| 5,428,014 A | 6/1995 | Labroo et al. |
| 5,487,739 A | 1/1996 | Aebischer et al. |
| 5,490,980 A | 2/1996 | Richardson et al. |
| 5,520,727 A | 5/1996 | Vreeland et al. |
| 5,525,336 A | 6/1996 | Green et al. |
| 5,549,904 A | 8/1996 | Juergensen et al. |
| 5,563,047 A | 10/1996 | Petersen |
| 5,574,134 A | 11/1996 | Waite |
| 5,580,697 A | 12/1996 | Keana et al. |
| 5,582,955 A | 12/1996 | Keana et al. |
| 5,605,938 A | 2/1997 | Roufa et al. |
| 5,618,551 A | 4/1997 | Tardy et al. |
| 5,628,793 A | 5/1997 | Zirm |

(Continued)

FOREIGN PATENT DOCUMENTS

| | | |
|---|---|---|
| DE | 196 43 007 A 1 | 4/1998 |
| WO | WO 88/03953 | 6/1988 |
| WO | WO 92/10567 | 6/1992 |
| WO | WO 94/28937 | 12/1994 |
| WO | 9640090 | 12/1996 |

(Continued)

OTHER PUBLICATIONS

Pyun, J., et al. Synthesis of Polymer Brushes Using Atom Transfer Radical Polymerization. MACROMOL. Rapid Commun. 2003, vol. 24, pp. 1043-1059. Entire document, especially p. 1044-1045, 1055.
Gu B and Sen, A. Synthesis of Aluminum Oxide/Gradient Copolymer Composites by Atom Transfer Radical Polymerization. Macromolecules 2002, vol. 35, pp. 8913-8916, especially p. 8913.
Dalsin J. L., et al. Mussel Adhesive Protein Mimetic Polymers for the Preparation of Nonfouling Surfaces. J. Am. Chem. Soc. 2003, vol. 125, pp. 4253-4258, entire document, especially pp. 4253-4254 and 4257-4258.

(Continued)

*Primary Examiner*—Maury Audet
(74) *Attorney, Agent, or Firm*—Quarles & Brady, LLP

(57) ABSTRACT

Methods for surface-initiated atom transfer radical polymerization, which can utilize a catecholic alkyl halide initiator.

11 Claims, 35 Drawing Sheets

U.S. PATENT DOCUMENTS

| | | | |
|---|---|---|---|
| 5,705,177 | A | 1/1998 | Roufa et al. |
| 5,705,178 | A | 1/1998 | Roufa et al. |
| 5,736,132 | A | 4/1998 | Juergensen et al. |
| 5,776,747 | A | 7/1998 | Schinstine et al. |
| 5,800,828 | A | 9/1998 | Dionne et al. |
| 5,817,470 | A | 10/1998 | Burzio et al. |
| 5,830,539 | A | 11/1998 | Yan et al. |
| 5,834,232 | A | 11/1998 | Bishop et al. |
| 5,858,747 | A | 1/1999 | Schinstine et al. |
| 5,935,849 | A | 8/1999 | Schinstine et al. |
| 5,939,385 | A | 8/1999 | Labroo et al. |
| 5,955,096 | A | 9/1999 | Santos et al. |
| 5,968,568 | A | 10/1999 | Kuraishi et al. |
| 5,985,312 | A | 11/1999 | Jacob et al. |
| 5,994,325 | A | 11/1999 | Roufa et al. |
| 6,010,871 | A | 1/2000 | Takahara et al. |
| 6,020,326 | A | 2/2000 | Roufa et al. |
| 6,022,597 | A | 2/2000 | Yan et al. |
| 6,083,930 | A | 7/2000 | Roufa et al. |
| 6,093,686 | A | 7/2000 | Nakada et al. |
| 6,129,761 | A | 10/2000 | Hubbell |
| 6,150,461 | A | 11/2000 | Takei et al. |
| 6,156,348 | A | 12/2000 | Santos et al. |
| 6,162,903 | A | 12/2000 | Trowern et al. |
| 6,235,313 | B1 | 5/2001 | Mathiowitz et al. |
| 6,267,957 | B1 | 7/2001 | Green et al. |
| 6,284,267 | B1 * | 9/2001 | Aneja ............ 424/450 |
| 6,294,187 | B1 | 9/2001 | Boyce et al. |
| 6,306,993 | B1 | 10/2001 | Rothbard et al. |
| 6,309,669 | B1 | 10/2001 | Setterstrom et al. |
| 6,322,996 | B1 | 11/2001 | Sato et al. |
| 6,325,951 | B1 | 12/2001 | Soper et al. |
| 6,331,422 | B1 | 12/2001 | Hubbell et al. |
| 6,335,430 | B1 | 1/2002 | Qvist |
| 6,365,187 | B2 | 4/2002 | Mathiowitz et al. |
| 6,368,586 | B1 | 4/2002 | Jacob et al. |
| 6,417,173 | B1 | 7/2002 | Roufa et al. |
| 6,486,213 | B1 | 11/2002 | Chen et al. |
| 6,491,903 | B1 | 12/2002 | Forster et al. |
| 6,497,729 | B1 | 12/2002 | Moussy et al. |
| 6,506,577 | B1 | 1/2003 | Deming et al. |
| 6,555,103 | B2 | 4/2003 | Leukel et al. |
| 6,565,960 | B2 | 5/2003 | Koob et al. |
| 6,566,074 | B1 | 5/2003 | Goetinck |
| 6,566,406 | B1 | 5/2003 | Pathak et al. |
| 6,635,274 | B1 | 10/2003 | Masiz et al. |
| 6,663,883 | B1 | 12/2003 | Akiyama et al. |
| 6,821,530 | B2 | 11/2004 | Koob et al. |
| 6,887,845 | B2 | 5/2005 | Barron et al. |
| 7,009,034 | B2 | 3/2006 | Pathak et al. |
| 7,208,171 | B2 | 4/2007 | Messersmith et al. |
| 7,300,991 | B2 | 11/2007 | Nishimura et al. |
| 2001/0043940 | A1 | 11/2001 | Boyce et al. |
| 2001/0049400 | A1 | 12/2001 | Alli et al. |
| 2002/0022013 | A1 | 2/2002 | Leukel et al. |
| 2002/0049290 | A1 | 4/2002 | Vanderbilt |
| 2002/0182633 | A1 | 12/2002 | Chen et al. |
| 2003/0009235 | A1 | 1/2003 | Manrique et al. |
| 2003/0012734 | A1 | 1/2003 | Pathak et al. |
| 2003/0039676 | A1 | 2/2003 | Boyce et al. |
| 2003/0065060 | A1 | 4/2003 | Qvist et al. |
| 2003/0069205 | A1 | 4/2003 | Roufa et al. |
| 2003/0087338 | A1 | 5/2003 | Messersmith et al. |
| 2003/0099682 | A1 | 5/2003 | Moussy et al. |
| 2003/0109587 | A1 | 6/2003 | Mori |
| 2003/0208888 | A1 | 11/2003 | Fearing et al. |
| 2004/0005421 | A1 | 1/2004 | Gervase et al. |
| 2004/0028646 | A1 | 2/2004 | Gross et al. |
| 2005/0032929 | A1 | 2/2005 | Greener |
| 2005/0288398 | A1 | 12/2005 | Messersmith et al. |
| 2006/0009550 | A1 | 1/2006 | Messersmith et al. |

FOREIGN PATENT DOCUMENTS

| | | |
|---|---|---|
| WO | WO 97/34016 | 9/1997 |
| WO | WO 98/07076 | 2/1998 |
| WO | 9950394 | 10/1999 |
| WO | WO 01/44401 A1 | 6/2001 |
| WO | WO 02/34764 A1 | 5/2002 |
| WO | WO 03/008376 A2 | 1/2003 |
| WO | WO 03/080137 A1 | 10/2003 |
| WO | WO 2004/042068 A2 | 5/2004 |

OTHER PUBLICATIONS

Rajh T. et al., Surface Restructuring of Nanoparticles: An Efficient Route for Ligand-Metal Oxide Crosstalk. J. J. Phys. Chem. B 2002, vol. 106, pp. 10543-10552. especially pp. 10543, 10546 and 10550.

Advincula, "Surface Initiated Polymerization from Nanoparticle Surfaces," *J. Dispersion Sci. Technol.*, vol. 24, Nos. 3 & 4 (2003), pp. 343-361.

Ahmed, et al., "Synthesis and Application of Fluorescein-Labeled Pluronic Block Copolymers to the Study of Polymer-Surface Interactions," *Langmuir*, vol. 17, No. 2 (2001), pp. 537-546.

Alexandridis, P.; Nivaggioli, T.; Hatton, T. A., "Temperature Effects on Structural Properties of Pluronic P104 and F108 PEO-PPO-PEO Block Copolymer Solutions," *Langmuir*, vol. 11, No. 5 (1995), pp. 1468-1476.

Alexandridis, P., "Poly(ethylene oxide)-Poly(propylene oxide) Block Copolymer Surfactants," *Curr. Opin. Colloid Interface Sci.*, vol. 2, No. 5 (1997), pp. 478-489.

Alivisatos, P., "The use of nanocrystals in biological detection," *Nature Biotechnology*, vol. 22, No. 1 (2004), pp. 47-52.

Alleyne, Jr., et al., "Efficacy and biocompatibility of a photopolymerized, synthetic, absorbable hydrogel as a dural sealant in a canine craniotomy model," *J. Neurosurg.*, vol. 88 (1998), pp. 308-313.

Andreopoulos, et al., "Light-induced tailoring of PEG-hydrogel properties," *Biomaterials*, vol. 19 (1998), pp. 1343-1352.

Andrzejewska, et al., "The role of oxygen in camphorquinone-initiated photopolymerization," *Macromol. Chem. Phys.*, vol. 199 (1998), pp. 441-449.

Araujo, et al., "Interaction of Catechol and Gallic Acid with Titanium Dioxide in Aqueous Suspensions. 1. Equilibrium Studies," *Langmuir*, vol. 21 (2005), pp. 3470-3474.

Armstrong et al., "Scanning Microcalorimetric Investigations of Phase Transitions in Dilute Aqueous Solutions of Poly(oxypropylene)," *J. Phys. Chem.*, vol. 99 (1995), pp. 4590-4598.

Arnow, "Colorimetric Determination of the Component of 3, 4-Dihydroxyphemylalanine-Tyrosine Mixtures," *J. Biol. Chem.*, vol. 118 (1937), pp. 531-538.

Arzt et al., "From micro to nano contacts in biological attachment devices," *Proc. Nat. Acad. Sci. USA*, vol. 100 (2003), pp. 10603-10606.

Arzt, "Biological and artificial attachment devices: Lessons for materials scientists from flies and geckos," *Mater. Sci. Eng. C*, vol. 26 (2006), pp. 1245-1250.

Autumn et al., "Adhesive force of a single gecko foot-hair," *Nature*, vol. 405 (2000), pp. 681-685.

Autumn et al., "Evidence for van der Waals adhesion in gecko setae," *Proc. Nat. Acad. Sci. USA*, vol. 99 (2002), pp. 12252-12256.

Baird, et al. (2007), "Reduction of Incisional Cerebrospinal Fluid Leak Following Posterior Foss Surgery with the use of Duraseal," American Association of Neurosurgeons. Abstract retrieved Jul. 23, 2008, from AANS Abstract Center database. Available from: http://www.aans.org/library/article.aspx?ArticleId=42392.

Balsa-Canto, et al., "Reduced-Order Models for Nonlinear Distributed Process Systems and Their Application in Dynamic Optimization," *Ind. Eng. Chem. Res.*, vol. 43 (2004), pp. 3353-3363.

Banerjee, et al., "Derivatives of 3, 4-Dihydroxyphenylalanine for Peptide Synthesis," *J. Org. Chem.*, vol. 41, No. 18 (1976), pp. 3056-3058.

Barbakadze, et al., "Poly[3-(3, 4-dihydroxyphenyl)glyceric Acid], A New Biologically Active Polymer from *Symphytum Asperum Lepech.* and *S. Caucasicum Bieb.* (Boraginaceae)," *Molecules*, vol. 10 (2005), pp. 1135-1144.

Barichello et al., "Absorption of insulin from Pluronic F-127 gels following subcutaneous administration in rats," *Int. J. Pharm.*, vol. 184 (1999), pp. 189-198.

Benedek, "End Uses of Pressure-Sensitive Products" in *Developments in Pressure-Sensitive Products*, Benedek (ed.), CRC Press: Boca Raton, FL (2006). pp. 539-596.

Bharathi, et al., "Direct synthesis of gold nanodispersions in sol-gel derived silicate sols, gels and films," *Chem. Commun.* (1997), pp. 2303-2304.

Bontempo, et al., "Atom Transfer Radical Polymerization as a Tool for Surface Functionalization," *Adv. Mater.*, vol. 14, No. 17 (2002), pp. 1239-1241.

Boogaarts, et al., "Use of a novel absorbable hydrogel for augmentation of dural repair: results of a preliminary clinical study," *Neurosurg.*, vol. 57 (2005), pp. 146-151.

Bromberg, "Novel Family of Thermogelling Materials via C—C Bonding between Poly(acrylic acid) and Poly(ethylene oxide)-*b*-poly(propylene oxide)-*b*-poly(ethylene oxide)," *J. Phys. Chem. B*, vol. 102 (1998), pp. 1956-1963.

Bromberg, "Self-Assembly in Aqueous Solutions of Polyether-Modified Poly(acrylic acid)," *Langmuir*, vol. 14 (1998), pp. 5806-5812.

Bromberg, "Temperature-responsive gels and thermogelling polymer matrices for protein and peptide delivery," *Advanced Drug Reviews*, vol. 31 (1998), pp. 197-221.

Brown, et al., "Micelle and Gel Formation in a Poly(ethylene oxide)/Poly(propylene oxide)/Poly(ethylene oxide) Triblock Copolymer in Water Solution. Dynamic and Static Light Scattering and Oscillatory Shear Measurements," *J. Phys. Chem.*, vol. 95 (1991), pp. 1850-1858.

Bruinsma, et al., "Bacterial adhesion to surface hydrophilic and hydrophobic contact lenses," *Biomaterials*, vol. 22 (2001), pp. 3217-3224.

Bryant, et al., "Cytocompatibility of UV and visible light photoinitiating systems on cultured NIH/3T3 fobroblasts in vitro," *J. Biomater. Sci. Polymer Edn*, vol. 11, No. 5 (2000), pp. 439-457.

Burdick, et al., "Synthesis and Characterization of Tetrafunctional Lactic Acid Oligomers: A potential In Situ Forming Degradable Orthopaedic Biomaterial," *J. Polym. Sci., Part A: Polym. Chem.*, vol. 39 (2001), pp. 683-692.

Burzio, et al., "Cross-Linking in Adhesive Quinoproteins: Studies with Model Decapeptides," *Biochemistry*, vol. 39 (2000), pp. 11147-11153.

Cabana, et al., "Study of the Gelation Process of Polyethylene Oxide$_a$—Polypropylene Oxide$_b$—Polyethylene Oxide$_a$ Copolymer (Poloxamer 407) Aqueous Solutions," *J. Colloid Interface Sci.*, vol. 190 (1997), pp. 307-312.

Campbell, et al., "Evaluation of Absorbable Surgical Sealants: In vitro Testing," Confluent Surgical, Inc. (2005) White Paper. Available from: http://www.confluentsurgical.com/pdf/ds/6070_DuraSeal_Invitro_WP13-25.pdf.

Carmichael, et al., "Selective Electroless Metal Deposition Using Microcontact Printing of Phosphine—Phosophonic Acid Inks," *Langmuir*, vol. 20 (2004), pp. 5593-5598.

Chalykh, et al., "Pressure-Sensitive Adhestion in the Blends of Poly(N-vinyl pyrrolidone) and Poly(ethylene glycol) of Disparate Chain Lengths," *J. of Adhes.*, vol. 78 (2002), pp. 667-694.

Chehimi, et al., "XPS investigations of acid-base interactions in adhesion. Part 3. Evidence for orientation of carbonyl groups from poly(methylmethacrylate) (PMMA) at the PMMA—glass and PMMA—$SiO_2$ interfaces," *J. Electron. Spectrosc. Relat. Phenom.*, vol. 63 (1993), pp. 393-407.

Chen, et al., "Temperature-Induced Gelation Pluronic-g-Poly(acrylic acid) Graft Copolymers for Prolonged Drug Delivery to the Eye," in Harris, et al. (eds.) *Poly(ethylene glycol): Chemistry and Biological Applications*. New York, NY: Oxford University Press USA, 1997. pp. 441-451.

Chen, et al., "Enzymatic Methods for in Situ Cell Entrapment and Cell Release," *Biomacromolecules*, vol. 4 (2003), pp. 1558-1563.

Collier, et al., "Enzymatic Modification of Self-Assembled Peptide Structures with Tissue Transglutaminase," *Bioconjugate Chem.*, vol. 14 (2003), pp. 748-755.

Collier, et al., "Self-Assembling Polymer-Peptide Conjugates: Nanostructural Tailoring," *Adv. Mater.*, vol. 16, No. 11 (2004), pp. 907-910.

Collins, et al., "Use of collagen film as a dural substitute: Preliminary animal studies," *J. Biomed. Mater. Res.*, vol. 25 (1991), pp. 267-276.

Connor, et al., "New Sol—Gel Attenuated Total Reflection Infrared Spectroscopic Method for Analysis of Adsorption at Metal Oxide Surfaces in Aqueous Solutions. Chelation of $TiO_2$, $ZrO_2$, and $Al_2O_3$ Surfaces by Catechol, 8-Quinolinol, and Acetylacetone," *Langmuir*, vol. 11 (1995), pp. 4193-4195.

Cosgrove, et al., "Safety and efficacy of a novel polyethylene glycol hydrogel sealant for watertight dural repair," *J. Neurosurg.*, vol. 106 (2007), pp. 52-58.

Cosgrove, "Safety and Efficacy of a Novel PEG Hydrogel Sealant (DuraSeal®) for Watertight Closure after Dural Repair," Presented at the Congress of Neurological Surgeons 55th Annual Meeting, Boston, MA, Oct. 2005. Available from: http://www.confluentsurgical.com/pdf/ds/CosgroveAbstractCNS2005.pdf.

Crescenzi, et al., "New Gelatin-Based Hydrogels via Enzymatic Networking," *Biomacromolecules*, vol. 3 (2002), pp. 1384-1391.

Creton, "Pressure-Sensitive Adhesives: An Introductory Course," *MRS Bulletin*, vol. 26, No. 6 (2003), pp. 434-439.

Crosby, et al., "Rheological properties and adhesive failure of thin viscoelastic layers," *J. Rheol.*, vol. 46, No. 1 (2002), pp. 273-294.

Crosby, et al., "Controlling Polymer Adhesion with "Pancakes"," *Langmuir*, vol. 21 (2005), pp. 11738-11743.

Cruise, et al., "A Sensitivity Study of the Key Parameters in the Interfacial Photopolymerization of Poly(etheylene glycol) Dlacrylate upon Porcine Islets," *Biotechnol. Bioeng.*, vol. 57, Issue 6 (1998), pp. 655-665.

Dai, et al., "Novel pH-Responsive Amphiphilic Diblock Copolymers with Reversible Micellization Properties," *Langmuir* 19 (2003). pp. 5175-5177.

Dalsin, et al., "Surface Modification for Protein Resistance Using a Biomimetic Approach," *Mat. Res. Soc. Symp. Proc.*, vol. 774 (2002), pp. 75-80.

Dalsin, et al., "Antifouling Performance of Poly(ethylene glycol) Anchored onto Surfaces by Mussel Adhesive Protein Mimetic Peptides," *Polymeric Materials Science and Engineering* 90 (2004). pp. 247-248.

Dalsin, et al., "Protein Resistance of Titanium Oxide Surfaces Modified by Biologically Inspired mPEG—DOPA," *Langmuir* 21 (2005). pp. 640-646.

Davis, et al., "Polymeric microspheres as drug carriers," *Biomaterials* 9 (1), 1988. pp. 111-115.

Deible, et al., "Creating molecular barriers to acute platelet deposition on damaged arteries with reactive polyethylene glycol," *J. Biomed. Maters. Res.* 41 (1998). pp. 251-256.

Deming, "Mussel byssus and biomolecular materials," *Current Opinion in Chemical Biology*, 3 (1), 1999. pp. 100-105.

Deming, et al., "Mechanistic Studies of Adhesion and Crosslinking in Marine Adhesive Protein Analogs," *Polym. Mater. Sci. Eng.*, 80 (1999). pp. 471-472.

Deruelle, et al., "Adhesion at the Solid—Elastomer Interface: Influence of the Interfacial Chains," *Macromolecules*, vol. 28 (1995), pp. 7419-7428.

Desai, et al., "In Vitro Evaluation of Pluronic F127-Based Controlled-Release Ocular Delivery Systems for Polocarpine," *J. Phar. Sci.*, 87 (2), 1998. pp. 226-230.

Dillow, et al., "Adhesion of $\alpha_5\beta_1$ receptors to biomimetic substrates constructed from peptide amphiphiles," *Biomaterials*, vol. 22 (2001), pp. 1493-1505.

Donkerwolcke, et al., "Tissue and bone adhesives—historical aspects," *Biomaterials* 19 (1998). pp. 1461-1466.

Dossot, et al., "Role of Phenolic Derivatives in Photopolymerization of an Acrylate Coating," *J. Appl. Polymer. Sci.*, 78 (2000). pp. 2061-2074.

Drumheller, et al., "Polymer Networks with Grafted Cell Adhesion Peptides for Highly Biospecific Cell Adhesive Substrates," *Anal. Biochem.*, vol. 222 (1994), pp. 380-388.

Elbert, et al., "Reduction of fibrous adhesion formation by a copolymer possessing an affinity for anionic surfaces," *J. Biomed. Mater. Res.*, vol. 42, Issue 1 (1998), pp. 55-65.

Elisseeff, et al., "Photoencapsulation of chondrocytes in poly(ethylene oxide)-based semi-interpenetrating networks," *J. Biomed. Mater. Res.*, vol. 51, Issue 2 (2000), pp. 164-171.

Erli, et al., "Surface pretreatments for medical application of adhesion," *BioMed. Eng. Online*, 2 (15), 2003. Available from: http://www.biomedical-engineering-online.com/content/2/2/15.

Fan et al., "Surface-Initiated Polymerization from $TiO_2$ Nanoparticle Surfaces through a Biomimetic Initiator: A New Route toward Polymer-Matrix Composites," *Comp. Sci. Tech.*, 66 (9), 2006. pp. 1195-1201.

Fang, et al., "Effect of Molecular Structure on the Adsorption of Protein on Surfaces with Grafted Polymers," *Langmuir*, vol. 18 (2002), pp. 5497-5510.

Faulkner, et al., "A New Stable Pluronic F68 Gel Carrier for Antibiotics in Contaminated Wound Treatment," *Am. J. Emerg. Med.*, 15 (1), 1997. pp. 20-24.

Feldstein, et al., "Molecular Design of Hydrophilic Pressure-Sensitive Adhesives for Medical Applications," in *Developments in Pressure-Sensitive Products*, I. Benedek (ed.). 2006, CRC Press: Boca Raton, FL. pp. 473-503.

Filpula, et al., "Structural and Functional Repetition in a Marine Mussel Adhesive Protein," *Biotechnol. Prog.* 6 (1990). pp. 171-177.

Fischer, et al., "In vitro cytotoxicity testing of polycations: influence of polymer structure on cell viability and hemolysis," *Biomaterials* 24 (2003). pp. 1121-1131.

Flanigan, et al., "Adhesive and Elastic Properties of Thin Gel Layers," *Langmuir*, vol. 15 (1999), pp. 4966-4974.

Flanigan, et al., "Structural Development and Adhesion of Acrylic ABA Triblock Copolymer Gels," *Macromolecules*, vol. 32 (1999), pp. 7251-7262.

Flood, et al., "Efficient Asymmetric Epoxidation of $\alpha,\beta$-Unstarudated Ketones Using a Soluble Triblock Polyethylene Glycol-Polyamino Acid Catalyst," *Org. Lett.*, vol. 3, No. 5 (2001), pp. 683-686.

Floudas, et al., "Hierarchical Self-Assembly of Poly($\gamma$-benzyl-L-glutamate)—Poly(ethylene glycol)—Poly($\gamma$-benzyl-L-glutamate) Rod—Coil—Rod Triblock Copolymers," *Macromolecules*, vol. 36 (2003), pp. 3673-3683.

Flory, et al., "Effect of Volume Exclusion on the Dimensions of Polymer Chains," *J. Chem. Phys.*, vol. 44, No. 6 (1966), pp. 2243-2248.

Floyd-Smith, et al., "Interferon Action: RNA Cleavage Pattern of a (2'-5')Oligoadenylate-Dependent Endonuclease," *Science*, vol. 212, No. 4498 (May 29, 1981), pp. 1030-1032.

Frank, et al., "Adhesion of *Mytilus edulis* Foot Protein 1 on Silica: Ionic Effects on Biofouling," *Biotechnol. Prog.* 18 (2002). pp. 580-586.

Fuchsbauer, et al., "Influence of gelatin matrices cross-linked with transglutaminase on the properties of an enclosed bioactive material using $\beta$-galactosidase as model system," *Biomaterials* 17 (1996). pp. 1481-1488.

Fujisawa, et al., "Kinetic Evaluations of the Reactivity of Flavonoids as Radical Scavengers," *SAR QSAR Environ. Res.*, Vo. 13, No. 6 (2002), pp. 617-627.

Fuller, et al., "A Procedure for the Facile Synthesis of Amino-Acid N-Carboxyanhydrides," *Biopolymers* 15 (1976). pp. 1869-1871.

Fuller, et al., "DOPA-Containing Polypeptides. I. Improved Synthesis of High-Molecular—Weight Poly (L-DOPA) and Water-Soluble Copolypeptides," *Biopolymers* 17 (1978). pp. 2939-2943.

Geim, et al., "Microfabricated adhesive mimicking gecko foot-hair," *Nat. Materials* 2 (2003). pp. 461-463.

Ghosh, et al., "N,N'-Disuccinimidyl Carbonate: A Useful Reagent for Akoxycarbonylation of Amines," *Tetra. Lett.* 33 (20), 1992. pp. 2781-2784.

Gidanian, et al., "Redox behavior of melanins: direct electrochemistry of dihydroxyindole-melanin and its Cu and Zn adducts," *J. Inorg. Biochem.* 89 (2002). pp. 54-60.

Green, et al., "A surface plasmon resonance study of albumin adssoption to PEO-PPO-PEO triblock copolymers," *J. Biomed. Res.* 42 (1998). p. 165-171.

Gross, et al., "Amine Bindindg Sites in Acyl Intermediates of Transglutaminases," *J. Biol. Chem.* 242 (11) (1977). pp. 3752-3759.

Grotenhuis, et al,. "Synthetic Dural Sealant for Prevention of Postoperative CSF Leakage," Presented at the American Association of Neurological Surgeons; Apr. 2003, San Diego, CA. Available from: http://www.confluentsurgical.com/pdf/ds/AbstractGrotenhuisAbstract.pdf.

Grotenhuis, et al., "A Novel Absorbable Hydrogel for Dural Repair: Results of a Pilot Clinical Study," Confluent Surgical, Inc. (2005) White Paper. Available from: http://www.confluentsurgical.com/pdf/ds/DuraSeal_Pilot_Study_WP4-7-05.pdf.

Grotenhuis, "Costs of postoperative cerebrospinal fluid leakage: 1-year, retrospective analysis of 412 consecutive nontrauma cases," *Surg. Neurol.*, vol. 64, No. 6 (2005), pp. 493-494.

Gu, et al., "The role of microbial biofilms in deterioration of space station candidate materials," *Int. Biodeterioration Biodegradation* 41 (1998). pp. 25-33.

Guvendiren, et al., "Adhesion in Self-Assembled Hydrogels with High DOPA Content," *Proceedings of the 30th Annual Meeting of the Adhesion Society* (2007).

Guvendiren, et al., "Synthesis and Adhesion Properties of DOPA Incorporated Acrylic Triblock Hydrogels," *Proceedings of the 29th Annual Meeting of the Adhesion Society* (2006). pp. 277-279.

Haemers, et al., "Effect of Oxidation Rate on Cross-Linking of Mussel Adhesive Proteins," *Biomacromolecules*, vol. 4 (2003), pp. 632-640.

Hajjaji, et al., "Effect of N-Alkybetaines on the Corrosion of Iron in 1 M HCI Soluction," *Corrosion*, vol. 49, No. 4 (1993), pp. 326-334.

Hanawa, et al., "XPS Characterization of the Surface Oxide Film of 316L Stainless Steel Samples that were Located in Quasi-Biological Environments," *Mater. Trans., JIM*, vol. 43, No. 12 (2002), pp. 3088-3092.

Hansen, et al., "Enzymatic Tempering of a Mussel Adhesive Protein Film," *Langmuir* 14 (1998). pp. 1139-1147.

Harris, "Laboratory Synthesis of Polyethylene Glycol Derivatives," *JMS—Rev. Macromol. Chem. Phys.*, vol. C25, No. 3 (1985), pp. 325-373.

Harris (ed.), "Introduction to Biotechnical and Biomedical Applications of Poly(Ethylene Glycol)" in *Poly(Ethylene Glycol) Chemistry: Biotechnical and Biomedical Applications*, Plenum Press: New York, 1992. pp. 1-14.

Hennink, et al., "Novel crosslinking methods to design hydrogels," *Adv. Drug Deliver. Rev.*, vol. 54 (2002), pp. 13-36.

Hern, et al., "Incorporation of adhesion peptides into nonadhesive hydrogels useful for tissue resurfacing," *J. Biomed. Mater. Res.*, vol. 39, Issue 2 (1998), pp. 266-276.

Hillery, et al., "The effect of adsorbed poloxamer 188 and 407 surfactants on the intestinal uptake of 60-nm polystyrene particles after oral administratin in the rat," *Int. J. Pharm.* 132 (1996). pp. 123-130.

Ho, et al., "Nanoseparated Polymeric Networks with Multiple Antimicrobial Properties," *Adv. Mater.* 16 (12), 2004. pp. 957-961.

Hoffman, "Hydrogels for biomedical applications," *Adv. Drug Deliver. Rev.*, vol. 43 (2002), pp. 3-12.

Hohenadl, et al., "Two Adjacent N-terminal Glutamines of BM-40 (Osteonectin, SPARC) Act as Amine Acceptor Sites in Transglutaminase$_c$-catalyzed Modification," *J. Biol. Chem.* 270 (40), 1995. pp. 23415-23420.

Hrkach, et al., "Synthesis of Poly(L-lactic acid-*co*-L-lysine) Graft Copolymers," *Macromolecules*, vol. 28 (1995), pp. 4736-4739.

Hu, et al., "Protection of 3,4-dihydroxyphenylalanine (DOPA) for Fmoc solid-phase peptide synthesis," *Tetra. Lett.* 41 (2000). pp. 5795-5798.

Hu, et al., "Rational Design of Transglutaminase Substrate Peptides for Rapid Enzymatic Formation of Hydrogels," *J. Am. Chem. Soc.*, vol. 125, (2003), pp. 14298-14299.

Huang, et al., "Synthesis and Characterization of Self-Assembling Block Copolymers Containing Adhesive Moieties," *Polym. Prepr.* 42 (2), 2001. pp. 147-148.

Huang, et al., "Synthesis and Characterization of Self-Assembling Block Copolymers Containing Bioadhesive End Groups," *Biomacromolecules* 3 (2002). pp. 397-406.

Huang, et al., "Covalent Attachment of Novel Poly(ethylene glycol)—Poly(DL-lactic acid) Copolymeric Micelles to TiO₂ Surfaces," *Langmuir* 18 (2002). pp. 252-258.

Huang, et al., "Functionalization of Surfaces by Water-Accelerated Atom-Transfer Radical Polymerization of Hydroxyethyl Methacrylate and Subsequent Derivatization," *Macromolecules* 35 (2002). pp. 1175-1179.

Huang, et al., "Poly(L-lysine)-g-poly(ethylene glycol) Layers on Metal Oxide Surfaces: Surface-Analytical Characterization and Resistance to Serum and Fibrinogen Adsorption," *Langmuir*, vol. 17 (2001), pp. 489-498.

Huang, "Molecular aspects of muco- and bioadhesion: Tethered structures and site-specific surfaces," *J. Controlled Release*, vol. 65 (2000), pp. 63-71.

Huber, et al., "Resolving the nanoscale adhesion of individual gecko spatulae by atomic force microscopy," *Biol. Lett.* 1 (2005). pp. 2-4.

Huber, et al., "Evidence for capillarity contributions to gecko adhesion from single spatula nanomechanical measurements," *Proc. Nat. Acad. Sci. USA*, 102 (45), 2005. pp. 16293-16296.

Huin-Amargier, et al., "New physically and chemically crosslinked hyaluronate (HA)-based hydrogels for cartilage repair," *J. Biomed. Mater. Res.* 76A (2), 2006. pp. 416-424.

Hunter, "Molecular hurdles in polyfectin design and mechanistic background to polycation inducted cytotoxicity," *Adv. Drug Deliver. Rev.*, vol. 58 (2006). pp. 1523-1531.

Hutter, et al., "Calibration of atomic-force microscope tips," *Rev. Sci. Instrum.* 64 (7), Jul. 1993. pp. 1868-1873.

Hvidt, et al., "Micellization and Gelation of Aqueous Solutions of a Triblock Copolymer Studied by Rheological Techniques and Scanning Calorimetry," *J. Phys. Chem.* 98 (1994). pp. 12320-12328.

Hwang, et al., "Expression of Functional Recombinant Mussel Adhesive Protein Mgfp-5 in *Escherichia coli*," *Appl. Environ. Microbiol.* 70 (6), 2004. pp. 3352-3359.

Ikada, "Tissue Adhesives," in *Wound Closure Biomaterials and Devices*, Chu, et al. (eds.), CRC Press, Inc.: Boca Raton, FL, 1997. pp. 317-346.

International Search Report for PCT/US2003/034633; WO 2004/042068 A3 (May 21, 2005); Northwestern University (Applicant); Messersmith, et al. (inventors).

International Search Report for PCT/US2005/006418; WO 2005/118831 A3 (Dec. 15, 2005); Northwestern University (Applicant); Messersmith, et al. (inventors).

International Search Report for PCT/US2005/024642; WO 2006/091226 A3 (Aug. 31, 2006); Northwestern University (Applicant); Messersmith, et al. (inventors).

International Search Report for PCT/US/2005/041280; WO 2006/055531 A3 (May 26, 2006); Northwestern University (Applicant); Messersmith, et al. (Inventors).

International Search Report for PCT/US2007/075299; WO 2008/019352 A3 (Feb. 14, 2008); Nerites Corporation (Applicant); Lee (Inventor).

International Search Report for PCT/US2002/23005; WO 03/008376 A3 (Jan. 30, 2003); Northerwestern University (Applicant); Messersmith, et al. (inventors).

Ishihara, et al., "Photocrosslinkable chitosan as a dressing wound occlusion and accelerator in healing process," *Biomaterials*, vol. 23, No. 3 (2002), pp. 833-840.

Jackson, "Tissue sealants: Current status, future potential," *Nat. Med.*, vol. 2, No. 5, (May 1996), pp. 637-638.

Jackson, "Fibrin sealants in surgical practice: An overview," *Am. J. Surg.*, vol. 182 (2001), pp. 1S-7S.

Jänchen, et al., "Adhesion Energy of Thin Collagen Coatings and Titanium," *Surf. Interface Anal.*, vol. 27 (1999), pp. 444-449.

Jensen, et al., "Lipopeptides Incorporated into Supported Phospholipid Monolayers Have High Specific Activity at Low Incorporation Levels," *J. Am. Chem. Soc.*, vol. 126, No. 46 (2004), pp. 15223-15230.

Jeon, et al., "Protein-Surface Interactions in the Presence of Polyethylene Oxide," *J. Colloid. Interface Sci.*, vol. 142, No. 1 (1991), pp. 159-166.

Jewell, et al., "Pharmacokinetics of RheothRx Injection in Healthy Male Volunteers," *J. Phar. Sci.* vol. 86, No. 7 (1997), pp. 808-812.

Jo, et al., "Surface modification using silanated poly(ethylene glycol)s," *Biomaterials*, vol. 21 (2000), pp. 605-616.

Johnson, et al., "Surface Energy and Contact of Elastic Solids," *Proc. R. Soc. Lond., A*, vol. 324, No. 1558 (1971), pp. 301-313.

Jones, et al., "Controlled Surface-Initiated Polymerization in Aqueous Media," *Adv. Mater.*, vol. 13, No. 16 (2001), pp. 1256-121259.

Jones, et al., "In Situ forming biomaterials," *Oral Maxillofacial Surg. Clin. N. Am.*, vol. 14 (2002), pp. 29-38.

Kahlem, et al., "Peptides containing glutamine repeats as substrates for transglutaminase-catalyzed cross-linking: Relevance to diseases of the nervous system," *Proc. Natl. Acad. Sci. USA*, vol. 93 (Dec. 1996), pp. 14580-14585.

Kellaway, et al., "Oral Mucosal Drug Delivery," in *Oral Mucosal Drug Delivery*, Rathbone (ed.). 1996, Marcel Dekkers, Inc.: New York, NY. pp. 221-239.

Kenausis, et al., "Poly(L-lysine)-g-Poly(ethylene glycol) Layers on Metal Oxide Surfaces: Attachment Mechanism and Effects on Polymer Architecture on Resistance to Protein Adsoprtion," *J. Phys. Chem. B*, vol. 104 (2000), pp. 3298-3309.

Khudyakov, et al., "Kinetics of Photopolymerization of Acrylates with Functionality of 1-6," *Ind. Eng. Chem. Res.* 38 (1999). pp. 3353-3359.

Kingshott, et al., "Effects of cloud-point grafting, chain length, and density of PEG layers on competitive adsorption of ocular proteins," *Biomaterials* 23 (2002). pp. 2043-2056.

Kirschenbaum, et al., "Sequence-specific polypeptides: A diverse family of heteropolymers with stable secondary structure," *Proc. Natl. Acad. Sci. USA* 95 (1998). pp. 4303-4308.

Kitano, et al., "Resistance of zwitterionic telomers accumulated on metal surfaces against nonspecific adsorption of proteins," *J. Colloid Interface Sci.* 282 (2005). pp. 340-348.

Klug, et al, "In Situ Analysis of Peptidyl DOPA in Mussel Byssus Using Rotational-Echo Double-Resonance NMR," *Arch. Biochem. Biophys.*, vol. 333, No. 1 (Sep. 1, 1996), pp. 221-224.

Kolb, et al., "Click Chemistry: Diverse Chemical Function from a Few Good Reactions," *Agnew. Chem. Int. Ed.*, vol. 40 (2001), pp. 2005-2021.

Koob, et al., "Mechanical and thermal properties of novel polymerized NDGA-gelatin hydrogels," *Biomaterials*, vol. 24 (2003), pp. 1285-1292.

Korobkova, et al., "From molecular noise to behavioural variability in a single bacterium," *Nature* 428 (2004). pp. 574-578.

Kummert, et al., "The Surface Complexation of Organic Acids of Hydrous $\gamma$-Al$_2$O$_3$," *J. Colloid Interface Sci.*, vol. 75, No. 2 (Jun. 1980), pp. 373-385.

Laucournet, et al., "Catechol derivatives and anion adsorption onto alumina surfaces in aqueous media: influence on the electrokinetic properties," *J. Eur. Ceram. Soc.* 21 (2001). pp. 869-878.

LaVoie, et al., "Dopamine covalently modifies and functionally inactivates parkin," *Nature Med.* 11 (11), 2005. pp. 1214-1221.

Lee, et al., "Enzymatic and Non-Enzymatic Pathways to Formation of DOPA-Modified PEG Hydrogels," *Polymer Preprints* 42 (2), 2001. pp. 151-152.

Lee, et al., "Synthesis and Gelation of DOPA-Modified Poly(ethylene glycol) Hydrogels," *Biomacromolecules* 3 (2002). pp. 1038-1047.

Lee, et al., "Synthesis of 3,4-dihydroxyphenylalanine (DOPA) containing monomers and their co-polymerizations with PEG-diacrylate to form hydrogels," *J. Biomater. Sci. Polymer Edn*, 15 (4), 2004. pp. 449-464.

Lee, et al., "Rapid Gel Formation and Adhesion in Photocurable and Biodegradable Block Copolymers with High DOPA Content," *Macromolecules* 39 (2006). pp. 1740-1748.

Lee, et al., "Biomimetic Adhesive Polymers Based on Mussel Adhesive Proteins," in *Biological Adhesives*, Smith, et al. (eds.), Springer-Verlag: Berlin Heidelberg, 2006. pp. 257-278.

Lee, et al., "Single-Molecule Mechanics of Mussel Adhesion," *Proc. Natl. Acad. Sci. USA*, vol. 103, No. 35 (2006), pp. 12999-13003.

Lee, et al., "Bioadhesive-Based Dosage Forms: The Next Generation," *J. Pharm. Sci.* 89 (7) (2000). pp. 850-866.

Lee, et al., "Hydrogels for Tissue Engineering," *Chem. Rev.*, vol. 101, No. 7 (Jul. 2001), pp. 1869-1879.

Lemieux, et al., "Block and Graft Copolymers and Nanogel™ Copolymer Networks for DNA Delivery into Cell," *J. of Drug Targeting* 8 (2), 2000. pp. 91-105.

Li, et al., "Protein Adsortion on Oligo(ethylene glycol)-Terminated Alkanethiolate Self-Assembled Monolayers: The Molecular Basis for Nonfouling Behavior," *J. Phys. Chem. B* 109 (2005). pp. 2934-2941.

Li, et al., "Copper-Based Metallization for ULSI Applications," *MRS Bulletin* 18 (6), Jun. 1993. pp. 18-21.

Li, et al., "Chemical Modifications of Surface Active Poly(ethylene oxide)—Poly(propylene oxide) Triblock Copolymers," *Bioconj. Chem.* 7 (1996). pp. 592-599.

Li, et al., "Two-Level Antibacterial Coating with Both Release-Killing and Contact-Killing Capabilities," *Langmuir* 22 (24), 2006. pp. 9820-9823.

Long, et al., "A peptide that inhibits hydroxyapatite growth is in an extended conformation on the crystal surface," *Proc. Natl. Acad. Sci. USA* 95 (1998). pp. 12083-12087.

Lorand, et al., "Transglutaminases," *Mol. Cell. Biochem.*, vol. 58 (1984), pp. 9-35.

Love, et al., "Self-Assembled Monolayers of Thiolates on Metals as a Form of Nanotechnology," *Chem. Rev.* 105 (2005). pp. 1103-1169.

Lovich, et al., "Arterial heparin deposition: role of diffusion, convection, and extravascular space," *Am. J. Phsyiol.—Heart C.*, vol. 275 (1998), pp. 2236-2242.

Lu, et al., "Studies on the synthesis and antibacterial activities of polymeric quaternary ammonium salts from dimethylaminoethyl methacrylate," *Reactive & Functional Polymers* 67 (2007). pp. 355-366.

Lucast, "Adhesive considerations for developing stick-to-skin products," *Adhesives Age* 43 (2000). pp. 36, 38-39.

Luo, et al., "Surface-Initiated Photopolymerization of Poly(ethylene glycol) Methyl Ether Methacrylate on a Diethyldithiocarbamate-Mediated Polymer Substrate," *Macromolecules*, vol. 35 (2002), pp. 2487-2493.

Lyman, et al., "Characterization of the formation of interfacially photopolymerized thin hydrogels in contact with arterial tissue," *Biomaterials* 17 (1996). pp. 359-364.

Martin, et al., "Surface Structures of a 4-Chlorocatechol Adsorbed on Titanium Dioxide," *Environ. Sci. Technol.*, vol. 30 (1996), pp. 2535-2542.

Maugh, et al., "Recombinant bioadhesive proteins of marine animals anad their use in adhesive compositions," in Genex Corp. 1988: USA. pp. 196 (1987).

Matyjaszewski, et al., "Atom Transfer Radical Polymerization," *Chem. Rev.* 101 (2001). pp. 2921-2990.

McBride, "Adsorption and Oxidation of Phenolic Compounds by Iron and Manganese Oxides," *Soil Sci. Soc. Am. J.*, vol. 51 (1987), pp. 1466-1472.

McWhitrter, et al., "Siderophore-Mediated Covalent Bonding to Metal (Oxide) Surfaces during Biofilm Initiation by *Pseudomonas aeruginosa* Bacteria," *Langmuir*, vol. 19 (2003), pp. 3575-3577.

Meisel, et al., "Estimation of calcium-binding constants of casein phosphopeptides by capillary zone electrophoresis," *Anal. Chim. Acta* 372 (1998). pp. 291-297.

Mellott, et al., "Release of protein from highly cross-linked hydrogels of poly(ethylene glycol) diacrylate fabricated by UV polymerization," *Biomaterials*, vol. 22 (2001), pp. 929-941.

Merrifield, "Solid Phase Peptide Synthesis. I. The Synthesis of a Tetrapeptide," *J. Am. Chem. Soc.*, vol. 85 (Jul. 20, 1963), pp. 2149-2154.

Merrill, "Distinctions and Correspondences among Surfaces Contacting Blood," *Annals of the NY Acad. Sci.* 516 (1987). pp. 196-203.

Miron, et al., "A Simplified Method for the Preparation of Succinimidyl Carbonate Polyethylene Glycol for Coupling to Proteins," *Bioconj. Chem.* 4 (1993). pp. 568-569.

Morgan, et al., "Biochemical characterisation of polycation-induced cytotoxicity to human vascular endothelial cells," *Journal of Cell Science* 94 (3), 1989,. pp. 553-559.

Morikawa, "Tissue sealing," *Am. J. Surg.*, vol. 182 (2001), pp. 29S-35S.

Mougin, et al., "Construction of Cell-Resistant Surfaces by Immobilization of Poly(ethylene glycol) on Gold," *Langmuir*, vol. 20 (2004), pp. 4302-4305.

Mowery, et al., "Adhesion of Thermally Reversible Gels to Solid Surfaces," *Langmuir*, vol. 13 (1997), pp. 6101-6107.

Mrksich, et al., "Using Self-Assembled Monolayers that Present Oligo(ethylene glycol) Groups to Control the Interactions of Proteins with Surfaces," *American Chemical Society Symposium Series on Chemistry and Biological Applications of Polyethylene Glycol*, vol. 680 (1997), pp. 361-373.

Mukkamala, et al., "Hydrogel Polymers from Alkylthio Acrylates for Biomedical Applications," *Polymer Gels: Fundamentals and Applciations* 833 (2003). pp. 163-174.

Müller, et al., "Interaction of differentiated HL60 cells with poloxamer and poloxamine surface modified model drug carriers," *Eur. J. Phar. Sci.* 5 (1997). pp. 147-153.

Nakagawa, et al., "ENH, Containing PDZ and LIM Domains, Heart/Skeletal Muscle-Specific Protein, Associates with Cytoskeletal Proteins through the PDZ Domain," *Biocehm. Biophys. Res. Commun.* 272 (2000). pp. 505-512.

Nakayama, et al., "Newly Designed Hemostatic Technology Based on Photocurable Gelatin," *ASAIO J.*, vol. 41, No. 3 (1995), pp. M374-M378.

Nakayama, et al., "Photocurable Surgical Tissue Adhesive Glues Composed of Photoreactive Gelatin and Poly(ethylene glycol) Diacrylate," *J. Biomed. Mater. Res.*, vol. 48, Issue 4 (1999), pp. 511-521.

Nakayama, et al., "Development of high-performance stent: gelatinous photogel-coated stent that permits drug delivery and gene transfer," *J. Biomed. Mater. Res.*, vol. 57, Issue 4 (2001), pp. 559-566.

Nakonieczna, et al., "A New Convenient Route for the Synthesis of DOPA Peptides," *Liebigs Annalen der Chemie*, Issue 10 (1994). pp. 1055-1058.

Neff, et al., "A novel method for surface modification to promote cell attachment to hydrophobic substrates," *J. Biomed. Mater. Res.* 40 (1998). pp. 511-519.

Ninan, et al., "Adhesive strength of marine mussel extracts on porcine skin," *Biomaterials* 24 (2003). pp. 4091-4099.

Nishiyama, et al., "Effects of a strucutural change in collagen upon binding to conditioned dentin studied by $^{13}C$ NMR," *J. Biomed. Mater. Res.*, vol. 29 (1995), pp. 107-111.

Nishiyama, et al., "Adhesion mechanisms of resin to etched dentin primed with N-methacryloyl glycine studied by $^{13}C$-NMR," *J. Biomed. Mater. Res.*, vol. 40 (1998). pp. 458-463.

Nishiyama, et al., "Adhesion of N-Methacryloyl-ω-Amino Acid Primers to Collagen Analyzed by $^{13}C$ NMR," *J. Dent. Res.*, vol. 80, No. 3 (2001), pp. 855-859.

Northen, et al., "A batch fabricated biomimetic dry adhesive," *Nanotechnology* 16 (8), 2005. pp. 1159-1166.

Northen, et al., "Meso-scale adhesion testing of integrated micro- and nano-scale structures," *Sensors and Actuators A* 130-131 (2006). pp. 583-587.

Nyström, et al., "Dynamic Light Scattering and Rheological Studies of Thermoreversible Gelation of a Poly(ethylene oxide)-Poly(propylene oxide)-Poly(ethylene oxide) Triblock Copolymer in Aqueous Solution," *Faraday Discuss.* 101 (1995). pp. 335-344.

Nyström, et al., "Dynamic Viscoelasticity of an Aqueous System of a Poly(ethylene oxide)—Poly(propylene oxide)—Poly(ethylene oxide) Triblock Copolymer during Gelation," *J. Phys. Chem.* 100 (1996). pp. 5433-5439.

O'Keefe, et al., "Poloxamer-188 as an Adjunct to Primary Percutaneous Transluminal Coronary Angioplasty for Acute Myocardial Infarction," *Am. J. Cardiol.* 78 (1996). pp. 747-750.

Okino, et al., "In situ hydrogelation of photocurable gelatin and drug release," *J. Biomed. Mater. Res.*, vol. 59, Issue 2 (2001), pp. 233-245.

Online Medical Dictionary. "Amino acid." Available from: http//cancerweb.ncl.ac.uk/cgi-bin/omd?query=amino+acid, (Changes as content changes).

Ono, et al., "Photocrosslinkable chitosan as a biological adhesive," *J. Biomed. Mater. Res.*, vol. 49, Issue 2 (1999), pp. 289-295.

Ooka, et al., "Surface-Enhanced Raman Spectroscopy of DOPA-Containing Peptides Related to Adhesive Protein of Marine Mussel, *Mytilus edulis,*" *Biopolymers (Biospectroscopy)*, vol. 57, Issue 2 (2000), pp. 92-102.

Orban, et al., "Cytomimetic Biomaterials. 4. In-Situ Photopolymerization of Phospholipids on an Alkylated Surface," *Macromolecules* 33 (2000). pp. 4205-4212.

Ostuni, et al., "A Survey of Structure—Property Relationships of Surfaces that Resist the Adsorption of Protein," *Langmuir* 17 (2001). pp. 5605-5620.

Palmer, et al., "Surfactant Administration Reduces Testicular Ischemia-Reperfusion Injury," *J. Urol.* 159 (1998). pp. 2136-2139.

Papov, et al., "Hydroxyarginine-containing Polyphenolic Proteins in the Adhesive Plaques of the Marine Mussel *Mytilus edulis,*" *J. Biol. Chem.* 270 (34) (1995). pp. 20183-20192.

Pardo, et al., "Purification of Adhesive Proteins from Mussels," *Protein Expression and Purif.* 1 (2), 1990. pp. 147-150.

Parsons, "Characteristics of the amino acids as components of a peptide hormone sequence," in *Peptide Hormones*, University Park Press: 1976. pp. 1-7.

Pasche, et al., "Effects of Ionic Strength and Surface Charge on Protein Adsorption at PEGylated Surfaces," *J. Phys. Chem. B* 109 (2005). pp. 17545-17552.

Patel, et al., "Synthesis of Benzyl Esters of α-Amino Acids," *J. Org. Chem.* 30 (1965). pp. 3575-3576.

Peressadko, et al, "When Less is More: Experimental Evidence for Tenacity Enhancement by Division of Contact Area," *J. Adhes.* 80 (2004). pp. 247-261.

Perruchot, et al., "Synthesis of Well-Defined, Polymer-Grafted Silica Particles by Aqueous ATRP," *Langmuir*, vol. 17 (2001), pp. 4479-4481.

Pierpont, et al., "Transition Metal Complexes of *o*-Benzoquinone, *o*-Semiquinone, and Catecholate Ligands," *Coord. Chem. Rev.*, vol. 38 (1981), pp. 45-87.

Preul, et al., "Use of a Novel Hydrogel Sealant in a Canine Dural Repair Model," Presented at the American Association of Neurological Surgeons; Apr. 2002, Chicago, IL. Available from: http://www.confluentsurgical.com/pdf/ds/Abstract0BNI_PreulAbstract.pdf.

Preul, et al., "Obtaining Watertight Closures of Duraplasty Onlay Grafts in a Craniotomy Preclinical Model," Confluent Surgical, Inc. (2005), 'White Paper.' Available from: http://www.confluentsurgical.com/pdf/LT-6000-034RevA-DuraSeal_duraplasty_study_white_paper.pdf.

Prime, et al., "Adsorption of Proteins onto Surfaces Containing End-Attached Oligo(ethylene oxide): A Model System Using Self-Assembled Monolayers," *J. Am. Chem. Soc.* 115 (1993). pp. 10714-10721.

Prucker, et al., "Polymer Layers through Self-Assembled Monolayers of Initiators," *Langmuir*, vol. 14 (1998), pp. 6893-6898.

Ramakrishna, et al., "Effect of Particle Size on the Reactivity of Quantum Size ZnO Nanoparticles and Charge-Transfer Dynamics with Adsorbed Catechols," *Langmuir*, vol. 19 (2003), pp. 3006-3012.

Ranger, et al., "Pneumostasis of Experimental Air Leaks with a New Photopolymerized Synthetic Tissue Sealant," *Am. Surg.*, vol. 63, Issue 9 (1997), pp. 788-795.

Reed, et al., "A One-Step Synthesis of Monoprotected Polyethylene Glycol Ethers," *J. Org. Chem.*, vol. 65 (2000), pp. 5843-5845.

Rodríguez, et al., "Surface Complexation at the $TiO_2$ (anatase)/Aqueous Solution Interface: Chemisorption of Catechol," *J. Colloid Interface Sci.*, vol. 177 (1996), pp. 122-131.

Rodríguez-Hernández, et al., "High Branched Poly(L-lysine)," *Biomacromolecules*, vol. 4 (2003), pp. 249-258.

Ross-Murphy, "Rheological Characterization of Polymer Gels and Networks," *Polym. Gels Networks*, vol. 2 (1994), pp. 229-237.

Rozier, et al., "Gelrite®: A novel, ion-activated, in situ gelling polymer for ophthalmic vehicles. Effect on bioavailability of timolol, *Int. J. Pharm.* 57 (2), 1989. pp. 163-168.

Ruel-Gariépy, et al., "In situ-forming hydrogels—review of temperature-sensitive systems," *Eur. J. Pharm. Biopharm.* 58 (2004). pp. 409-426.

Ruibal, et al., "The Structure of the Digital Setae of Lizards," *J. Morph.* 117 (1965). pp. 271-294.

Ryu, et al., "A Generalized Approach to the Modification of Solid Surfaces," *Science* 308 (2005). pp. 236-239.

Rzepecki, et al., "α,β-Dehydro-3,4-dihydroxyphenylalanine Derivatives: Potential Schlerozation Intermediates in Natural Composite Materials," *Arch. Biochem. Biophys.* 285 (1) (1991). pp. 17-26.

Rzepecki, et al., "Wresting the muscle from mussel beards: research and applications," *Mol. Mar. Biol. Biotech.* 4 (4) (1995). pp. 313-322.

Rzepecki, et al., "Bioadhesives: DOPA and Phenolic proteins as components of organic composite materials", *Principles of Cell Adhesion*, P.D. Richardson and M. Steiner (eds.), CRC Press, Boca Raton, FL. (1995). pp. 107-142142.

Saby, et al., "*Mytilus edulis* Adhesive Protein (MAP) as an Enzyme Immobilization Matrix in the Fabrication of Enzyme-Based Electrodes," *Electroanalysis* 10 (17) (1998). pp. 1193-1199.

Sanborn, et al., "In situ crosslinking of a biomimetic peptide-PEG hydrogel via thermally triggered activation of factor XIII," *Biomaterials*, vol. 23 (2002), pp. 2703-2710.

Sawada, et al., "Micropatterning of Copper on a Poly(ethylene terephthalate) Substrate Modified with a Self-Assembled Monolayer," *Langmuir* 22 (2006). pp. 332-337.

Sawhney, et al., "Interfacial photopolymerization of poly(ethylene glycol)-based hydrogels upon alginate-poly(*l*-lysine) microcapsules for enhanced biocompatibility," *Biomaterials*, vol. 14, No. 13 (1993), pp. 1008-1016.

Sawhney, et al., "Bioerodible Hydrogels Based on Photopolymerized Poly(ethylene glycol)-*co*-poly(α-hydroxy acid) Diacrylate Macromers," *Macromolecules*, vol. 26 (1993), pp. 581-587.

Schmolka, "Articifial Skin. I. Preparation and Properties of Pluronic F-127 Gels for Treatment of Burns," *J. Biomed. Mater. Res.* 6 (6) (1972). pp. 571-582.

Schnurrer, et al., "Mucoadhesive properties of the mussel adhesive protein," *Int. J. Pharm.* 141 (1996). pp. 251-256.

Sever, et al., "Synthesis of peptides containing DOPA (3.4-dihydroxyphenylalanine)," *Tetrahedron* 57 (2001). pp. 6139-6146.

Sever, et al., "Metal-Mediated Cross-Linking in the Generation of a Marine-Mussel Adhesive," *Angew. Chem. Int. Ed.*, vol. 43 (2004), pp. 448-450.

Shull, et al., "Fracture Mechanics Studies of Adhesion in Biological Systems," *Interface Sci.*, vol. 8 (2000), pp. 95-110.

Shull, "Contact mechanics and the adhesion of soft solids," *Mater. Sci. Eng., R* 36 (2002). pp. 1-45.

Sichel, et al., "Relationship Between Melanin Content and Superoxide Dismutase (SOD) Activity in the Liver of Various Species of Animals," *Cell Biochem. Funct.* 5 (1987). pp. 123-128.

Sierra, "Fibrin Sealant Adhesive Systems: A Review of Their Chemistry, Material Properties and Clinical Applications," *J. Biomed. Appl.*, vol. 7 (1993), pp. 309-352.

Sitti, et al., "Synthetic Gecko Foot-Hair Micro/Nano-Structures as Dry Adhesives," *J. Adhes. Sci. Technol.*, vol. 17, No. 8 (2003), pp. 1055-1073. Available from: http://nanolab.me.cmu.edu/publications/papers/Sitti-JAST2003.pdf.

Skelhorne, et al., "Hydrogel Adhesives for Wound-Care Applications," *Medical Device Technology* (Nov. 2002). pp. 19-23.

Soriaga, et al., "Determination of the Orientation of Adsorbed Molecules at Solid-Liquid Interfaces by Thin-Layer Electrochemistry: Aromatic Compounds at Platinum Electrodes," *J. Am. Chem. Soc.* 104 (1982). pp. 2735-2742.

Sousa, et al., "Human Serum Albumin Adsorption on $TiO_2$ from Single Protein Solutions and from Plasma," *Langmuir*, vol. 20 (2004), pp. 9745-9754.

Sperinde, et al., "Synthesis and Characterization of Enzymatically-Cross-Linked Poly(ethylene glycol) Hydrogels," *Macromolecules* 30 (18) (1997). pp. 5255-5264.

Sperinde, et al., "Control and Prediction of Gelation Kinetics in Enzymatically Cross-Linked Poly(ethylene glycol) Hydrogels," *Macromolecules* 33 (2000). pp. 5476-5480.

Spolenak, et al., "Adhesion design maps for bio-inspired attachment systems," *Acta. Biomater.* 1 (2005). pp. 5-13.

Spotnitz, "History of Tissue Adhesives." In: Sierra, et al. (eds.), *Surgical Adhesives and Sealants: Current Technology and Applications*. Technomic Publishing Company, Inc.: Lancaster, PA (1997). pp. 3-11.

Spotnitz, "Commercial fibrin sealants in surgical care," *Am. J. Surg.* 182 (2001). pp. 8S-14S.
Statz, et al., "New Peptidomimetic Polymers for Antifouling Surfaces," *J. Am. Chem. Soc.*, vol. 127, No. 22 (2005), pp. 7972-7973.
Stevens, "Trace bio-organic constituents of gelatins—a review," *Food Australia*, vol. 44, No. 7 (1992), pp. 320-324.
Stile, et al., "Sequential robust design methodology and X-ray photoelectron spectroscopy to analyze the grafting of hyaluronic acid to glass substrates," *J. Biomed. Mater Res.*, vol. 61, Issue 3 (2002), pp. 391-398.
Stiles, et al., "Axisymmetric Adhesion Test to Examine the Interfacial Interactions between Biologically-Modified Networks and Models of the Extracellular Matrix," *Langmuir*, vol. 19 (2003), pp. 1853-1860.
Strausberg, et al., "Protein-based medical adhesives," *Trends in Biotechnology* 8 (2) (1990). pp. 53-57.
Strausberg, et al., "Development of a microbial system for production of mussel adhesive protein." In: *Adhesives from Renewable Resources*. Hemingway, et al. (eds.), ACS Symposium Series 385, American Chemical Society, Washington, D.C (1989). pp. 453-464.
Sugumaran, et al., "Chemical- and Cuticular Phenoloxidase-Mediated Synthesis of Cysteinyl-Catechol Adducts," *Arch. Insect Biochem. Physiol.* 11 (2) (1989). pp. 127-137.
Sugumaran, "Unified Mechanism for Sclerotization of Insect Cuticle," *Adv. Insect. Physiol.*, vol. 27 (1998), pp. 229-334.
Sun, et al., "Improved antifouling property of zwitterionic ultrafiltration membrane composed of acrylonitrile and sulfobetaine copolymer," *J. of Memr. Sci.* 285 (2006). pp. 299-305.
Sun, et al., "The Nature of the Gecko Lizard Adhesive Force," *Biophys. J.* 89 (2005). pp. L14-L16.
Swerdloff, et al., "Solid phase synthesis of bioadhesive analogue peptides with trifluoromethanesulfonic acid cleavage from PAM resin," *Int. J. Peptide Protein Res.*, vol. 33 (1989), pp. 318-327.
Tae, et al., "Sustained release of human growth hormone from in situ forming hydrogels using self-assembly of fluoroalkyl-ended poly-(ethylene glycol)," *Biomaterials*, vol. 26 (2005), pp. 5259-5266.
Taira, et al., "Analysis of Photo-iniators in Visible-light-cured Dental Composite Resins," *J. Dent. Res.*, vol. 67, No. 1 (1988), pp. 24-28.
Tan, et al., "Surface modification of nanoparticles by PEO/PPO block copolymers to minimize interactions with blood components and prolong blood circulation in rats," *Biomaterials*, vol. 14, No. 11 (1993), pp. 823-833.
Tatehata, et al., "Model Polypeptide of Mussel Adhesive Protein. I. Synthesis and Adhesive Studies of Sequential Polypeptides (X-Tyr-Lys)$_n$ and (Y-Lys)$_n$," *J. Appl. Polym. Sci.*, vol. 76, No. 6 (2000), pp. 929-937.
Taylor, et al., "Polargraphic and Spectrophotometric Investigation of Iron(III) Complexation to 3,4-Dihydroxyphenylalanine-Containing Peptides and Proteins from *Mytilus edulis*," *Inorg. Chem.*, vol. 33 (1994), pp. 5819-5824.
Taylor, et al., "*trans*-2,3-*cis*-3,4-Dihydroxyproline, a New Naturally Occurring Amino Acid, Is the Sixth Residue in the Tandemly Repeated Consensus Decapeptides of an Adhesive Protein from *Mytilus edulis*," *J. Am. Chem. Soc.*, vol. 116 (1994), pp. 10803-10804.
Taylor, et al., "Ferric Ion Complexes of a DOPA-Containing Adhesive Protein from *Mytilus edulis*," *Inorg. Chem.*, vol. 35 (1996), pp. 7572-7577.
Uyama, et al., "Surface Modification of Polymers by Grafting," *Advances in Polymer Science*, vol. 137 (1998), pp. 1-39.
Venkatraman, et al., "Skin adhesives and skin adhesion. 1. Transdermal drug delivery systems," *Biomaterials*, vol. 19 (1998), pp. 1119-1136.
Vörös, et al., "Optical grating coupler biosensors," *Biomaterials*, vol. 23 (2002), pp. 3699-3710.
Waite, "Evidence for a Repeating 3,4-Dihydroxyphenylalanine- and Hydroxyproline-containing Decapeptide in the Adhesive Protein of the Mussel, *Mytilus edulis* L.," *J. Biol. Chem.*, vol. 258, No. 5 (1983), pp. 2911-2915.
Waite, et al., "Assay of Dihdroxyphenylalanine (Dopa) in Invertebrate Structural Proteins," *Methods Enzymol.*, vol. 107 (1984), pp. 397-413.
Waite, "Adhesion à la Moule," *Integr. Comp. Biol.*, vol. 42 (2002), pp. 1172-1180.
Waite, "Mussel Beards: A Coming of Age" *Chem. Ind.* (Sep. 2, 1991), pp. 607-611.
Waite, "Nature's underwater adhesive specialist," *Int. J. Adhes. Adhes.*, vol. 7, No. 1 (1987), pp. 9-14.
Waite, "Nature's underwater adhesive specialist," *Chemtech*, vol. 17 (1987), pp. 692-697.
Waite, et al., "3,4-Dihydroxyphenylalanine in an Insoluble Shell Protein of *Mytilus edulis*," *Biochem. Biophys. Acta*, vol. 541 (1978), pp. 107-114.
Waite, et al., "Polyphosphoprotein from the Adhesive Pads of *Mytilus edulis*," *Biochemistry*, vol. 40 (2001), pp. 2887-2893.
Waite, et al., "The Bioadhesive of *Mytilus byssus*: A Protein Containing L-DOPA," *Biochem. & Biophy. Res. Comm.*, vol. 96, No. 4 (1980), pp. 1554-1561.
Waite, et al., "Mussel Adhesion: Finding the Tricks Worth Mimicking," *J. Adhes.*, vol. 81 (2005), pp. 297-317.
Waite, et al., "Polyphenolic Substance of *Mytilus edulis*: Novel Adhesive Containing L-Dopa and Hydroxyproline," *Science*, vol. 212, No. 4498 (1981), pp. 1038-1040.
Waite, "Precursors of Quinone Tanning: Dopa-Containing Proteins," *Methods Enzymol.*, vol. 258 (1995), pp. 1-21.
Wang, et al., "Facile synthesis of well-defined water-soluble polymers via atom transfer radical polymerization in aqueous media at ambient temperature," *Chem. Commun.* (1999), pp. 1817-1818.
Wang, et al., "Facile Atom Transfer Radical Polymerization of Methoxy-Capped Oligo(ethylene glycol) Methacrylate in Aqueous Media at Ambient Temperature," *Macromolecules*, vol. 33 (2000), pp. 6640-6647.
Wanka, et al., "The aggregation behavior of poly-(oxyethylene)-poly-(oxypropylene)-poly-(oxyethylene)-block-copolymers in aqueous solution," *Cooloid. Polym. Sci.*, vol. 268 (1990), pp. 101-117.
Warner, et al., "Expression of multiple forms of an adhesive plaque protein in an individual mussel, *Mytilus edulis*," *Mar. Biol.*, vol. 134 (1999), pp. 729-734.
Watanabe, et al., "Bonding durability of photocured phenyl-P in TEGDMA to smear layer-retained bovine dentin," *Quint. Int.*, vol. 24, No. 5 (1993), pp. 335-342.
Webber, et al., "Effects of geometric confinement on the adhesive debonding of soft elastic solids," *Phys. Rev. E*, vol. 68 (2003), pp. 021805-1-*to*-021805-11.
Whitesides, "The origins and the future of microfluidics," *Nature*, vol. 442 (2006), pp. 368-373.
Wisniewski, et al., "Methods for reducing biosensor membrane biofouling," *Colloids Surf., B*, vol. 18 (2000), pp. 197-219.
Yamada, "Chitosan Based Water-Resistant Adhesive. Analogy to Mussel Glue," *Biomacromolecules*, vol. 1 (2000), pp. 252-258.
Yamamoto, "Marine Adhesive Proteins and Some Biotechnological Applications," *Biotechnol. Genet. Eng. Rev.*, vol. 13 (1996), pp. 133-165.
Yamamoto, "Adhesive studies of synthetic polypeptides: A model for marine adhesive proteins," *J. Adhesion Sci. Tech.*, vol. 1, No. 2 (1987), pp. 177-183.
Yamamoto, "Synthesis and Adhesive Studies of Marine Polypeptides," *J. Chem. Soc. Perkin Trans.*, vol. 1 (1987), pp. 613-618.
Yamamoto, "Insolubilizing and adhesive studies of water-soluble synthetic model proteins," *Int. J. Biol. Macromol.*, vol. 12 (1990), pp. 305-310.
Yamamoto, et al., "Synthesis and Adhesives of Marine Adhesive Proteins of the Chilean Mussel *Aula comya ater*," *Biomimetics*, vol. 1, No. 3 (1992), pp. 219-238.
Yamamoto, et al., "Work of Adhesion of Synthetic Polypeptides Containing *L*-Lysine," *J. Colloid Interface Sci.*, vol. 156 (1993), pp. 515-517.
Yamamoto, et al., "Wettability and Adhesion of Synthetic Marine Adhesive Proteins and Related Model Compounds," *J. Colloid Interface Sci.*, vol. 176 (1995), pp. 111-116.
Yang, et al., "Physicochemical aspects of drug delivery and release from polymer-based colloids," *Curr. Opin. Colloid Interface Sci.*, vol. 5 (2000), pp. 132-143.

Young, et al., "Marine Animals and Adhesion." In: Allen (ed.), *Adhesion 6*. Applied Science Publishers: London and New Jersey, 1982. pp. 19-39.

Yu, et al., "Micellisation and Gelation of Triblock Copoly(oxyethylene/oxypropylene/oxyethylene), F127," *J. Chem. Soc., Faraday Trans.*, vol. 88, No. 17 (1992), pp. 2537-2544.

Yu, et al., "Synthetic Polypeptide Mimics of Marine Adhesives," *Macromolecules*, vol. 31 (1998), pp. 4739-4745.

Yu, et al., "Role of L-3,4-Dihydroxyphenylalanine in Mussel Adhesive Proteins," *J. Am. Chem. Soc.*, vol. 121 (1999), pp. 5825-5826.

Yurdumakan, et al., "Synthetic gecko foot-hairs from multiwalled carbon nanotubes," *Chem. Commun.*, vol. 30 (2005), pp. 3799-3801.

Zekorn, et al., "Biocompatibility and immunology in the encapsulation of islets of Langerhans (bioartificial pancreas)," *Int. J. Artif. Organs*, vol. 19, No. 4 (1996), pp. 251-257.

Zeng, et al., "Synthesis and Characterization of DOPA-PEG Conjugates," *Polymer Preprints*, vol. 41, No. 1 (2000), pp. 989-990.

Zhan, et al., "Functionalization of Nano-Faujasite Zeolite with PEG-Grafted PMA Tethers Using Atom Transfer Radical Polymerization," *Macromolecules*, vol. 37 (2004), pp. 2748-2753.

Zhao, et al., "Polymer brushes: surface-immobilized macromolecules," *Prog. Polym. Sci.*, vol. 25 (2000), pp. 677-710.

Zuckermann, et al., "Efficient Method for the Preparation of Peptoids [Oligo(N-substituted glycines)] by Submonomer Solid-Phase Synthesis," *J. Am. Chem. Soc.*, vol. 114 (1992), pp. 10646-10647.

Dalsin et al., Bioinspired Antifouling Polymers. Materials Today 2005, 8, 9 (38-46).

Gristina, Biomaterial-Centered Infection—Microbial Adhesion Versus Tissue Integration. Science 1987, 237, (4822), 1588-1595.

Evans et al., Iron Chelator, Exopolysaccharide and Protease Production in Staphylococcus-Epidermidis—a Comparative-Study of the Effects of Specific Growth-Rate in Biofilm and Planktonic Culture. Microbiology-Uk 1994, 140, 153-157.

Yu et al., Adhesion of Coagulase-Negative Staphylococci and Adsorption of Plasma-Proteins to Heparinized Polymer Surfaces. Biomaterials 1994, 15, (10), 805-814.

Jose et al., Vancomycin covalently bonded to titanium beads kills *Staphylococcus aureus*. Chemistry & Biology 2005, 12, (9), 1041-1048.

Desai et al., Surface-Immobilized Polyethylene Oxide for Bacterial Repellence. Biomaterials 1992, 13, (7), 417-420.

Burdinski et al., Universal Ink for Microcontact Printing. Angwandte Chemie 2006, 45, 1-5.

Floriolli et al., Marine surfaces and the expression of specific byssal adhesive protein variants in *Mytilus*. Mar Biotechnol 2000, 2, 352-363.

Bain et al., Molecular-level Control over Surface Order in Self-Assembled Monolayer Films of Thiols on Gold. Science 1988, 240, (4848), 62-63.

Waite, Reverse engineering of bioadhesion in marine mussels. Bioartificial Organs ii: Technology, Medicine, and Materials 1999, 875, 301-309.

Pasche et al., Poly(l-lysine)-graft-poly(ethylene glycol) assembled monolayers on niobium oxide surfaces: A quantitative study of the influence of polymer interfacial architecture on resistance to protein adsorption by ToF-SIMS and in situ OWLS. Langmuir 2003,19, (22), 9216-9225.

Zhang et al., Reactive coupling of poly(ethylene glycol) on electroactive polyaniline films for reduction in protein adsorption and platelet adhesion. Biomaterials 2002, 23, (3), 787-795.

Holl et al., Solid-State NMR Analysis of Cross-Linking in Mussel Protein Glue. Archives of Biochemistry and Biophysics 1993, 302, (1),255-258.

International Search Report, PCT/US2008/050721, (2008).

Non-Final Rejection dated Oct. 6, 2006 (U.S. Patent No. 7,618,937, issued on Nov. 17, 2009).

Final Rejection dated Apr. 18, 2007 (U.S. Patent No. 7,618,937, issued on Nov. 17, 2009).

Non-Final Rejection dated Apr. 30, 2008 (U.S. Patent No. 7,618,937, issued on Nov. 17, 2009).

Non-Final Rejection dated Apr. 9, 2007 (U.S. Appl. No. 11/068,298, filed on Sep. 28, 2005).

Non-Final Rejection dated Nov. 25, 2008 (U.S. Appl. No. 11/068,298, filed on Sep. 28, 2005).

Non-Final Rejection dated May 27, 2009 (U.S. Appl. No. 11/068,298, filed on Sep. 28, 2005).

Final Rejection dated Jul. 9, 2010 (U.S. Appl. No. 11/068,298, filed on Sep. 28, 2005).

Non-Final Rejection dated Dec. 14, 2004 (U.S. Appl. No. 10/199,960, filed Jul. 19, 2002).

Online-Medical Dictionary. "Amino acid". http://cancerweb.ncl.ac.uk/cgi-bin/omd?query=amino+acid. Nov. 13, 1997 (complete reference available online).

International Search Report (International Patent Application No. PCT/PCT/US2009/052470, filed Jul. 31, 2009).

Chongsiriwatana, N.P., et al., "Peptoids that Mimic the Structure, Function, and Mechanism of Helical Antimicrobial Peptides", PNAS, Feb. 26, 2008, vol. 105, No. 8, pp. 2794-2799.

Statz, A.R. et al., "Surface-Immobilized Antimicrobial Peptoids", Biofouling, Aug. 8, 2008, vol. 24, No. 6, pp. 439-448.

* cited by examiner $$X(F) = N_s \left( \frac{L_{ll}}{e^{\frac{\Delta G}{k_bT}}+1} + \frac{L_{ug}}{e^{\frac{\Delta G}{k_bT}}+1} \right) \bullet \left( \coth\left(\frac{Fl_k}{k_bT}\right) - \frac{k_bT}{Fl_k} \right) + N_s \frac{F}{K_s}$$

POLYMERIC COMPOSITIONS AND RELATED METHODS OF USE

CROSS-REFERENCE TO RELATED APPLICATIONS

This application claims priority benefit from U.S. Ser. No. 60/586,742 filed Jul. 9, 2004 and is a continuation-in-part of U.S. Ser. No. 11/068,298 filed Feb. 28, 2005, which was a continuation in part of U.S. Ser. No. 10/199,960 filed Jul. 19, 2002, now abandoned, which claimed priority to U.S. Ser. Nos. 60/306,750 and 60/373,919 filed, respectively, on Jul. 20, 2001 and Apr. 19, 2002, and claimed priority to U.S. Ser. No. 60/548,314 filed Feb. 27, 2004 and U.S. Ser. No. 60/549,259 filed Mar. 2, 2004. Each application is incorporated herein by reference in its entirety.

STATEMENT REGARDING FEDERALLY SPONSORED RESEARCH OR DEVELOPMENT

This invention was made with government support under Grant Nos. DE13030, DE12599 and DE14193, awarded by National Institutes of Health and Grant No. NCC-1-02097 awarded by National Aeronautics and Space Administration. The government has certain rights in this invention.

BACKGROUND OF THE INVENTION

Mussel adhesive proteins (MAPs) are remarkable underwater adhesive materials that form tenacious bonds between mussels and the surfaces upon which the mussels reside. During the process of attachment to the surfaces, MAPs are secreted as fluids that undergo a crosslinking or hardening reaction which leads to the formation of a solid plaque. One of the unique features of MAPs is the presence of L-3,4-dihydroxyphenylalanine (DOPA), an unusual amino acid which is believed to be at least partly responsible for adhesion to substrates through mechanisms that are not fully understood. Mussels adhere to a variety of surfaces, including metal, metal oxide, polymers, plastics, and wood.

Control of cell and protein adhesion on surfaces is critical to the performance of biosensors, medical diagnostic products, any instrumentation and assays used requiring handling serum and other human/animal fluids, tissue engineering, localized in vivo drug delivery, implanted medical devices, healing of surgical incisions, adhesion of tissues such as bone and cartilage for healing, and nanotechnology (nanoparticle-based therapies and diagnostic tools). In many industrial applications, control of cellular and protein adhesion to surfaces is also important. Such applications include prevention of mussel attachment to boats and ships, piers, and other structures used in oceans and fresh water, prevention of algal and bacterial growth on water lines used for industrial and drinking water, and sensors used to measure water quality and purity.

In the medical arena, the physical or chemical immobilization of poly(alkylene oxides) (PAO), such as polyethylene glycol (PEG), polypropylene oxide (PPO), polyethylene oxide (PEO), and PEO-PPO-PEO block copolymers, such as those available under the PLURONICS brand name, and polymers such as PEG/tetraglyme, poly(methoxyethyl methacrylate) (PMEMA), and Poly(methacryloyl phosphatidylcholine) (polyMPC) (E. W. Merrill, *Ann. NY Acad. Sci.*, 516, 196 (1987); Ostuni et al., *Langmuir* 2001, 17, 5605-20, which are incorporated herein by reference) on surfaces has been employed as strategy to limit the adsorption of proteins and cells on surfaces. The methods currently employed to modify surfaces with polymers must be tailored for each type of material, and therefore require different chemical strategies. For example, noble metal surfaces, such as platinum, silver, and gold, can be modified using thiol (—SH) containing molecules, whereas metal oxides are often modified using silane coupling chemistry. No surface modification strategy exists that can be universally applied to different classes of materials. Moreover, many of the current methods rely on expensive instrumentation, complex synthetic procedures, or both.

SUMMARY OF THE INVENTION

The present invention are compositions which function e.g., as an adhesive, in a substantially aqueous environment. The preferred compositions generally comprise an adhesive moiety and a polymer moiety, the polymer moiety having a desired surface active effect (or other desired characteristics). Methods of use, including atom surface-initiated transfer, radical polymerization (SI-ATRP or ATRP) are also included.

In one aspect, the adhesive moiety of a composition of this invention comprises dihydroxyphenyl derivatives including, di (DHPD) wherein a second DHPD can be

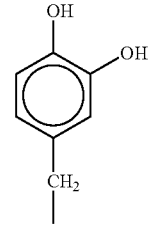

i.e., a methylene derivative of dihydroxy phenyl. In yet a further aspect, the polymer moiety comprises poly (alkyleneoxide). In a very preferred practice, the adhesive moiety comprises DHPD, e.g., DOPA (discussed herein), and the polymer moiety comprises PEO-PPO-PEO block polymers (also discussed herein).

In a further preferred practice the adhesive moiety comprises DHPD including a pendent chain comprising ethylenic or vinylic unsaturation such as, for example, an alkyl acrylate.

In yet a further aspect, the present invention comprises a method of surface modification using an approach often referred to as atom transfer radical polymerization (ATRP). Such a method can involve utilization of a DHPD-mimetic polymerization initiator capable of adsorbing or coupling to the material surface to be modified and initiating polymer growth from the surface via the initiator. In one practice the polymerization initiator is DOPA-mimetic. ATRP utilizes alkyl halide compounds to initiate a transition metal catalyzed polymerization. ATRP can be referred to as a "living" polymerization technique capable of producing homopolymers and block copolymers with well-defined molecular weights and low polydispersity.

Components of the present initiators can comprise a DHPD-containing, e.g., DOPA-containing, peptide or a catechol moiety, that is linked or coupled via a hydrolytically stable bond or sequence to an alkyl halide compound. The catecholic moiety can provide linkage to a surface or substrate with a surface to be modified, whereas the alkyl halide can permit ATRP from the adsorbed molecule. Two such components can be linked or coupled via an amide or other stable linkage or bond sequence, providing robust and water-resistant coupling and surface modification. ATRP synthesis of a large variety of polymer structures and compositions can then be performed in aqueous medium and/or media substantially without organic solvents from the surface-bound initiator. Subsequent linkage of a polymer (e.g., without limitation, PEG) provides a surface highly water resistant due to the use of such a catecholic moiety component of the water resistant MAPs.

DETAILED DESCRIPTION OF CERTAIN EMBODIMENTS

This invention can comprise dihydroxyphenyl derivative (DHPD) adhesive compound of formula (I):

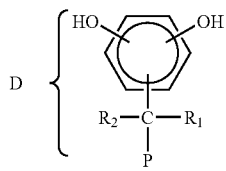
(I)

wherein
$R_1$ and $R_2$ may be the same or different and can be independently selected from hydrogen, saturated and unsaturated, branched and unbranched, substituted and unsubstituted $C_1$ to about $C_4$ hydrocarbon;
P can be separately and independently selected from —$NH_2$, —COOH, —OH, —SH,

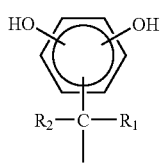

wherein $R_1$ and $R_2$ are defined above.
a single bond, halogen,

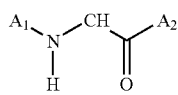

wherein $A_1$ and $A_2$ can be separately and independently selected from H, a single bond;
a protecting group,
substantially poly(alkyleneoxide),

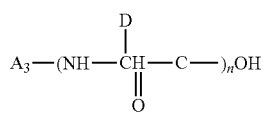

wherein n ranges from 1 to about 3 and $A_3$ is

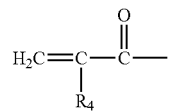

$R_4$ is H, ranges from C to about $C_6$ lower alkyl, or

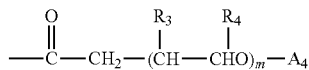

$R_3$ is defined as above, and D is indicated in Formula (I).
In one aspect the poly(alkylene oxide) can have the structure

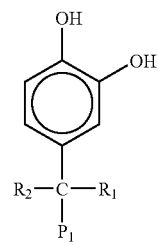

wherein R3 and R4 can be separately and independently H, or CH3 and m can have a value in the range from 1 to about 250, $A_4$ is NH2, COOH, —OH, —SH, —H or a protecting group.

In a very preferred form, DHPD can be

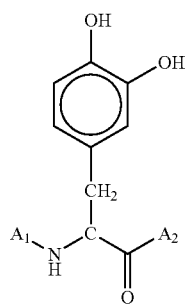

$R_1$, $R_2$, and P being defined as above.
In a further preferred form DHPD can be of the structure:

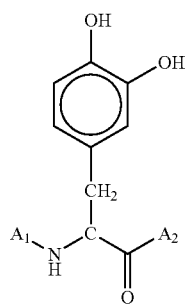

wherein $A_2$ can be —OH and $A_1$ is substantially poly(alkylene oxide) of the structure

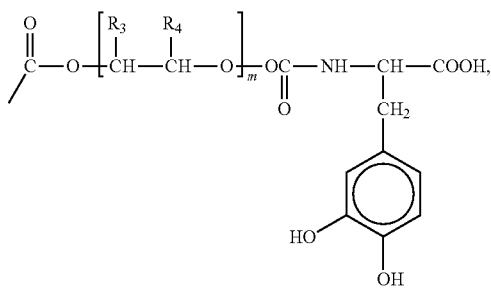

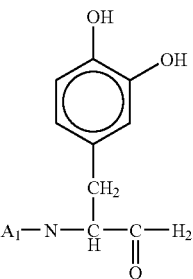

wherein $A_1$ and $A_2$ are defined above.

"Substantially poly(alkylene oxide)" as used herein shall mean predominantly or mostly alkyloxide or alkyl ether in composition. This definition contemplates the presence of heteroatoms e.g., N, O, S, P, etc. and of functional groups e.g., —COOH, —NH$_2$, —SH, as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, or of this polymer.

$R_3$, $R_4$ and m being defined as in claim 2. Generally speaking the poly(alkylene oxide) can be a block copolymer of ethylene oxide and propylene oxide.

A method of this invention can involve adhering substrates to one another comprising providing a DHPD of the structure:

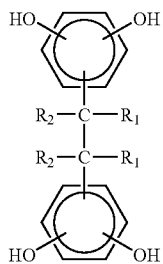

wherein $R_1$ and $R_2$ can be defined as above; applying a DHPD of the above structure to one or the other or both of the substrates to be adhered; contacting the substrates to be adhered with the DHPD of the above structure therebetween to adhere the substrates to each other, and optionally repositioning the substrates relative to each other by separating the substrates and recontacting them to each other with the DHPD of the above structure therebetween.

In a preferred method, $R_1$ and $R_2$ can be hydrogen.

Definition: Dihydroxyphenyl derivatives (DHPD) for purposes of this application shall mean dihydroxyphenyl derivatives of the following structure:

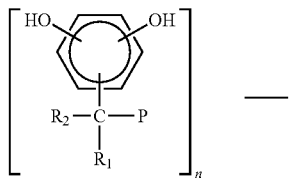

wherein P, $R_1$ and $R_2$ are defined below and n ranges from 1 to about 5. In one practice, $R_1$ and $R_2$ can be hydrogen and P is, itself, dihydroxy phenyl. A preferred DHPD in a practice of the present invention is 1-3,4, dihydroxy phenyl alanine (DOPA), (generically),

Figure 1:
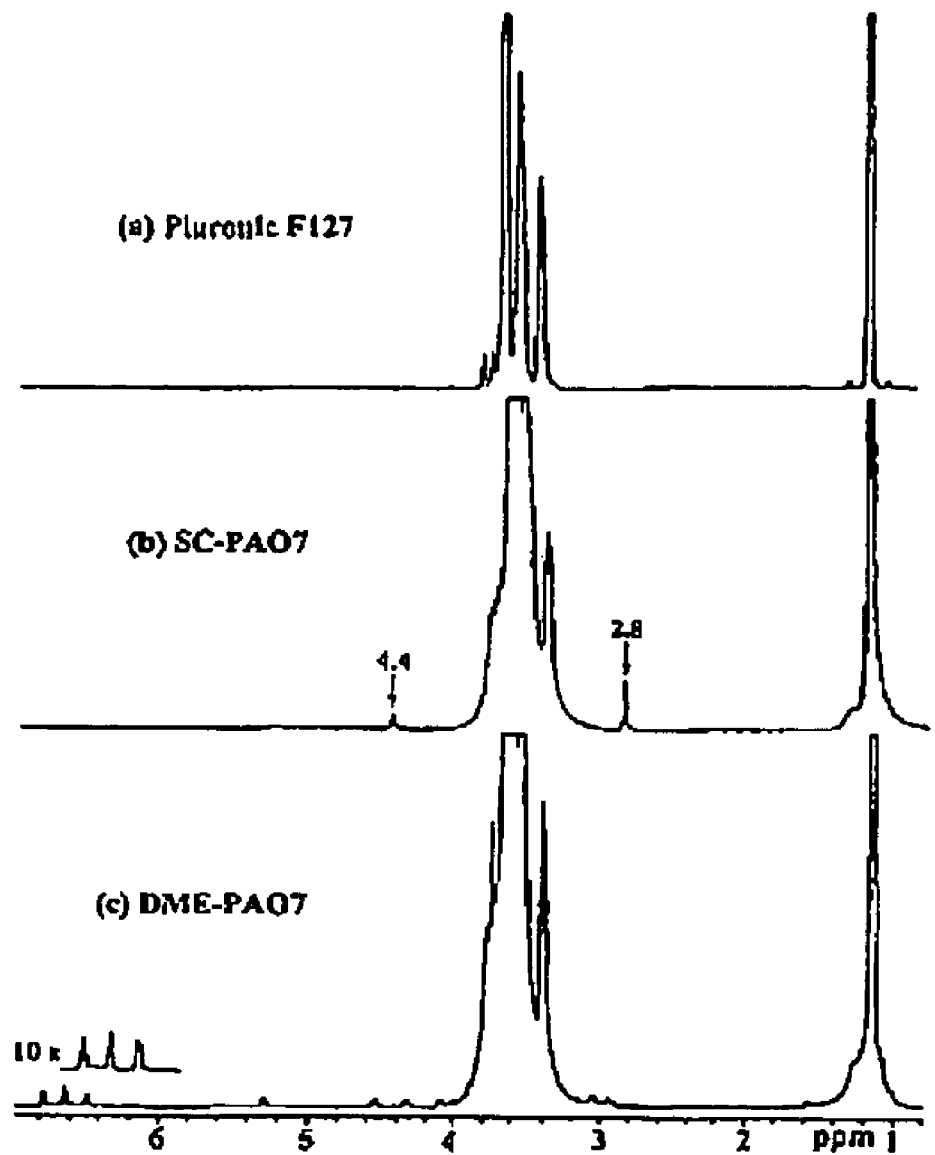
FIG. 1 shows $^1$H NMR spectra of PLURONIC® F127, its carbonate intermediate (SC-PAO7) and DME-PAO7 in CDCl$_3$.

These dihydroxyphenyl derivative ("DHPD") adhesives function in an aqueous environment. To form the polymeric composition, a DHPD moiety which generally provides adhesive functionality coupled to a polymer which provides the desired surface active effect. These components will be described in more detail below.

These adhesives and polymeric compositions have many uses, including prevention of protein and/or cell adhesion to a surface in various medical, industrial and consumer applications. The DHPD adhesives can also be used as substitutes for sutures for a wound and as aids in healing bone fractures or cartilage-to-bone damage. These and other uses will be described in more detail below.

The preferred polymer compositions of the present invention have the following structure:

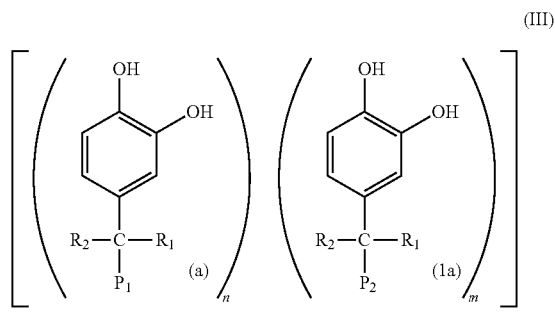

wherein, for each compound of formula (1a), $R_1$ and $R_2$ are defined separately and independently as above, $P_1$ and $P_2$ are separately and independently defined as P in formula (I);

n and m are independently ranger from 0 to about 5, provided that at least one of n or m is at least 1;

Adhesive Moiety

The adhesive moiety of the present invention is a dihydroxyphenyl derivative ("DHPD") having the following preferred structure:

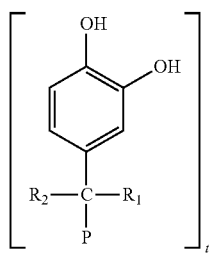

wherein $R_1$, $R_2$ and P are defined above and t ranges between 1 and about 10, preferably about 1 to about 5 and most preferably 1 to about 3. The DHPD adhesive can function in an aqueous environment. In this context, an aqueous environment is any medium comprising water. This includes without limitation water, including salt water and fresh water, cell and bacterial growth media solutions, aqueous buffers, other water-based solutions, and body fluids. The DHPD moiety can be derivatized. As would be understood by those skilled in the art, such derivatization is limited by the retention of the desired adhesive characteristic.

Polymeric Component

Various polymeric components providing a surface active effect and other desired characteristics will be well-known to those skilled in the art made aware of this invention. The desired surface active effect relates to reduced particulate agglomeration and anti-biofouling, including resistance to cell and/or protein adhesion. For instance, the polymer component can be water soluble, depending upon end-use application, and/or capable of micelle formation depending upon various other end-use applications. Polymers useful in the present invention include, but are not limited to, polyethylene glycol (PEG), polyethylene oxide (PEO), polypropylene oxide (PPO), PEO-PPO-PEO block copolymers, polyphenylene oxide, PEG/tetraglyme, PMEMA, polyMPC, and perfluorunated polyethers.

The polymeric compositions can be synthesized in several ways. For example, the polymeric compositions may be synthesized through a general synthetic procedure for polymer end-group activation. Various polymers or monomeric components thereof can be activated using carbonate chemistry. In particular, a succinimidyl carbonate-activated polymeric component reacted with DHPD moiety can provide a stable urethane conjugate. Two of the many possible pathways (a) and (b) in Scheme 1a and 1b, below, show coupling with a poly(alkylene oxide) in either aqueous or non-aqueous solvents, without compromising desired bioadhesion. For instance, a DHPD residue can be coupled to a polymeric component to provide the desired conjugate composition, through either urethane or amide bond formation. These synthetic counts are shown in Scheme 1a and 1b which are discussed in greater detail below.

SCHEME 1a

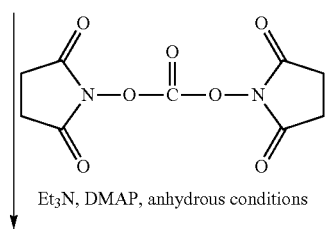

-continued
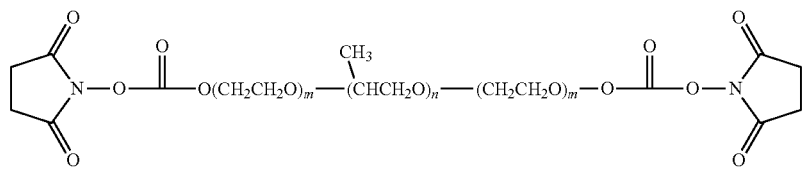
SC-PAO7 m = 100, n = 65
SC-PAO8 m = 78, n = 30
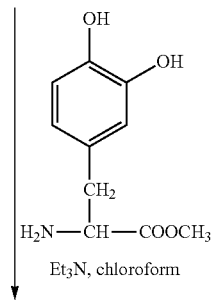
Et$_3$N, chloroform
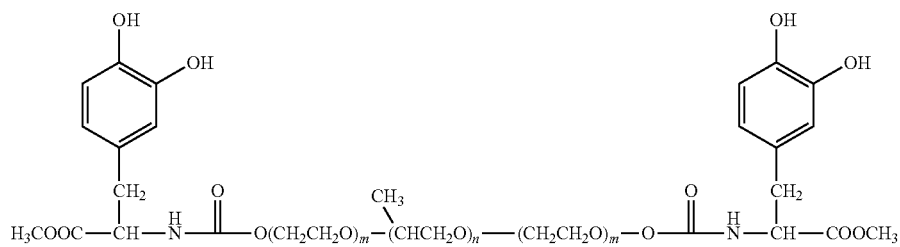
DME-PAO7 m = 100, n = 65
DME-PAO8 m = 78, n = 30
SCHEME 1b
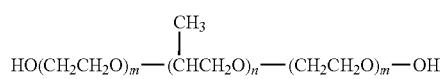
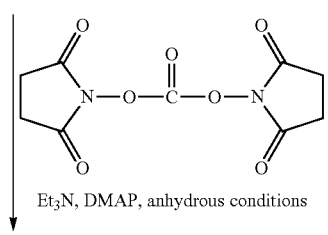
Et$_3$N, DMAP, anhydrous conditions -continued

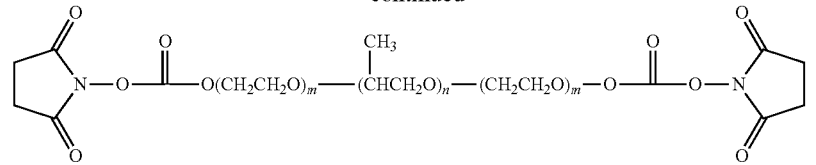

SC-PAO7 m = 100, n = 65
SC-PAO8 m = 78, n = 30

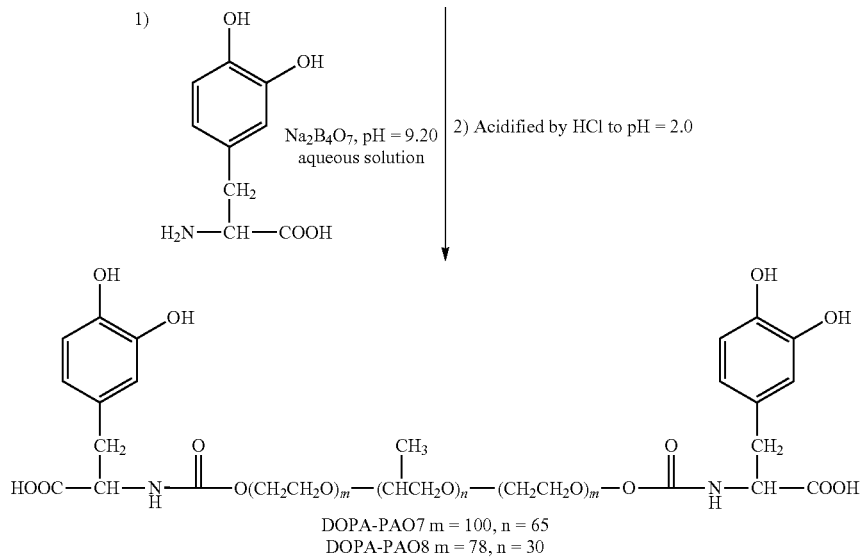

DOPA-PAO7 m = 100, n = 65
DOPA-PAO8 m = 78, n = 30

More particularly, if coupled to the polymeric component via urethane bond formation, a carboxylic acid group of the DHPD component can be esterified or derivatized with various other functional groups. Alternatively, the DHPD component can be coupled to a polymeric component (e.g., amidation or esterification depending on polymer end group, $-NH_2$ or $-OH$) providing a DHPD functionality which can be derivatized by any of numerous known protecting groups, including without limitation Boc, Fmoc, borate, phosphate, and tributyldimethylsilyl. N-group protection of a DHPD component can leave the carboxylic acid group available for multi-functional derivatization and/or a higher density of polymeric components conjugated therewith.

Accordingly, in part, the present invention is also a method of using urethane synthesis to incorporate a DHPD residue into a polymeric system. Such a method includes (1) providing a polymeric component terminating in a plurality of monomers, each having a functional end group; (2) preparing a carbonate derivative of the polymeric component; and (3) preparing a urethane moiety upon reaction of the carbonate derivative and at least one DHPD moiety. As described above, a polymeric component utilized in conjunction with this method can include those having terminal monomeric functionality reactive with a reagent providing the desired carbonate derivative and, ultimately, providing a urethane moiety coupling the polymeric and DHPD components. Various other coupling reagents and/or hydroxy-terminating polymeric components can be used to provide the desired urethane moiety.

In part, the present invention is also a method of using a carbonate intermediate to maintain catecholic functionality of a DHPD-incorporated polymeric composition and/or system, or to otherwise enhance the adhesion properties thereof. Such a method includes (1) providing a polymeric component terminating in a plurality of monomers each having a functional end group; (2) reacting the polymeric component with a reagent to provide a carbonate intermediate; and (3) reacting the carbonate intermediate with at least one DHPD moiety. Without limitation to any single theory or mode of operation, this inventive method can be considered a way of enhancing the reactivity of the polymeric component end group, via a suitable carbonate intermediate. Subsequent reaction at the amino-nitrogen of DHPD moiety provides the corresponding conjugate while maintaining catecholic functionality.

In accordance with this invention, as demonstrated in Scheme 1a, various synthetic routes can be used to couple DHPD moieties to such carbonate activated intermediates. DOPA methyl ester (DME), prepared by the reaction of DOPA with methanol in the presence of thionyl chloride, can be used in organic solvents. Reaction progress can be monitored by TLC and NMR, with the coupling reaction virtually complete in one hour (with representative conjugates DME-PAO7 (from PAO PLURONIC® F127) and DME-PAO8 (from PAO PLURONIC® F68)). High product yields were obtained upon purification from cold methanol.

The free carboxylic form of DOPA can be coupled with the carbonate intermediate in alkaline aqueous solution. It is well known that the chief difficulty in working with DOPA is its ease of oxidation (to DOPA-quinone and other products), which readily occurs in alkaline aqueous solutions. To prevent unwanted oxidation of DOPA catechol side chains during coupling under alkaline conditions, a borate-protected DOPA can be first formed by adding DOPA to aqueous sodium borate (Scheme 1b). The resulting complex is remarkably stable in neutral or alkaline solutions, and can be readily deprotected under acidic conditions. Taking advantage of complexation between DOPA and borate, DOPA was coupled to the ends of several commercially-available PAOs under alkaline aqueous conditions to yield DOPA-PAO7 and DOPA-PAO8. Visual inspection of the reaction solution revealed the absence of strongly absorbing DOPA-quinone, an indication that DOPA remains unoxidized during the reaction. At the completion of the reaction, acidification with HCl resulted in deprotection of the DOPA endgroups of the block copolymer.

Both $^1$H NMR spectra and colorimetric assay confirmed the compositions of the succinimidyl activated reaction intermediates and all four DOPA-modified PAOs of Scheme 1. Shown in FIG. 1 are $^1$H NMR spectra of PAO PLURONIC® F127, the succinimidyl carbonate activated intermediate (SC-PAO7), and the corresponding DOPA methyl ester modified PAO (using PLURONIC® F127, DME-PAO7). The sharp peaks at ~2.8 ppm due to the —CH$_2$— protons from the succinimidyl carbonate group and at ~4.4 ppm due to the —CH$_2$—O— protons from the only ethylene oxide group adjacent to the carbonate group in activated-PAO completely disappear from the $^1$H NMR spectra of the DOPA-containing PAO, whereas a series of new peaks appear due to the introduction of DOPA moieties into the copolymers. One characteristic feature of the $^1$H NMR spectra of the DOPA-containing PAO is the appearance of one singlet and two doublets in the range of 6.5-6.9 ppm corresponding to the three protons on the DOPA phenyl ring. Similar features were also observed in the $^1$H NMR spectrum (not shown) of the DOPA-PAO conjugate synthesized from aqueous solution.

Based on the assumption of two available succinimidyl carbonate groups in the corresponding carbonate intermediates, SC-PAO7 and SC-PAO8, coupling efficiencies of DOPA methyl ester and DOPA to these two PAOs were quantitatively found to be in the range from 76% to 81% as obtained from calorimetric analysis (Table 1). The reported coupling efficiencies are the average values of at least three repeated syntheses performed under the same conditions and were not found to increase significantly when a larger excess of DOPA was used in the reaction. Similar coupling efficiencies were also found for DOPA-PAO7 and DOPA-PAO8 made from aqueous solutions, suggesting that the hydrolysis of succinimidyl carbonate activated PAOs is slow in the aqueous alkaline solution containing Na$_2$B$_4$O$_7$.

In contrast to coupling efficiencies, the product yields (shown in Table 1) of selected DOPA-modified PAOs synthesized in aqueous solution were found to be lower than those synthesized in organic solvent. This may be due to the surfactant properties of the starting PAO material, causing the low efficiency of extraction of DOPA-modified PAO with dichloromethane from water. It should be noted that the free carboxylic acid in DOPA-PAO7 and DOPA-PAO8 can be further functionalized using standard peptide chemistry to tailor the properties of the block copolymers. The four DOPA-modified PAOs of Table 1 could be stored at −20° C. indefinitely with no discoloration or change in properties.

TABLE 1

Coupling efficiency and product yield of DOPA modified PLURONIC ®

|  | Coupling Efficiency (%)* | Product Yield (%) |
| --- | --- | --- |
| DME-PAO7 | 78.0 ± 4.0 | 75.0 ± 5.0 |
| DOPA-PAO7 | 80.0 ± 4.0 | 52.0 ± 3.0 |
| DME-PAO8 | 76.0 ± 2.0 | 76.0 ± 4.0 |
| DOPA-PAO8 | 81.0 ± 2.0 | 49.0 ± 2.0 |

*Determined by colorimetric analysis as taught by Waite and Benedict (Waite, J. H. & Benedict, C. V. Assay of dihydroxyphenylalanine (dopa) in invertebrate structural proteins. Methods in Enzymology 107, 397–413 (1984), which is incorporated herein by reference).

Control of cell and protein adhesion on surfaces is critical to the performance of biosensors, medical diagnostic products, any instrumentation and assays used requiring handling serum and other human/animal fluids, tissue engineering, localized in vivo drug delivery, implanted medical devices, healing of surgical incisions, adhesion of tissues such as bone and cartilage for healing, and nanotechnology (nanoparticle-based therapies and diagnostic tools). In many industrial applications, control of cellular and protein adhesion to surfaces is also important. Such applications include without limitation prevention of mussel attachment to boats and ships, piers, and other structures used in oceans and fresh water, prevention of algal and bacterial growth on water lines used for industrial and drinking water, and sensors used to measure water quality and purity.

The polymeric compositions of the present invention can be used as coatings to prevent protein and cellular adhesion to devices for medical and research applications. These include without limitation such uses as coatings for medical implants, coatings for surgical devices, coatings for devices that handle serum and other animal or human derived materials, medical diagnostic devices, and biosensors. Alternatively, the polymeric compositions can be tissue adhesive polymeric hydrogels for medical uses such as tissue sealants, gels for prevention of surgical adhesion (scar tissue formation), bone and cartilage adhesives, tissue engineering, and site specific drug elution and for research uses such as immobilization of proteins including antibodies and small molecule analytes including pharmaceuticals. In addition, there are various industrial and consumer product uses of these coatings and hydrogels including without limitation prevention of marine biofouling (attachment of algae, bacteria, and mussels to surfaces underwater), prevention of bacteria contamination of water streams to industrial plants such as electronic and drug manufacturers, prevention of bacterial contamination of drinking water streams, dental and denture adhesives, underwater adhesives to deliver indicators, coatings for water purity and measurement sensors, paints used for prevention of biofouling, and use in cosmetics to adhere desired fragrances and colorants to hair, eyelids, lips, and skin, to form temporarily skin coloring such as tattoos and the like, and for resealable adhesives for consumer products such as storage bags. The present methods can be used to prepare a variety of polymer modified surfaces for both medical (diagnostics, devices, nanoparticle-based therapies) and nonmedical (paints and other particle dispersions, MEMS, quantum dots, nonfouling surfaces) technologies.

Adhesive hydrogels can be also formed using the present methods. The DHPD adhesive is attached to polymers capable of forming a hydrogels in vivo or in vitro. These hydrogels can be formed by a number of methods including the use of self-assembling polymers that form gels at higher temperatures such as normal human body temperatures, the use of polymers that can be cross-linked by an enzymatic reaction, the use of polymers that can be subjected to oxidation to form cross-linked hydrogels, and the use of polymers that can be subjected to photoactivation to produce cross-linked hydrogels.

Anti-Biofouling Coatings

The anti-biofouling coatings of the present invention may be applied to medical devices, such as vascular or arterial stents, pacemakers, heart valves, glucose monitors and other biosensors, vascular wraps, defibrillators, orthopedics devices, and surgical devices, including sutures and catheters. The polymeric compositions of the present invention can be used as coatings to prevent protein and/or cellular adhesion to a device for medical and research applications. These include without limitation such uses as coatings for medical implants, coatings for surgical devices, coatings for devices that handle serum and other animal or human derived materials, medical diagnostic devices, and biosensor. Among the challenges in modifying biomaterial surfaces with polymers for cell adhesion resistance are producing a sufficiently high density of polymer capable of repelling proteins and cells and producing a coating that cover the surface completely. This is particularly a problem with devices containing multiple components made of different materials. A surface may be modified by the polymeric composition of the present invention in any number of ways. For example, the polymeric composition may be absorbed onto the surface or a DHPD moiety containing a polymerization initiator may be adsorbed onto the surface and polymer growth initiated from the surface. With the latter, a number of polymerization techniques are possible, including without limitation surface initiated atom transfer radical polymerization (SI-ATRP), radical polymerization methods, ionic polymerization, ring-opening polymerization, and photopolymerization.

The ATRP method of this invention exploits a biological strategy that mimics key components of natural adhesive proteins. The synthesis of a new bifunctional initiator, described below, comprises an adhesive moiety coupled to a functional group capable of initiating polymer growth. The initiator can be used to modify a variety of surfaces with polymers of variable composition and properties.

A surface or substrate surface modification method of this invention comprises: 1) immobilizing an initiator onto the surface to be modified by adsorption e.g., from a solution; 2) growing a polymer by surface-initiated polymerization from using the adsorbed initiator e.g., a monomer-containing solution to complete the modification. The resulting surface-bound polymer has nonfouling properties, such as by providing steric resistance to fouling of the modified surfaces by cells, proteins, and other particles. SI-ATRP of this invention can be used to prepare a variety of polymer modified surfaces for both medical (diagnostics, devices, nanoparticle-based therapies) and nonmedical (paints and other particle dispersions, MEMS, quantum dots, nonfouling surfaces) technologies. The water-resistant properties of the anchoring component are useful for permanent attachment of polymer coatings in aqueous environments. The biomimetic anchor may also have anticorrosive properties for metallic surfaces. A schematic ATRP polymerization reaction follows:

The term "Adsorption" used above is to be broadly construed to include any and all interactions of sufficient strength to create the desired surface modification.

By utilizing the unique solubility properties of PEG, the surface density of polymer can be increased by treating surfaces with PEG solutions near the lower critical solution temperature (LCST), or cloud point. While not wanting to be bound by any theory, applicants believe that under the high ionic strength and elevated temperature conditions used in the present invention, PEG molecules have a reduced hydrodynamic radius, which in principle allows a higher density of PEG chains to pack on a surface than under standard conditions. This approach is useful for polymers that show inverse solubility transitions at high temperature and high ionic strength, such as poly(ethylene glycol), poly(N-isopropylacrylamide) and other N-substituted poly(acrylamides) that show inverse solubility transitions.

By modifying surfaces with various polymeric compositions of the present invention, resistance to cell and protein attachment is conferred for up to 7 days, 14 days, 21, days, 30 days, 60 days, 90 days and 120 days or longer. The number of DHPD moieties in the adhesive component and the pH of the modification buffer are responsible for most of the variation in the cell and/or protein adhesion resistance of the modified materials. For those surfaces that are modified by adsorption, adsorption time and polymeric composition concentration contributes little to the variation in cell and/or protein adhesion resistance of the modified materials. The greater the number of DHPD moiety monomers in the adhesive component, the better the cell and/or protein adhesion resistance. The density of the polymeric composition on the surface correlates well with resistance to cell and/or protein adhesion. The thickness of the coating layer can be from about 20 Å to about 100 μm, including 30 Å, depending on the polymer composition used and the pH of the modification buffer.

The concentration of the polymer composition used for modification of a surface can be from about 0.1 mg/ml to about 75 mg/ml. The pH of the modification buffer can be from about 3 to about 9. The modification time can be from about 10 minutes to about 72 hours. The temperature of the modification can be from about 25° C. to about 60° C.

Figure 19:
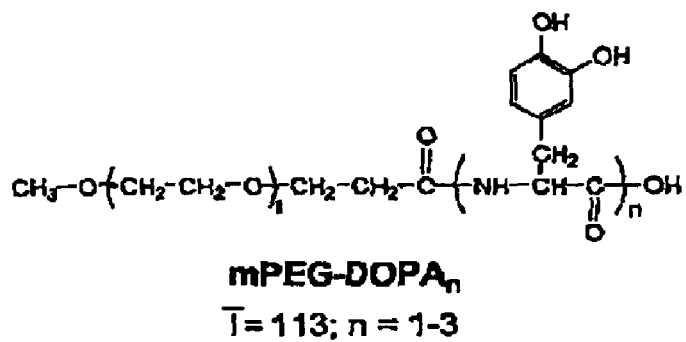
FIG. 19 (plots XPS survey scans of unmodified $TiO_2$ and $TiO_2$ treated with mPEG-DOPA$_{1-3}$.
Figure 19:
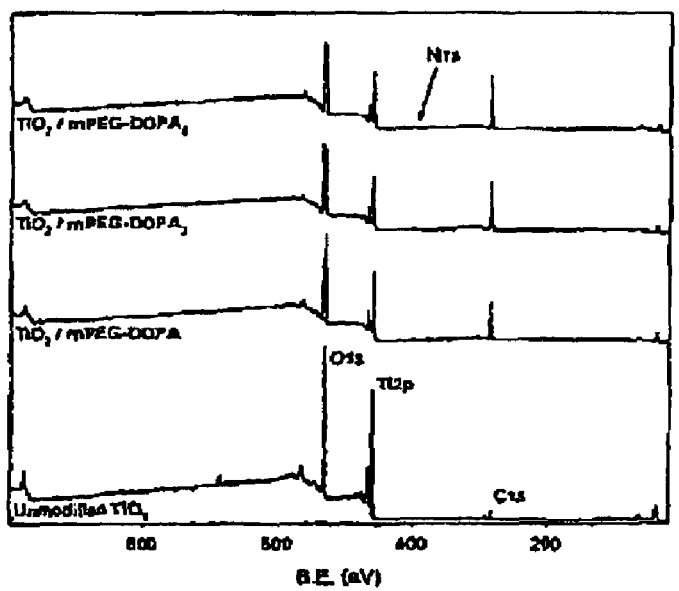

As shown in FIG. 19, XPS survey scans of unmodified $TiO_2$ revealed strong peaks at ~458 eV (Ti2p) and ~530 eV (O1s) characteristic of native oxide, as well as a small peak at 248.7 eV (C1s) as a result of adventitious hydrocarbon contamination. $TiO_2$ substrates treated with mPEG-DOPA$_{1-3}$ under cloud point conditions, however, demonstrated dramatic increases in surface-bound carbon as reflected by the C1s peak, suggesting the presence of PEG on the surface. Moreover, the increases in the C1s peaks observed after modification with mPEG-DOPA$_{1-3}$ were directly proportional to the number of terminal DOPAs present. Additionally, a small peak at 400 eV (N1s) was seen in the spectrum of the $TiO_2$ surface modified with mPEG-DOPA$_{1-3}$, representing the amide nitrogen in DOPA.

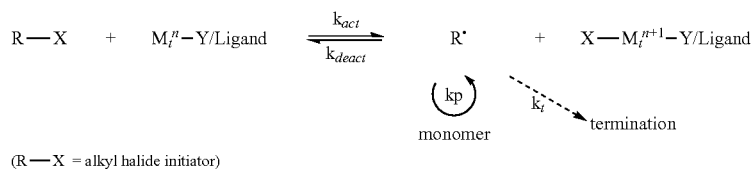

$$R-X + M_t^n-Y/Ligand \underset{k_{deact}}{\overset{k_{act}}{\rightleftharpoons}} R^\bullet + X-M_t^{n+1}-Y/Ligand$$

(R—X = alkyl halide initiator)

Quantitative analysis of the high resolution XPS data of the substrate surfaces can provide useful information on relative amounts of PEG bound to the surface. Table 2 shows the titanium, oxygen, and carbon atomic composition calculations for $TiO_2$-modified with mPEG-DOPA$_{1-3}$. The oxygen signal is further subdivided into metal oxide (Ti—O—Ti), surface hydroxide (Ti—O—H), and organic oxygen and coupled water (C—O, $H_2O$) species.

TABLE 2

Titanium, oxygen, and carbon atomic composition calculations

| | | Atomic composition[a] (wt %) | | | |
|---|---|---|---|---|---|
| | | O | | | |
| Surface | Ti | Ti—O—Ti | Ti—O—H | C—O, $H_2O$ | C |
| Unmodified $TiO_2$ | 31.0 | 47.0 | 7.1 | 3.9[b] | 11.1 |
| MPEG-DOPA | 15.5 | 24.5 | 6.2 | 14.9 | 38.9 |
| MPEG-DOPA$_2$ | 12.3 | 19.4 | 5.4 | 18.3 | 44.6 |
| MPEG-DOPA$_3$ | 11.5 | 17.3 | 4.7 | 20.6 | 45.9 |

[a]Trace amounts of N were neglected.
[b]Assumed to be water bound to the surface.

The ratio of Ti to Ti—O—Ti for all substrates differs substantially from the theoretical stoichiometry of 2.0; the difference is likely due to a sampling depth that goes beyond the depth of the surface oxide (3-4 mm). This result is expected given the Flory radius of a 5000 $M_w$ PEG (2.8 mm) and a typical XPS sampling depth of 5-10 mm. On surfaces modified with mPEG-DOPA$_{1-3}$, the Ti-to-C atomic ratio decreased dramatically with increasing DOPA peptide length, corresponding to increases in the amount of adsorbed PEG. The observed C to organic oxygen (C—O) ratio exceeds the theoretical value of 2.0 for pure PEG, which suggests that adventitious hydrocarbon contamination remains on modified surfaces. These results are shown in Table 3.

TABLE 3

Atomic ratio for adsorbed polymeric compositions

| | Atomic ratio | | |
|---|---|---|---|
| Surface | C/Ti | Ti/Ti—O—Ti | C/C—O |
| Unmodified $TiO_2$ | 0.36 | 1.51 | 2.84 |
| MPEG-DOPA | 2.51 | 1.58 | 2.62 |
| MPEG-DOPA$_2$ | 3.62 | 1.57 | 2.43 |
| MPEG-DOPA$_3$ | 4.01 | 1.51 | 2.24 |

DOPA creates strong, reversible bonds with $TiO_2$. The energy of the bond is 30.56 kcal/mol and needs about 800 pN to be detached from $TiO_2$ at the single molecule level, which is four times stronger than the interaction between Avidin and Biotin. The DOPA-$TiO_2$ strength of interaction is about midway between that of Avidin-Biotin, one of the strongest hydrogen bond based interactions in biology (0.1-0.2 nN) and a covalent bond (>2 nN).

Figure 28:
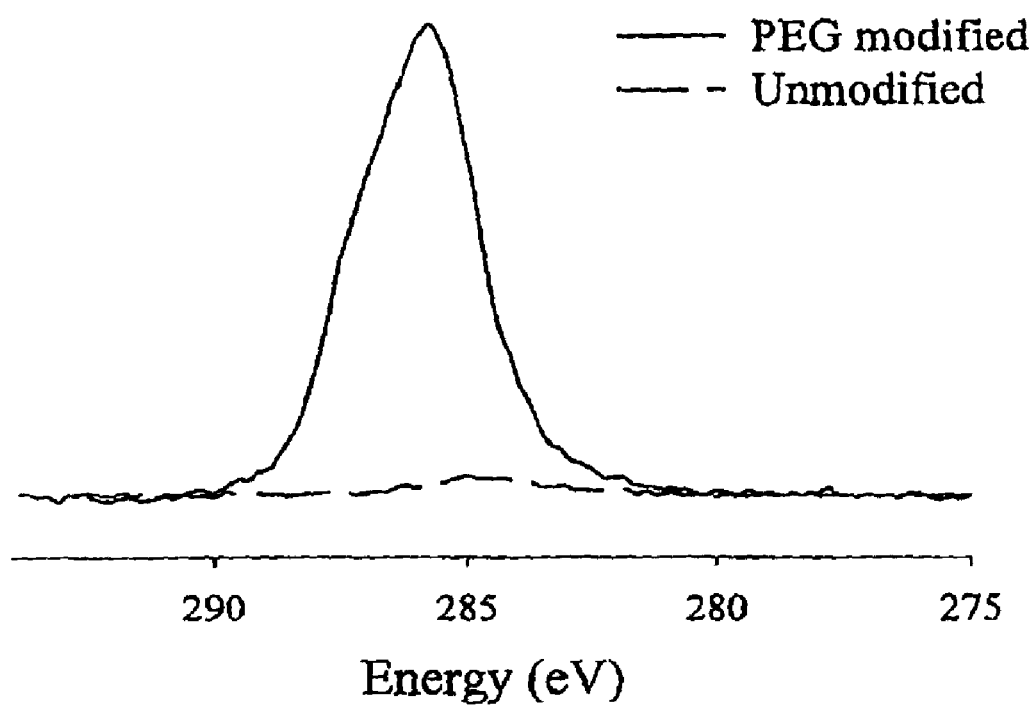
FIG. 28 X-ray Photoelectron Spectroscopy XPS analysis of a silicon nitride surface.
Figure 29:
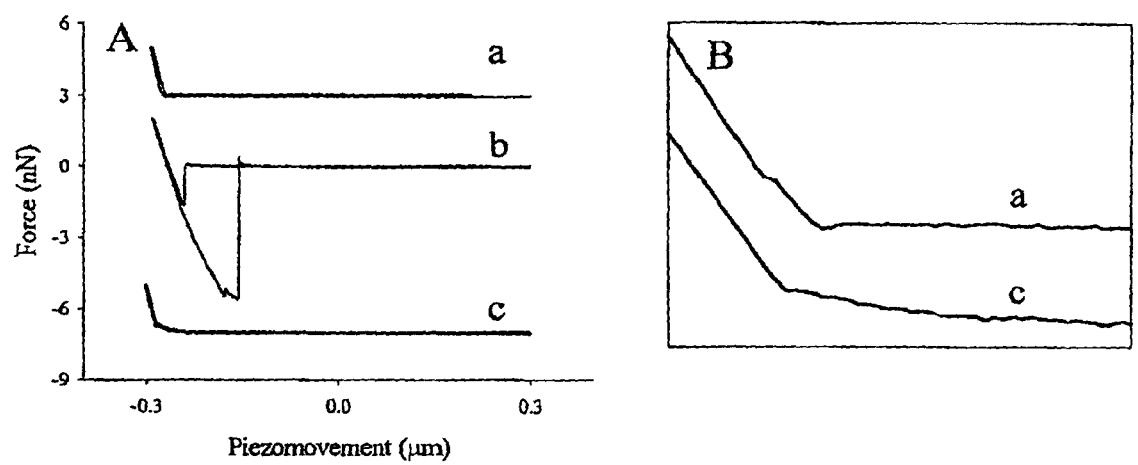
FIG. 29 is a free monitoring of functionalized silicon nitride cantilevers.
Figure 36:
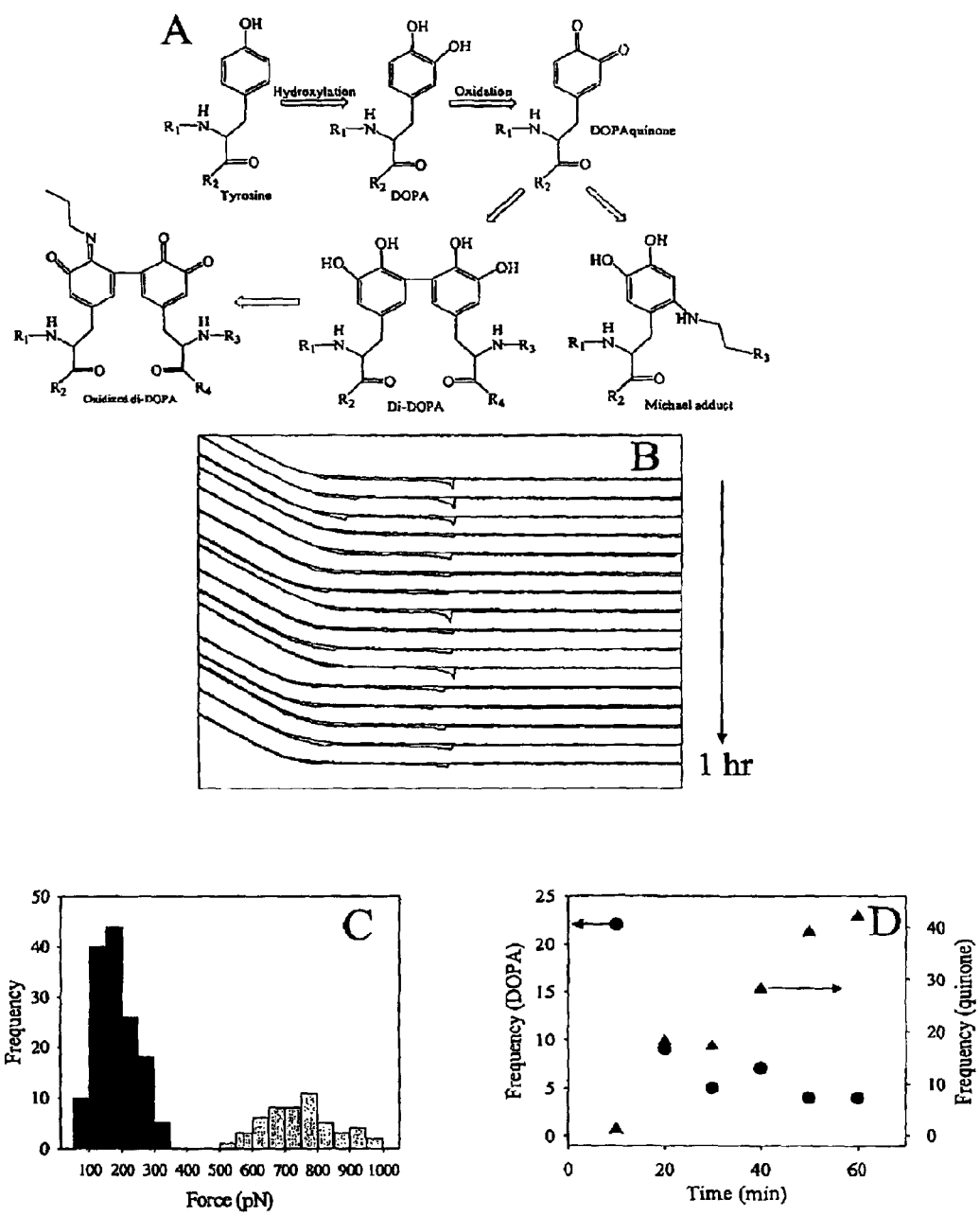
FIG. 36 is synthetic route and data analysis.

To study DOPA adhesion properly, the following conditions were used: single molecule approach, an aqueous environment, and a platform for DOPA immobilization. Atomic Force Microscopy (AFM) was chosen as a tool for the investigation which satisfies those three conditions and is sensitive enough to measure the viscoelastic properties of soft materials: protein, DNA, and synthetic polymers at a single molecule level. Amine moieties were introduced to a cantilever tip (Si3N4) and then the mixture of methoxy-poly(ethylene glycol, mPEG) and Fmoc-terminated PEG (Fmoc-PEG) derivatives were conjugated. (Boc-)DOPA was coupled to the amine groups generated by the cleavage of Fmoc (FIG. 33C). A 5~10 molar excess of mPEG to DOPA-PEG was used so that single, immobilized DOPA4 PEG could be isolated. This molecular configuration sterically hindered the molecular dynamics of DOPA-PEG, thus providing an explanation for the result of DOPA oxidation experiments later (FIG. 36). Chemical reaction steps were monitored by X-ray photoelectron spectroscopy (XPS) showing successful PEG modifications on flat silicon nitride surfaces (1×1 cm2) (FIG. 28). Chemical groups introduced onto silicon nitride tip surfaces change electrostatic properties, which are also good indicators of surface modifications (FIG. 29-A). It is important to note that the difference of approaching signals was detected between bare and modified cantilevers representing resistance force due to molecular layers (FIG. 29-B).

Figure 30:
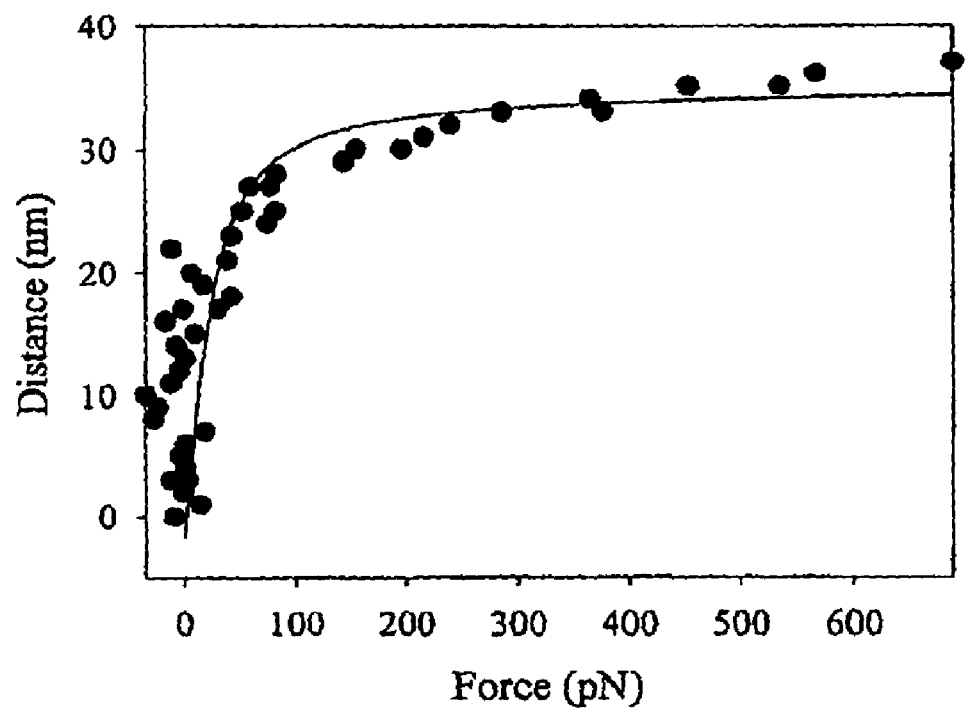
FIG. 30 is an analysis of entropic elasticity of poly(ethylene glycol).
Figure 33:
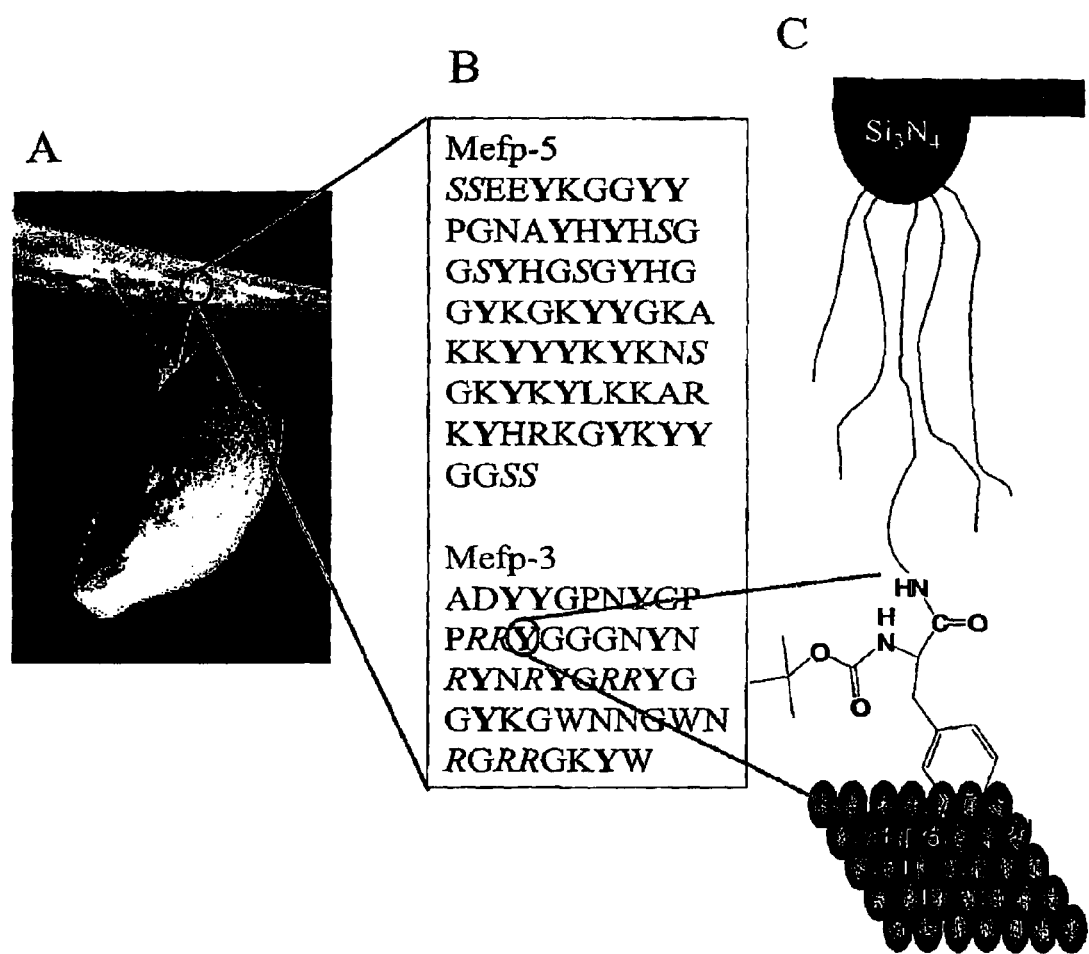
FIG. 33 is an atomic force microscopy arrangement.
Figure 34:
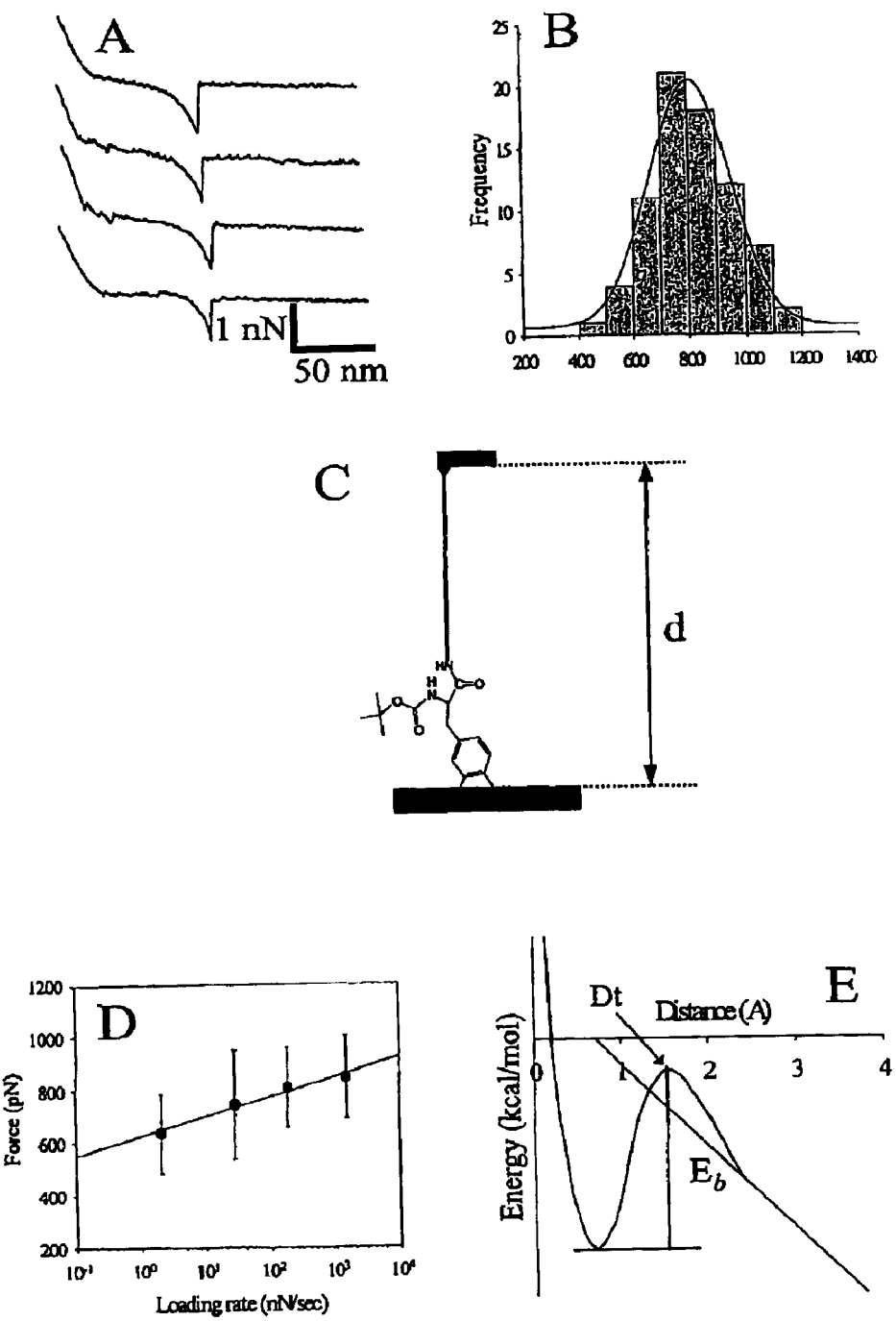
FIG. 34 is data regarding force measurement.

DOPA conjugated cantilevers displayed significant adhesion accompanied by entropic elasticity of the PEG chain (FIG. 34). A histogram of the force distribution shows a uni-modal shape indicating only single adhesive event, which is different compared to the case of a multivalent protein, Avidin12. Force-Distance (F-D) measurements were collected and a statistical analysis performed (FIG. 34, n=105). The average force was 785 pN in water at a loading rate of 180 nN/s. Most importantly, the length of stretched PEG (36 nm) was consistent with the expected contour length of a PEG molecule (37 nm, FIG. 30). These data are observing a single molecular event: monovalent binding of DOPA, polydispersity of PEGs, and tip geometry. A single DOPA was conjugated at the end of a polymer chain, to serve as one binding unit on a TiO2 surface (FIG. 33). This monovalency is different from metal-Histidine6 (Metal-(His)6) studies where tethered (His)6 provides three metal chelating sites (3× metal/(His)2)13-15. In addition, a 'mountain-tree' like configuration of PEG5 antilever can separate two different DOPA detachment signals because of polydispersity of PEGs (tree) and the spherically-shaped tip (mountain) (r=25 nm).

Defined, "d" is the z-displaced distance of piezoelectric device when a single DOPA-PEG molecule was fully stretched during retraction (FIG. 34C). The 'd' values appeared to be almost constant throughout many repeated cycles although it did vary slightly (FIG. 34A). This small variation might be due to DOPA binding to the surface at different angles. An important feature of our experiment is that the unbinding signals are epetitions using the 'identical' DOPA molecule. This is compared to the traditional approach of single molecule pulling experiments where tips picked up one molecule randomly. This also demonstrates that the DOPA adhesion chemistry was completely reversible. This reversibility led us to the conclusion that the weakest chemical linkage from substrate to tip (TiO2~Si3N4) is the Ti(surface)-O(DOPA) bond.

The result suggested that at ~0.8 nN, the DOPA-TiO2 interaction is mechanically midway between that of Avidin-Biotin, one of the strongest hydrogen bond-based interaction in biology (0.1~0.2 nN) and covalent bond (>2 nN). Energy information from force data by changing the loading rate, the amount of force applied per unit time. Changes over four orders of magnitude of a loading rate generated four different force distributions to map the energy landscape of DOPA binding. Linear-log line plot of force vs. loading rate in FIG. 34D provided binding energy and a distance after which the association is removed along the applied force direction. DOPA had an energy barrier of 28.1 kcal/mol, and the distance needed to reach the activation energy maximum was 1.27 Å (FIG. 34E).

The binding orientation of DOPA is believed to be with the two hydroxyl groups on the aromatic ring pointed down toward the surface. Therefore, the confirmation of chemical groups responsible for single molecule adhesion signals in AFM is important to exclude other binding chemistry due to different orientations. Two methods were used.

Figure 31:
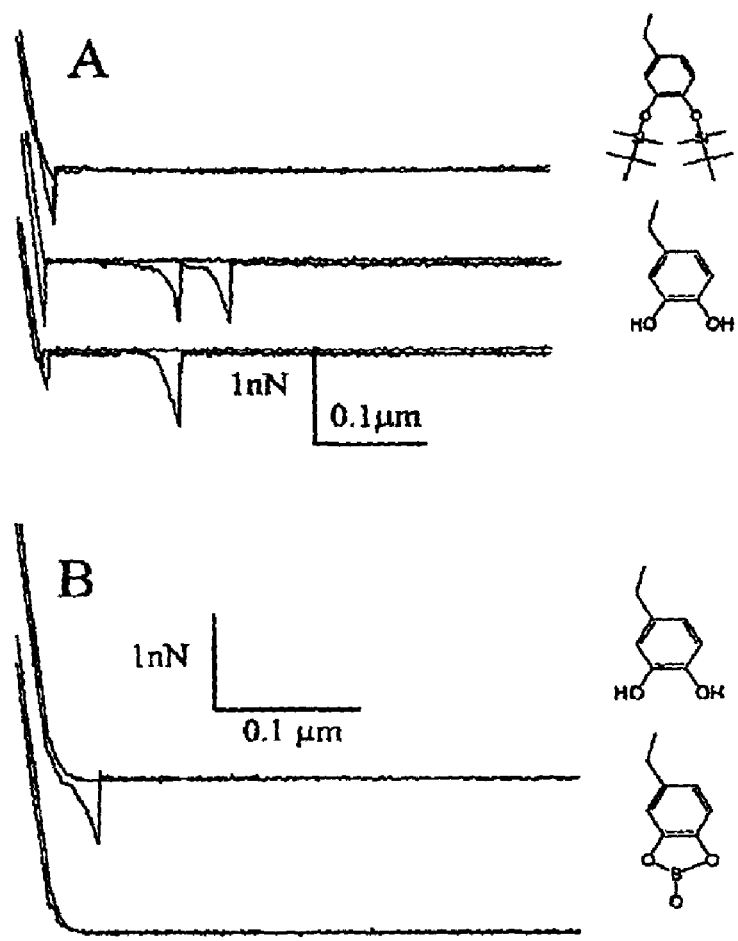
FIG. 31 is a force measure of side chain modified DOPA.

First, chemical modification of the hydroxyl group covalently by ertarybutyldimethylsiloxane, (TBDMS) resulted in no binding during two hundred approach-retraction cycles (FIG. 31 first line). However, deprotection of the TBDMS groups regenerated the binding ability of DOPA (FIG. 31, bottom two lines).

Second, the protection by ionic complexation with borate completely suppressed the strong adhesion of DOPA as well (FIG. 31, n=200). These data clearly confirmed the di-hydroxyl group of DOPA as the true structural source for strong and reversible binding.

Mussels developed an interesting way to create such a strong binding in water, a post-translational modification of tyrosine by tyrosine hydroxylase. This enzyme catalyzes a reaction of adding one hydroxyl group using tyrosine as a substrate and a large amount is found in threads and plaques where DOPA exists as well. It is surprising to say that the small post-translational modification (—OH) seems to produce a huge change of adhesive ability. Thus, experiments were designed to show a correlation between the posttranslational modification and binding ability.

A tyrosine tethered cantilever was prepared instead of DOPA, and tyrosine adhesion on TiO2 was investigated. No detectable force signals were observed except some non-specific adhesions with low probability (FIG. 35A). To reject the hypothesis that the tip used in this experiment didn't have any tyrosine molecules, the TiO2 surface was replaced with gold. The aromatic ring of tyrosine binds to a gold surface in a parallel orientation to the surface through π-π electron interaction, which is a well-known mechanism in surface adsorption chemistry18,19. The same cantilever used in TiO2 produced relatively strong adhesions repeatedly on gold surfaces (FIG. 35B). The statistical analysis of force distribution showed the π-π electron binding strength of 398 (±98) pN which was about 50% strength compared to the DOPA-TiO2 interaction (FIG. 35C). The force signals from tyrosine-gold binding also exhibited the same characteristics as previously shown in DOPA-TiO2 interaction: elastic stretching of PEG with an expected contour length and repetitive signal appearance with similar 'd' (FIG. 33C). In this experiment, it was clearly proved that the tyrosine hydroxylase-mediated post-translational modification greatly improved the binding ability of DOPA from almost zero to 800 pN.

Biological roles of DOPA go beyond adhesiveness upon oxidation: it crosslinks polypeptide chains resulting in stiffer materials found throughout threads and pads. The crosslinking mechanism has multiple pathways starting from a chemically unstable DOPAquinone structure. Aryl-aryl ring coupling (di-DOPA) has been found in mussel adhesive proteins[20] but Michael addition (quinone-alkylamine adducts) products have been found in other species not mussels (FIG. 36A). Therefore, these structures may occur as results of oxidation in mussels as well. It is clear in terms of crosslinking but is under debate with respect to adhesive properties after maturation i.e. oxidation. It was demonstrated that the DOPAquinone structure is not a major player for adhesiveness. The DOPAquinone-PEG chain is spatially and chemically stabilized by excess co-conjugation of methoxy-PEG molecules (5~10 molar equivalent) which is an important molecular configuration for preventing further reactions of DOPAquinone.

Time-resolved monitoring force signals of single DOPAquinone triggered by increasing pH (=9.7) uncovered interesting things that have been hidden so far. First, measured AFM signals showed two clear distributions in terms of force magnitude: high force and low force (FIG. 36B). Statistical analysis of the data yielded two clear histograms with 178±62 pN for low and 741±110 pN for high force (FIG. 36C). The quinone binding can be assigned to the low force region because it appeared only after the oxidation was triggered and subsequently became more frequent over time (FIG. 36D). The slow kinetic feature of DOPA oxidation contributed to initial high frequency of DOPA signals. This is the first single molecule experiment about detecting the structural change of a small molecule upon external stimulus. Based on these results, the possibility of the DOPAquinone structure being responsible for the high adhesiveness can be ruled out. Therefore, without being bound to any theory, the regeneration of reduced form i.e. di-hydroxyl group of DOPA during oxidation, is believed to be a very important requirement for maintaining or changing adhesive properties of DOPA containing materials at an interface.

In addition, the DOPA anchoring system can be a new platform to study other extensible biological macromolecules such as polysaccharides, DNA, and proteins. In the study performed, it already presented the elastic property of PEG (Mw 3400) and is believed to be the shortest chain length ever studied until now. This could be achievable simply because two defined anchoring methods were used at both ends: (1) covalent bonds between PEG and cantilever and (2) DOPA anchoring between PEG and substrate. This method is also highly contrasted with the conventional single molecule experiments where a tip 'sees' different molecules at every single movement of a cantilever. It has been a big barrier to investigate molecular responses upon external stimuli if a given stimulus was not hundred percent effective[23]. The DOPA-based anchorage system can be an alternative technique to overcome these problems in current single molecule pulling experiments.

Figure 32:
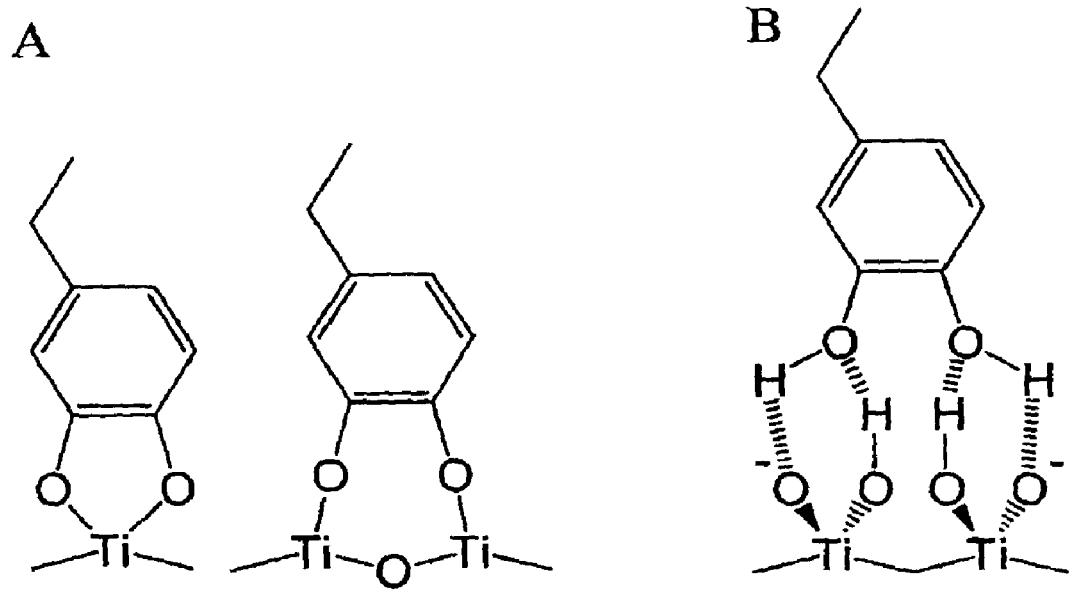
FIG. 32 is a proposed model of DOPA-$T_1O_2$ binding mechanism.

Currently, there is no clear answer why DOPA behaves like a reversible glue similar to 'Post-It'. Two molecular binding models, nomonuclear bidentate (FIG. 32A, right) and binuclear bidentate (FIG. 32A, left), are available but both did not consider the reversible binding of DOPA because the studies focused on only adsorption processes not desorption[25]. Therefore, the nature of chemical binding was assumed to be mainly covalent independent of factors resulting from the removal of water molecules after adsorption. One study using FTIR suggested that the nature of DOPA-TiO2 binding may be 60% ionic and 40% covalent. Based on this finding, a the molecular adsorption models were revised to incorporate the reversibility where multiple hydrogen bonds are formed in water (FIG. 32B)

FIG. 33. An Experimental Design and a Single Molecular DOPA Adhesion

A picture describes how the blue mussel (*Mytilus Edulis*) sticks to metal oxide surfaces. The circle included one plaque where the unusual amino acid, DOPA, was found.

(B) Two major protein components uncovered in plaques in mussels, Mefp-3 and Mefp-5. These mussel adhesive proteins have high content of DOPA: 27 mole % of Mefp-5 and 21% of Mefp-3. Bold Y (Y): DOPA, Italic S(S): phosphoserine, Italic R(R): hydroxyarginine.

(C) AFM tip modifications. Polymerization of 3-aminopropyltrimethoxysilane (APTMS) introduced amine groups on Si3N4 tip surfaces (not drawn). A long chain describes a PEG molecule conjugated with single (Boc)-DOPA at the end. Mixture of mPEG-NHS(2k) and Fmoc-PEG-NHS(3.4k)

at a molar ratio of 5~10:1 was used to stabilize DOPA-PEG molecule (see supplemental section for details).

FIG. 34. Single Molecule Force Measurement and Determination of Energy Landscape of DOPA Binding on TiO2 Surfaces Four representative AFM single molecule DOPA detachment signals from one cantilever. Those four signals were not consecutively generated (signals were deleted which didn't show any adhesions). Despite a low probability to detect DOPA adhesion (5~10%), detected signals showed similar 'd' values (refer to FIG. 34C).

(B) A histogram describing the distribution of force. Average is 781±151 pN (n=105) at a loading rate of 180 nN/sec.

(C) A definition of the distance, 'd', the z-directional moving distance of a piezoelectric device when DOPA-PEG molecule is fully stretched (D) A plot of bonding strength (linear) vs. loading rate (log). Loading rate was the product of spring constant of a cantilever and a pulling speed. Four different loading rates were selected: 1500, 180.7, 28.4 and 2 nN/sec. Averaged forces with standard deviation were plotted at each given loading rate. Forces were 846.48±157 pN (1500 nN/s), 781±151 pN (180 nN/s), 744±206 pN (28.4 nN/s), and 636.2±150 pN (2 nN/s).

(E) A schematic energy landscape of DOPA binding. External force tilted the landscape and lowered the energy barrier from the reaction coordinates. The slope (=kBT/xb) of the linear regression plot was 32.31 resulting in the distance to activation barrier (xb) was 1.27 Å. The energy barrier height was determined by extrapolation when a loading rate equals to zero (Eb=28.1 kcal/mol).

Figure 35:
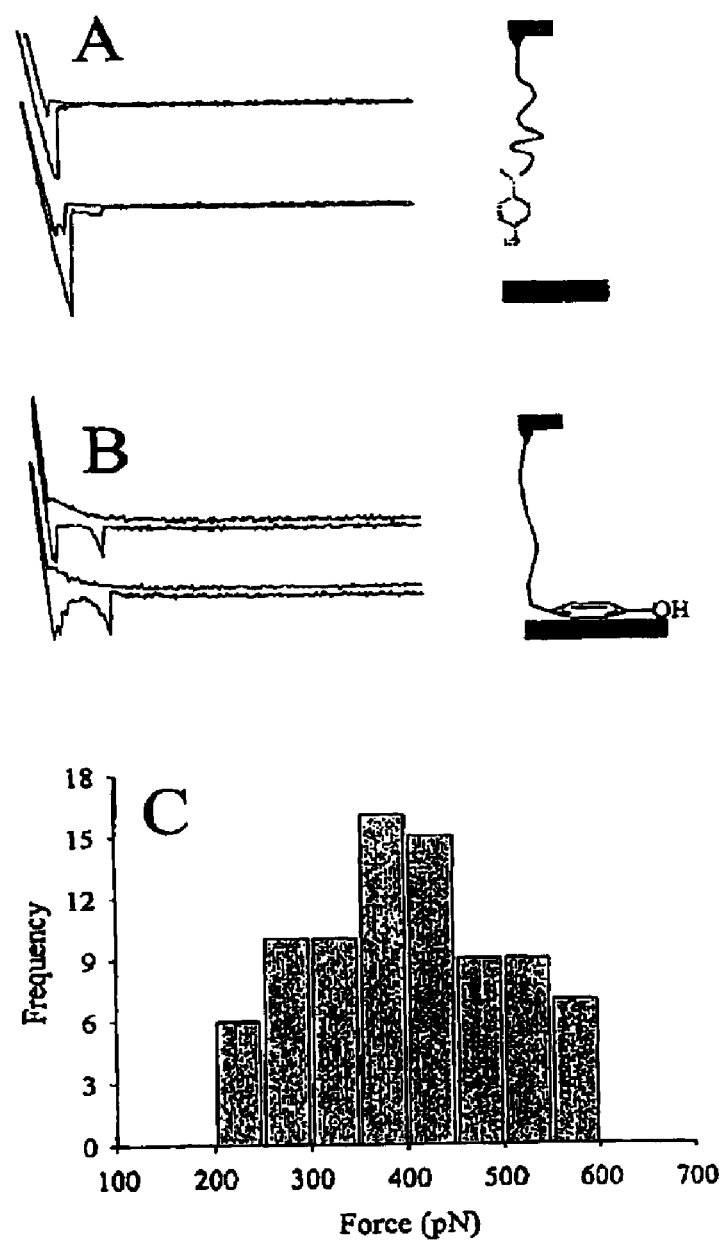
FIG. 35 is adhesion data.

FIG. 35. Molecular Identification of the Adhesive Origin of DOPA

Single molecule adhesion of tyrosine on TiO2 surfaces. No clear binding signals were detected (upper representative signal, n=639 out of 700 repeats) except the initial electrostatic interactions which were unavoidable in some cantilevers. Nonspecific adsorption signals (lower representative signal, n=61 out of 700).

(B) Confirmation of tyrosine existence on the tip surface. Pi($\pi$) electrons of tyrosine phenyl group specifically interact with gold $\pi$-electron.

(C) Force distributions of tyrosine binding to a gold surface. Tyrosine presented 398±98 pN (180 nN/sec) adhesion strength.

FIG. 36. The Change of DOPA Adhesiveness Upon Oxidation (DOPAquinone)

A schematic chemistry pathway of the formation and oxidation of DOPA. DOPA was created by the action of tyrosine hydrxylase and subsequently oxidized to DOPAquinone by pH and the enzyme. It is unstable and reactive due to tendency of radical formation of DOPAquinone. It can crosslink with other DOPA molecules (di-DOPA) as well as reacts with amine groups from lysines. The arrows are the potential reactions found in other species not in mussel adhesive proteins.

(B) Representative force signals (n=16) with similar 'd' defined in FIG. 1C (~50 nm). They were collected for 1 hr AFM experiment (1800 repeats) in a basic condition (20 mM Tris-Cl, pH 9.7). Time progress makes from the top to bottom of the graph. Red signals indicate DOPA-TiO2 and black signals for DOPAquinone-TiO2

(C) Force histograms after total analysis of 1800 F-D curves. The histogram at a low force region showed 178±82 pN (n=143) and the one at a high force region exhibited 741±10 pN (n=51).

(D) A scatter plot of the number of events during a specified time window (10 min). DOPA signals (circle, left y-axis) gradually decreased from twenty-two events for the first ten minutes to only three events during the last time window. However, quinone signals (triangle, right y-axis) increased from one event at the first time window to forty-two events at the last time window (50~60 min).

To summarize, successfully measured the single molecule binding strength of DOPA (~0.8 nN) was successfully measured, and the reversible binding chemistry was shown. This strong adhesion was created by post-translational modification but was significantly reduced by oxidation of DOPA, to DOPAquinone.

Figure 20:
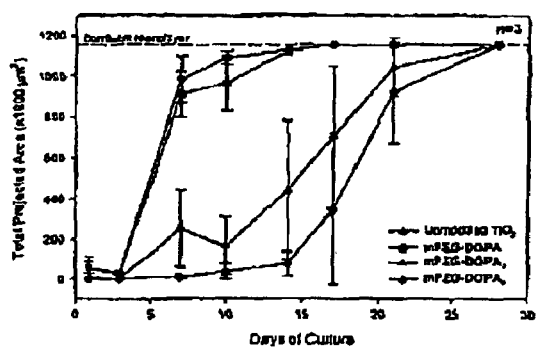
FIG. 20 plots the long-term resistance to cell adhesion on $TiO_2$ and $TiO_2$ modified with mPEG-DOPA$_{1-3}$. The duration of the non-fouling response is proportional to the length of the DOPA peptide anchoring group. Adherent cells were visualized with calcium AM.
Figure 23:
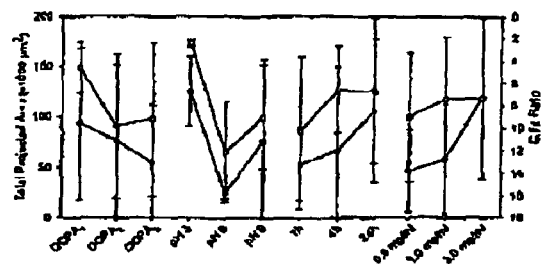
FIG. 23 plots the results of the Robust Design experiment on 316L stainless steel.
Figure 21:
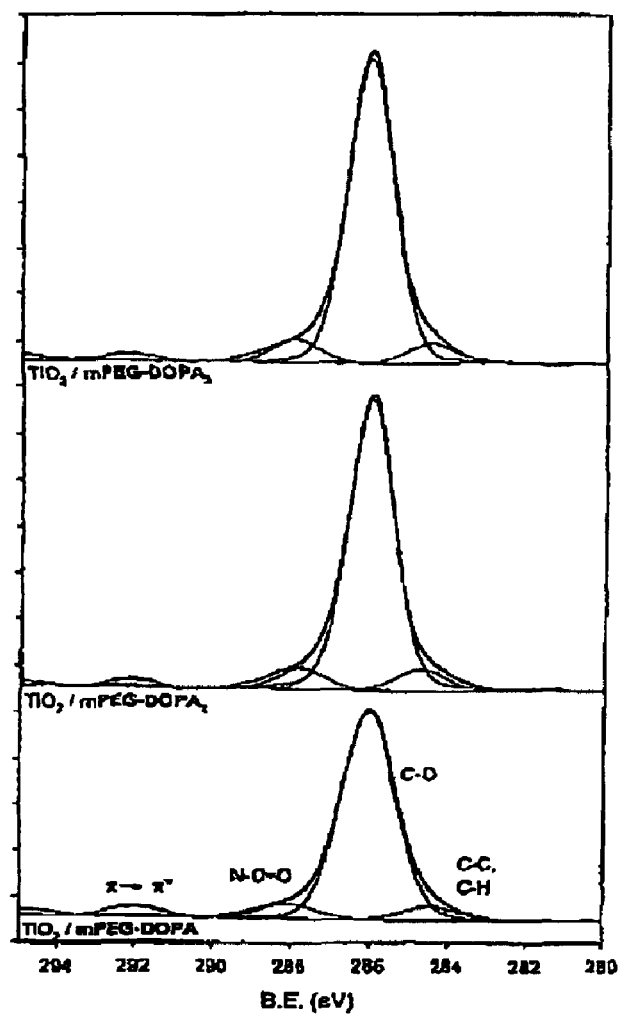
FIG. 21 plots the high-resolution XPS scans of the C1s region of $TiO_2$ substrates modified with mPEG-DOPA$_{1-3}$. Of note is the increase in the ether carbon peak (286.0 eV) with increasing length of the DOPA peptide anchor.
Figure 22:
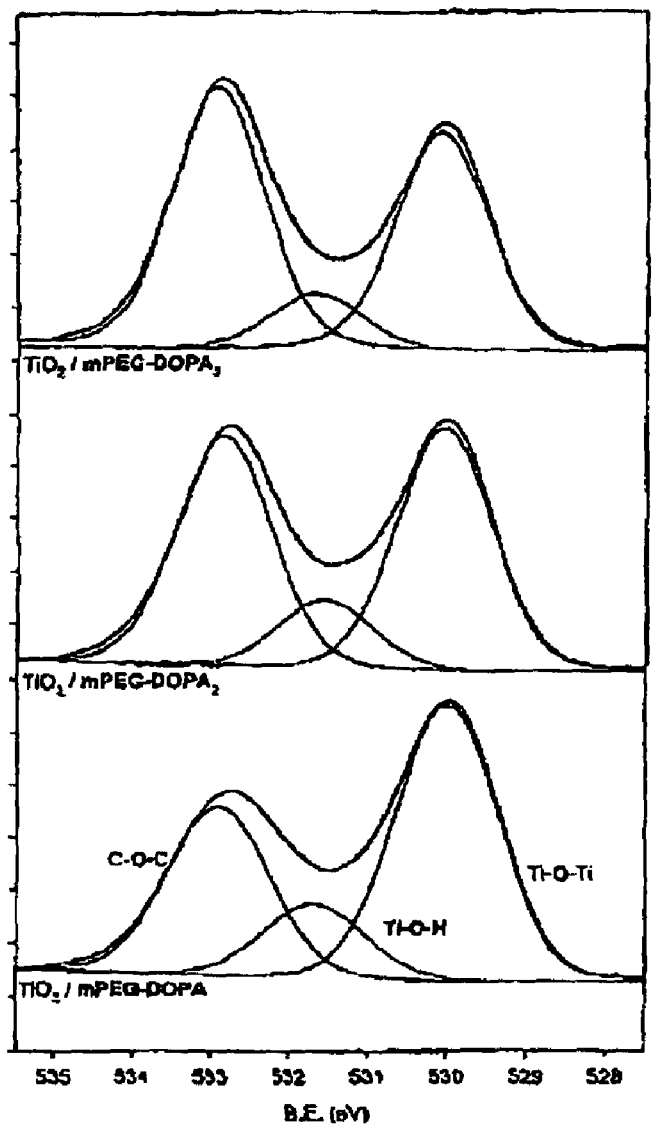
FIG. 22 plots the high-resolution XPS scans of the O1s region of $TiO_2$ substrates modified with mPEG-DOPA$_{1-3}$. The peak at 532.9 eV representing polymeric oxygen increases while the Ti—O—H peak (531.7 eV) decreases with increasing DOPA peptide length.

The antifouling coating of the present invention can either be essentially permanent i.e., lasting 120 days or more, or biodegradable depending on the number of DOPA or DOPA-derived moieties in the adhesive component. FIG. 20 shows the results of a 28-day 3T3 fibroblast cell adhesion and spreading assay on TiO$_2$ treated with mPEG-DOPA$_{1-3}$. At early time points (i.e. less than 7 days), the protein and cell attachment resistance correlates well with the length of the DOPA peptide anchoring group, with resistance increasing in the order mPEG-DOPA<mPEG-DOPA$_2$<mPEG-DOPA$_3$. TiO$_2$ substrates treated with mPEG-DOPA$_2$ and mPEG-DOPA$_3$ maintain reduced cell attachment, or resistance, through 21 days.

Robust design methodology was used to determine the effect of DOPA peptide anchor length and modification conditions (pH, concentration and time) on the PEG surface density and antifouling performance of metal, metal oxide, semiconductor, and polymer surfaces. The nine experiments utilized for each substrate are described below in Table 7. For nearly all surfaces, the length of the DOPA peptide and the pH of the modification buffer lead to the largest variation in the amount of PEG absorbed, as measured by XPS and the adhesion and spreading of 3T3 fibroblasts. The experiments summarized in Table 7 permitted the determination of modification conditions that provided optional cell adhesion resistance for a variety of materials, as measured by 4-hour cell attachment assays. After the nine experiments were performed on each substrate, the data was subjected to Robust Design analysis. The presence of large error values when plotting Robust Design data is a characteristic of the technique since a single data point at one factor level contains the variation of the remaining factors averaged over all the levels.

The polymeric compositions of the present invention can be also used to coat the surfaces of devices and instrumentation used for handling body fluids including sera. The coating on the surface of the device or instrument blocks protein binding to the surfaces thus reducing or eliminating the need for extensive washing or cleaning of the device or instrument between uses. The devices need to be thoroughly cleaned to prevent cross contamination between samples of bodily fluids applied top the device. Presently, the cleaning of these instruments and device between uses requires extensive washing with caustic agents such as 50% bleach and/or elevated temperatures. The coating process would be to circulate an aqueous solution of 1 mg/ml of DHPD polymer through the device at room temperature for a period of a few hours.

The coatings of the present invention can be used on medical implants for a wide variety of uses. For example, the coatings can be used to block bacterial adhesion and therefore growth on the implanted device reducing the possibility of infection at the site of implant. The coatings can be used to reduce the amount of acute inflammation on the device by reducing protein binding and cell adhesion to the device. The coatings of the present invention can also be used as nanoparticles to prevent aggregation of these particle in the presence of serum.

Hydrogels

The polymeric compositions of the present invention can also be as surgical adhesives for medical and dental uses and as vehicles for drug delivery to mucosal surfaces. The polymeric compositions can be used as tissue adhesive polymeric hydrogels for medical uses such as tissue sealants, gels for prevention of surgical adhesions (scar tissue formation), bone and cartilage adhesives, tissue engineering, and site specific drug elution and for research uses such as immobilization of proteins including antibodies and small molecule analytes including pharmaceuticals. The polymeric compositions of the present invention may also be used as interfacial bonding agents, wherein the neat monomers or solution of monomers are applied to a surface as a primer or bonding agent between a tissue surface or a metal or metal oxide implant/device surface and a bulk polymer or polymer hydrogel. With an appropriate polymer component, which one of ordinary skill in the art could identify, the polymeric compositions of the present invention can be injected or delivered in a fluid form and harden in situ to form a gel network. The in situ hardening can occur through photocuring, chemical oxidation, enzymatic reaction or through the natural increase in temperature resulting from delivery into the body.

In part, the present invention is also a method for the non-oxidative gelation of a polymeric composition of the present invention. One such method includes (1) providing a polymeric composition of the present invention; (2) admixing water and the polymeric composition; and (3) increasing admixture temperature sufficient to gel the polymeric composition, such temperature increase without oxidation of the polymer or DOPA or DOPA-derived moiety residue incorporated therein. Depending upon choice and identity of the polymer component of such a composition, an increase in admixture concentration can reduce the temperature required to effect gelation. Depending upon choice and identity of a particular copolymer component, a larger hydrophilic block thereof can increase the temperature required to gel the corresponding composition. Various other structural and/or physical parameters can be modified to tailor gelation, such modifications as can be extended to other polymeric compositions and/or systems which are consistent with the broader aspects of this invention.

It is widely acknowledged that the commercially-available PLURONIC® block copolymers self-assemble in a concentration- and temperature-dependent manner into micelles consisting of a hydrophobic PPO core and a water-swollen corona consisting of PEO segments. At high concentration, certain PEO-PPO-PEO block copolymers, such as PLURONIC® F127 and PLURONIC® F68, transform from a low viscosity solution to a clear thermoreversible gel at elevated temperature. While not wanting to be bound by theory, it is generally assumed that the interactions between micelles at elevated temperature lead to the formation of a gel phase, which is stabilized by micelle entanglements. The micellization and gelation processes depend on factors such as block copolymer molecular weight, relative block sizes, solvent composition, polymer concentration, and temperature. For example, increasing the length of the hydrophilic PEO blocks relative to the hydrophobic PPO block results in an increase in micellization and gelation temperature ($T_{gel}$).

Figure 2:
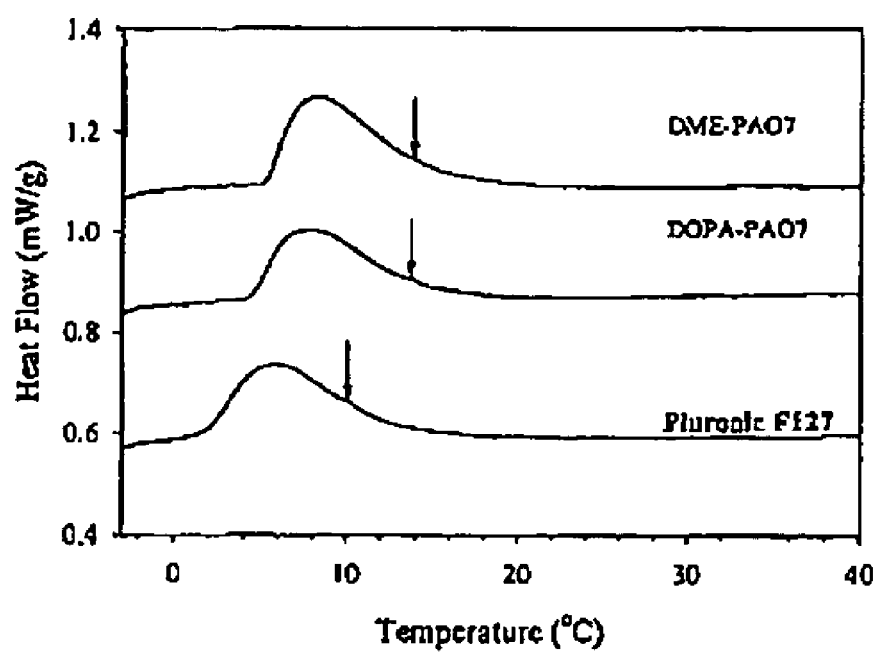
FIG. 2 provides differential scanning calorimetry thermograms of 30 wt % DME-PAO7, DOPA-PAO7, and unmodified PLURONIC® F127 aqueous solutions. Arrows indicate the location of gelation endotherm.

Differential scanning calorimetry (DSC) measurements were performed on aqueous solutions of DME-PAO7 and DOPA-PAO7 at different concentrations to detect aggregation of block copolymers into micelles. DSC profiles obtained for PLURONIC® F127, DME-PAO7 and DOPA-PAO7 were found to be qualitatively similar and were characterized by a large endothermic transition corresponding to micelle formation followed by a small endotherm at $T_{gel}$ (FIG. 2). The transition temperature of the small peak was found to correlate strongly with $T_{gel}$ determined by rheometry and the vial inversion method (Table 4).

TABLE 4

Gel temperatures obtained from vial inversion method, rheology or differential scanning calorimetry for 22 wt % DME-PAO7, DOPA-PAO7 and PLURONIC ® F127 solutions.

| | Gel Temperature (° C.) | | |
|---|---|---|---|
| | vial inversion method | Rheological | DSC |
| DME-PAO7 (22 wt %) | 22.0 ± 1.0 | 20.3 ± 0.6 | 20.9 ± 0.1 |
| DOPA-PAO7 (22 wt %) | 22.0 ± 1.0 | 20.4 ± 0.5 | 21.7 ± 0.2 |
| PLURONIC ® F127 (22 wt %) | 17.0 ± 1.0 | 15.4 ± 0.4 | 17.5 ± 0.4 |

Aqueous solutions with concentrations ranging from 10 to 30% (w/w) of DOPA-PAO7 copolymers and 35 to 54% (w/w) of DOPA-PAO8 copolymers were prepared by the cold method, in which DOPA conjugate was dissolved in distilled water at about 4° C. with intermittent agitation until a clear solution was obtained. Thermal gelation of concentrated solutions was initially assessed using the vial inversion method. In this method, the temperature at which the solution no longer flows is taken as the gelation temperature.

The gelation temperature was found to be strongly dependent on copolymer concentration and block copolymer composition (i.e., PAO7 versus PAO8). For example, 22 wt % solutions of DOPA-PAO7 and DME-PAO8 were found to form a transparent gel at approximately 22.0±1.0° C.; decreasing the polymer concentration to 18 wt % resulted in a gelation temperature of approximately 31.0±1.0° C. However, DOPA-PAO7 solutions with concentrations less than 17 wt % did not form gels when heated to 60° C. DOPA-PAO7 exhibits a slightly higher gel temperature than that (17.0±1.0° C.) of unmodified PLURONIC® F127. The gelation behavior of DOPA-PAO8 was found to be qualitatively similar, except that much higher polymer concentrations were required to form a gel. 54 wt % solutions of DOPA-PAO8 and DME-PAO8 formed gels at 23.0±1.0° C., while 50 wt % of DOPA-PAO8 gels at 33.0±1.0° C. However, DOPA-PAO8 solutions with concentrations less than 35 wt % did not form gels when heated to 60° C. DOPA-PAO8 exhibits a much higher gel temperature than that (16.0±1.0° C.) of unmodified PLURONIC® F68. These gels were found to be resistant to flow over long periods of time. From this experiment, we have also found that both DOPA and DOPA methyl ester-derivatives of the same commercially available PLURONIC® PAO exhibit almost the same gel temperature, and the gel made from 54 wt % of either DME-PAO8 or DOPA-PAO8 at room temperature is stiffer than that made from 22 wt % of either DME-PAO7 or DOPA-PAO7.

Figure 3:
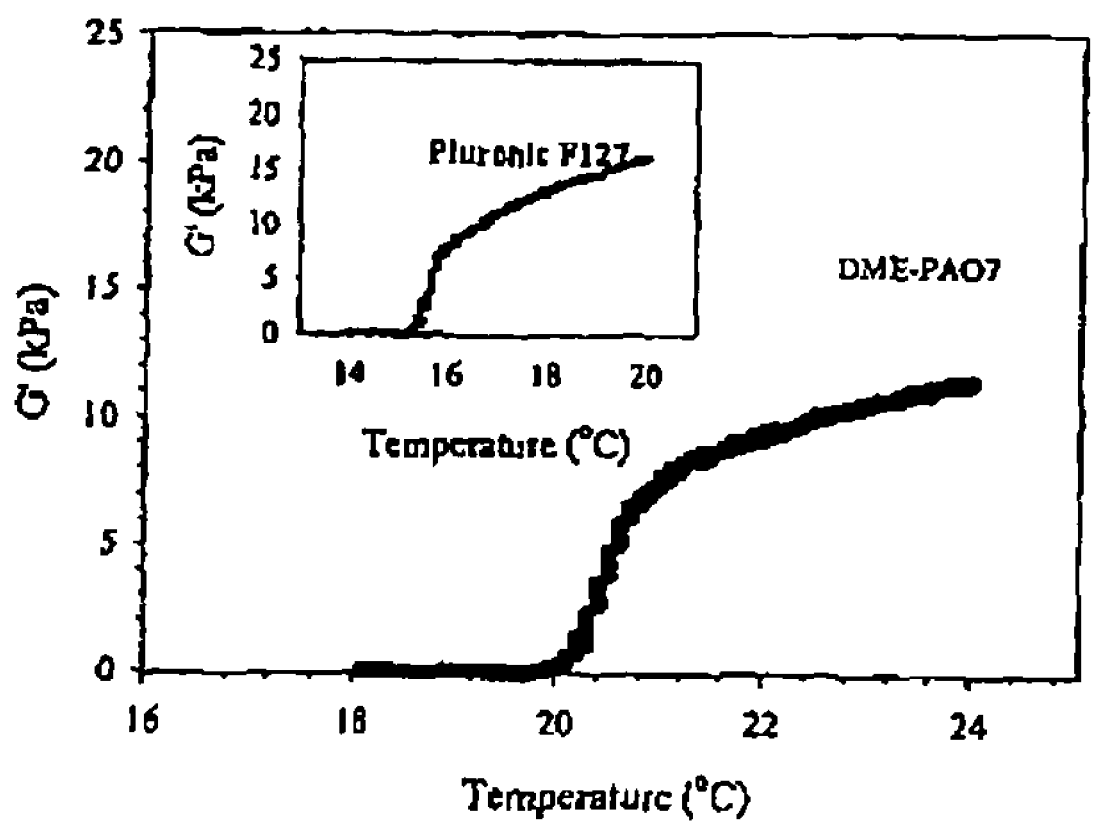
FIG. 3 plots shear storage modulus, G', of a 22 wt % DME-PAO7 aqueous solution as a function of temperature at 0.1 Hz and a strain of 0.45%. Shown in the inset is the rheological profile of a 22 wt % unmodified-PLURONIC® F127 aqueous solution as a function of temperature.

The viscoelastic behavior of DOPA-modified PLURONIC® solutions was further studied by oscillatory rheometry. FIG. 3 shows the elastic storage modulus, G', of 22 wt % solutions of unmodified PLURONIC® F127 and DME-PAO7 aqueous solutions as a function of temperature. Below the gelation temperature, storage modulus G' was negligible, however G' increased rapidly at the gel temperature ($T_{gel}$), defined as the onset of the increase of the G' vs. Temperature plot. DOPA-PAO7 (not shown) exhibited a similar rheological profile. The $T_{gel}$ of 22 wt % solutions of DME-PAO7 and DOPA-PAO7 were found to be identical (20.3±0.6° C.), which is approximately 5 degrees higher than an equivalent concentration of unmodified-PLURONIC® F127 (15.4±0.4° C.). G' of DME-PAO7 or DOPA-PAO7 approaches a plateau value of 13 kPa, which is comparable to that of unmodified PLURONIC® F127.

Figure 4:
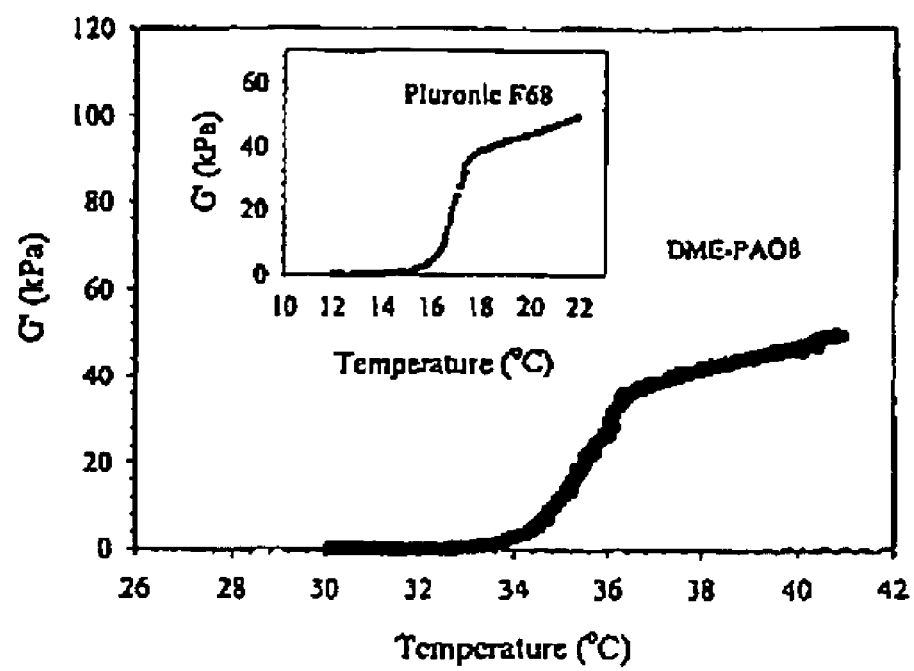
FIG. 4 plots shear storage modulus, G', of a 50 wt % DME-PAO8 aqueous solution as a function of temperature at 0.1 Hz and a strain of 0.45%. Shown in the inset is the rheological profile of a 50 wt % unmodified PLURONIC® F68 aqueous solution as a function of temperature.
Figure 5:
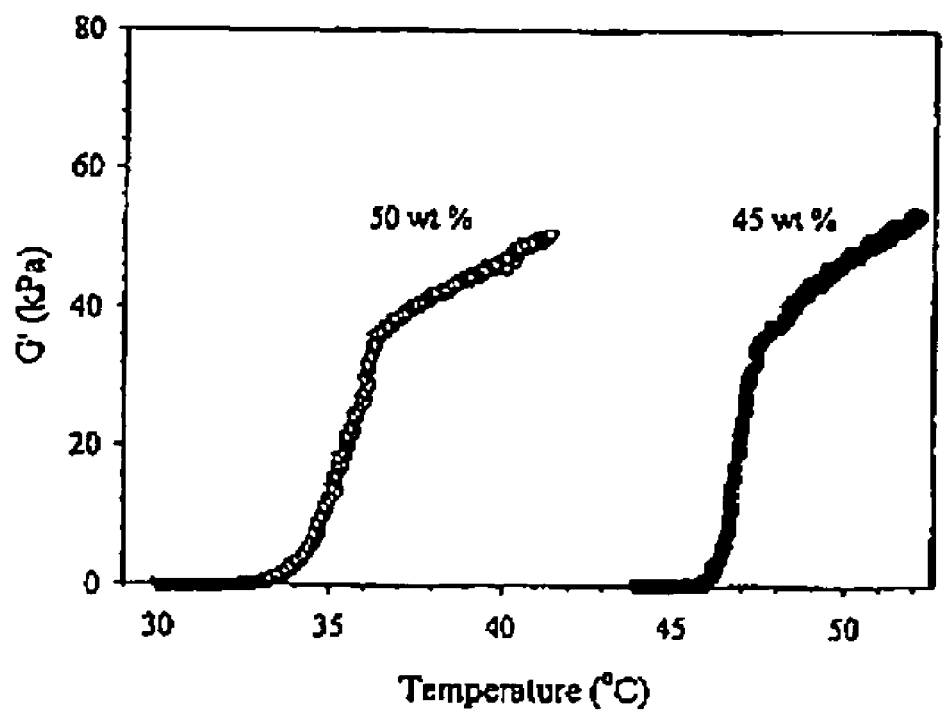
FIG. 5 plots storage moduli of DME-PAO8 aqueous solutions at 45 wt % and 50 wt %, respectively, as a function of temperature at 0.1 Hz and a strain of 0.45%.

Shown in FIG. 4 are the rheological profiles of 50 wt % solutions of unmodified PLURONIC® F68 and DME-PAO8 as a function of temperature. The $T_{gel}$ of a 50 wt % DME-PAO8 solution was found to be 34.1±0.6° e, whereas the $T_{gel}$ of an equivalent concentration of unmodified PLURONIC® F68 was approximately 18° C. lower (16.2±0.8° C.). The plateau storage moduli of 50 wt % solutions of DME-PAO8 and unmodified PLURONIC® F68 were not significantly different, approaching a plateau value as high as 50 kPa. The concentration dependence of $T_{gel}$ is illustrated in FIG. 5, which shows the rheological profile of DME-PAO8 at two different concentrations as a function of temperature. $T_{gel}$ of 45 wt % solution of DME-PAO8 was observed to be approximately 12° C. higher than that of 50 wt % solution of DME-PAO8.

Since both DOPA and DOPA methyl ester can be considered hydrophilic, the increase of $T_{gel}$ observed in the DOPA-modified PLURONIC® PAOs, compared with that of unmodified PLURONIC® PAOs, is likely due to the increase in length of the hydrophilic PEO segments resulting from coupling of DOPA to the endgroups. It is clear from the data shown in FIGS. 3 and 4 that the coupling of DOPA or DOPA methyl ester to the PLURONIC® PAO endgroups has a more significant impact on the $T_{gel}$ of PLURONIC® F68 compared to PLURONIC® F127. This can be rationalized in terms of the overall molecular weights of F68 (approx. 8,600) and F127 (approx. 12,600). Addition of DOPA and DOPA methyl ester to both endgroups using the chemistry shown in Scheme 1 results in an increase in molecular weight of 446 and 474, respectively. This represents a larger % molecular weight increase for F68 compared to F127, due to lower base molecular weight of F68.

The data presented herein is in agreement with previous calorimetry studies of unmodified PLURONIC® PAOs, which demonstrated that the broad peak at low temperature is due to micellization while the small peak at higher temperature, only observed in concentrated solutions, corresponds to gelation, a nearly athermal process. As seen in Table 5, the onset temperature of micellization, the temperature at maximum heat capacity and $T_{gel}$ of unmodified PLURONIC® F127 were found to be lower than those of DOPA-PAO7, whereas the specific enthalpies determined from the areas under the transition (FIG. 2) are approximately the same. These enthalpies include contributions from both micellization and gelation. However, due to the small enthalpy of gelation, the observed enthalpy changes can be largely attributed to micellization.

TABLE 5

Comparisons of 30 wt % DME-PAO7, DOPA-PAO7 and unmodified PLURONIC ® F127 solutions on onset micellization temperature, temperature at maximum heat capacity, enthalpies, and gel temperature from differential scanning calorimetry experiments

|  | Micellization temp.(° C.) | Temp. at Max. heat capacity (° C.) | ΔH (J/g) | Gel Temp. (° C.) |
|---|---|---|---|---|
| DME-PAO7 (30 wt %) | 5.2 ± 0.2 | 8.3 ± 0.1 | 20.3 ± 2.4 | 14.0 ± 0.4 |
| DOPA-PAO7 (30 wt %) | 4.6 ± 0.2 | 8.0 ± 0.6 | 19.3 ± 1.4 | 14.0 ± 0.2 |
| PLURONIC ® F127 (30 wt %) | 1.9 ± 0.3 | 6.0 ± 0.4 | 20.6 ± 1.6 | 10.6 ± 0.6 |

Figure 6A:
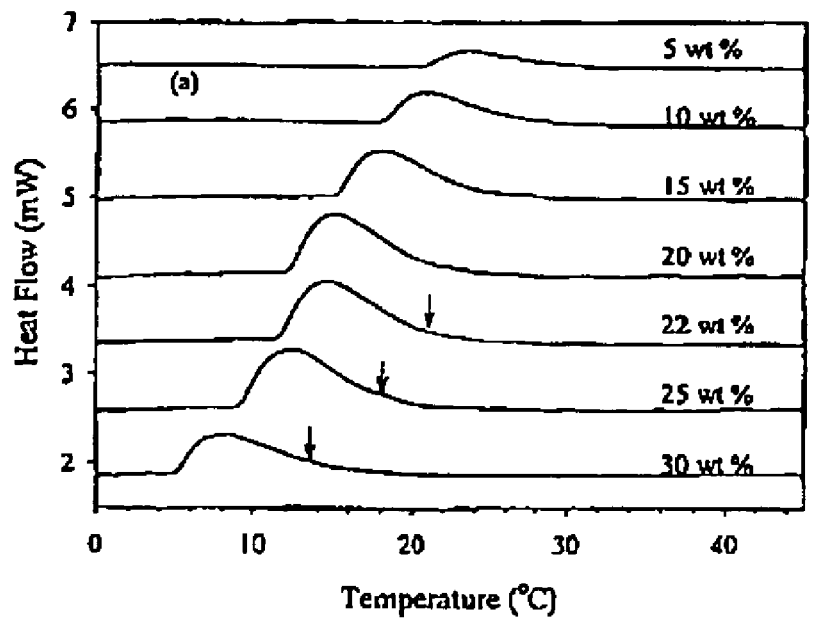
FIGS. 6A and 6B show differential scanning calorimetry thermograms of (A) DOPA-PAO7 and (B) DME-PAO7 at different concentrations upon heating. Arrows indicate the location of gelation endotherm observed only at higher polymer concentrations.
Figure 6B:
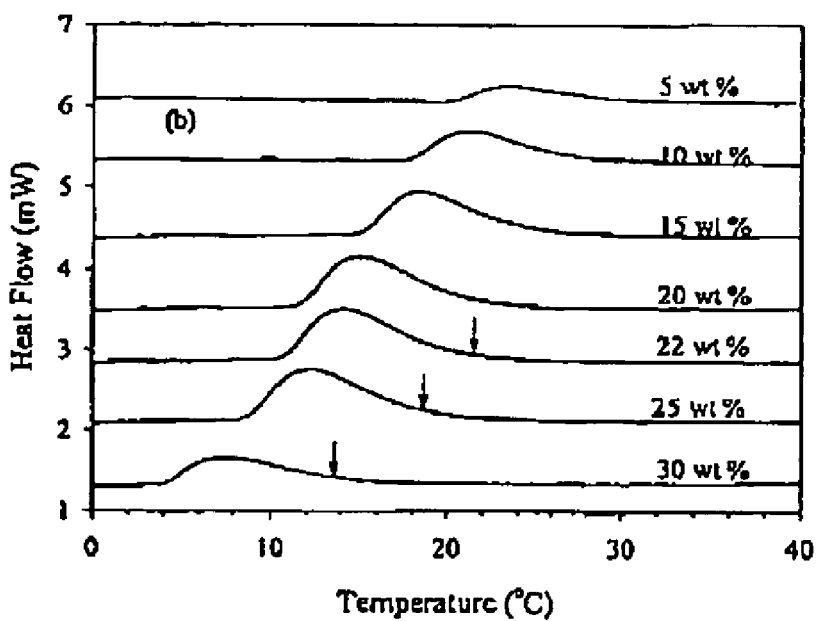

The micellization peak was seen to extend to temperatures above the onset of gelation, indicating that additional monomers aggregate into micelles at temperatures above the gelation point. The concentration dependence of DOPA-PAO7 and DME-PAO7 aggregation is shown in FIG. 6. DSC thermograms indicate a decrease in micellization temperature and $T_{gel}$ with increasing polymer concentration. The broad endothermic peak corresponding to micellization can also be observed in solutions at concentrations at which no gelation takes place; the characteristic temperature of the broad peak increases linearly with decreasing copolymer concentration, whereas the small peak was observed to coincide to the gel temperature of the concentrate copolymers but disappears as copolymer concentration decreases.

As can be gathered from the preceding, various polymeric compositions of this invention can be designed and prepared to provide various micellization and/or thermal gelation properties. Alternatively, or in conjunction therewith, degradation into excretable polymer components and metabolites can be achieved using, for instance, polyethylene glycol and lactic/glycolic acids, respectively. Regardless, the polymeric compositions of this invention provide improved adhesion by incorporation of one or more DHPD residues, such incorporation resulting from the coupling of a terminal monomer of the polymeric component to such a residue.

Another method of non-oxidative gelation of a polymeric composition of the present invention is photocuring. A photocurable DHPD-moiety-containing monomer is copolymerized with PEG-DA (PEG-diacrylate) to form adhesive hydrogels through photopolymerization. Photopolymerization can be achieved at any visible of UV wavelength depending on the monomer used. This is decidedly determined by one skilled in the art. The photocurable monomers consist of an adhesive moiety coupled to a polymerizeable monomer with a vinyl group, such as a methacrylate group with or without an oligomeric ethylene oxide linker or fluorinated ether linker in between.

An aqueous mixture of a photopolymerizable monomer containing an adhesive of the present invention and PEG-DA and 1.5 μL/mL of a photoinitiator, such as 2,2'-dimethoxy-2-phneyl-acetonephenone (DMPA), camphorquinone/4-(dimethylamino)-benzoic acid (CQ/DMAB), and ascorbic acid/fluorescein sodium salt (AA/FNa$_2$) was irradiated using a UV lamp (365 nm), for more than 5 minutes. Presence of the adhesive in the precursor solution was found to affect the radical polymerization process. The catechol adhesive decreased the extent of gel formation, reduced the percent of adhesive incorporation in the gel network, and lengthened the gel formation time.

Figure 25:
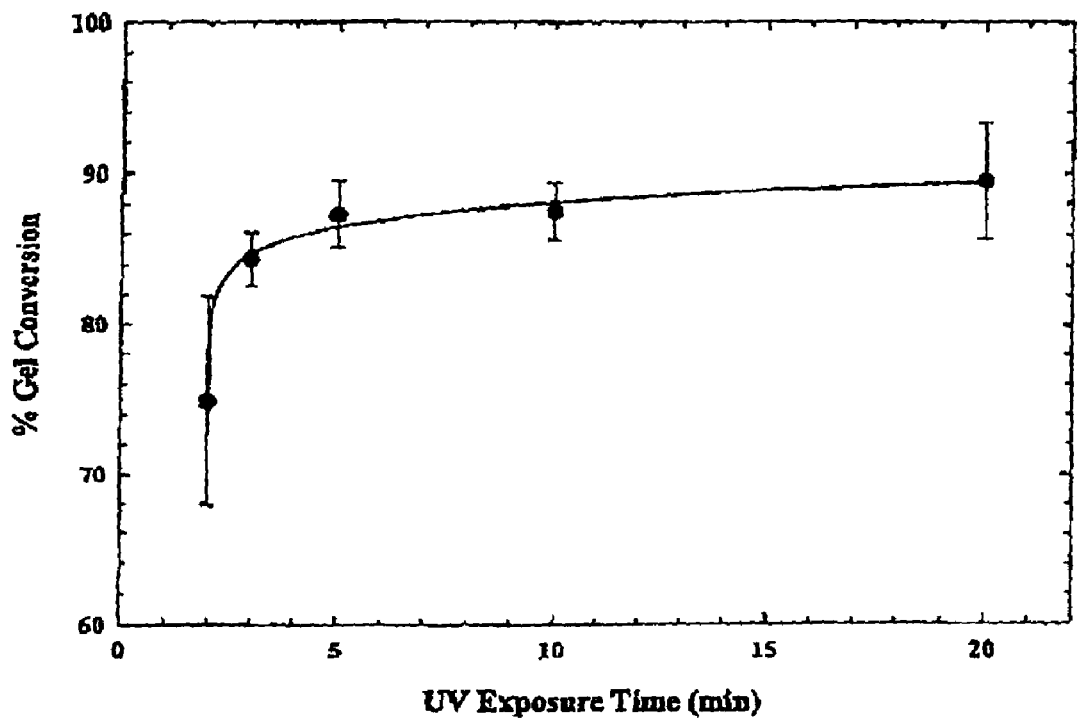
FIG. 25 plots the % gel conversion versus the UV exposure time in minutes.

As shown in FIG. 25, gel conversion as determined by measuring the mass of the sondgel, reached more than 75 wt % after 2 minutes of UV irradiation and increased to greater than 85 wt % upon irradiation for more than 5 minutes. Gelation of PEG-DA occurred in 4 minutes or less when visible light initiators were used (4 minutes for CQ/DMAB and 3 minutes for AA/FNa$_2$).

Copolymerization of PEG-DA with 1 or 7 (syntheses of 1 and 7 are shown in Schemes 2 and 3) was qualitatively similar to polymerization of pure PEG-DA, although addition of 1 or 7 to the PEG-DA precursor solution resulted in a decrease in gel conversion that was dependent on DOPA monomer concentration and initiating system. For example, in DMPA-initiated UV polymerization, gel conversion was reduced to less than 85 wt % in the presence of 2.5 mol % or more of 1 or 7. However, the extent of gel conversion was not statistically different between the gels. Similar DOPA concentration dependent inhibition was observed for the visible light induced initiators. For AA/FNa$_2$ and CQ/DMAB initiated mixtures, addition of 33.3 mol % of 1 increased the gelation time to more than 8 minutes. Nevertheless, solutions containing 1 and 7 were still capable of photocuring even at a relatively high mol % of DOPA.

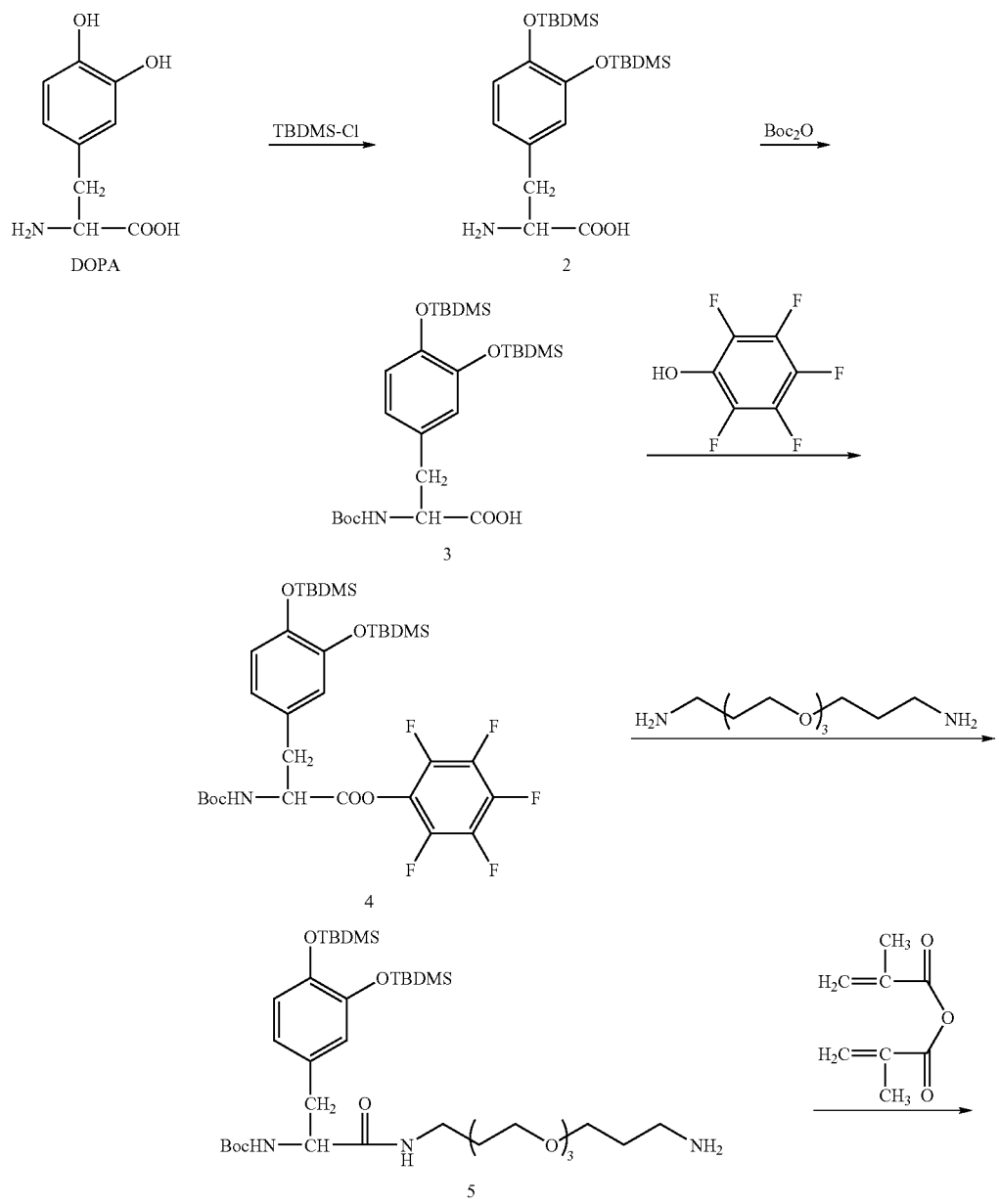

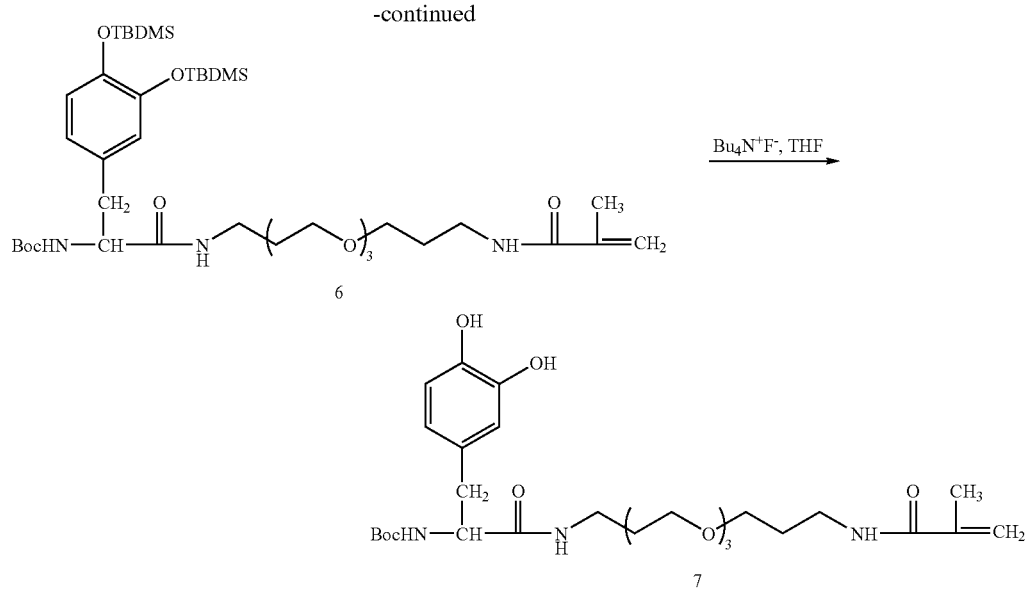

Figure 26:
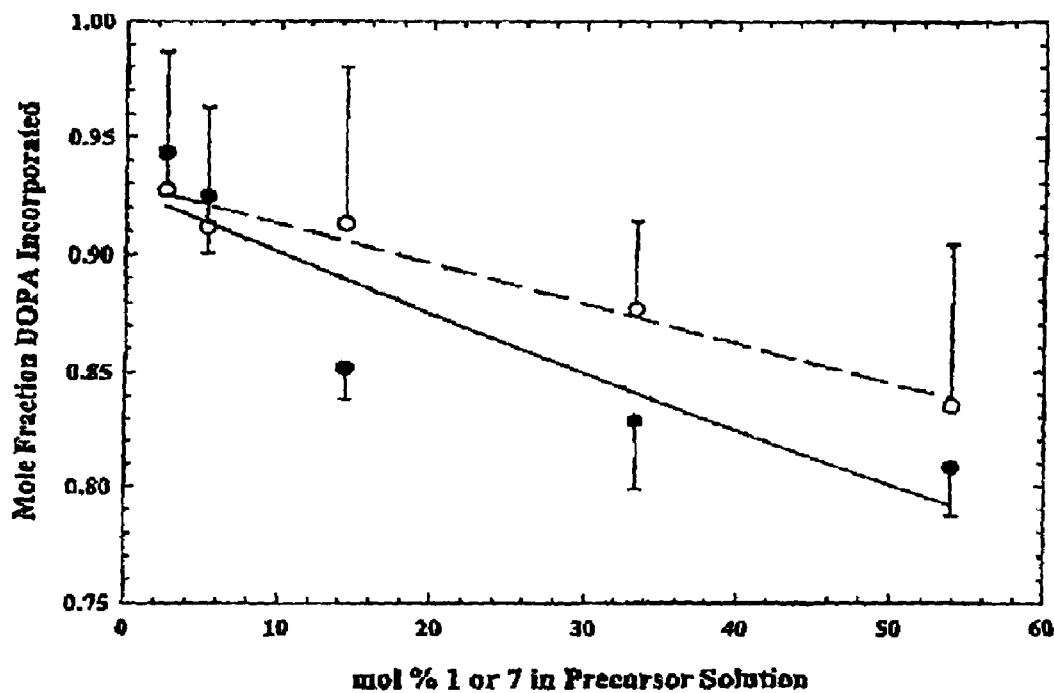
FIG. 26 plots the mole fraction of DOPA incorporated versus the mol % of 1 or 7 in the precursor solution.
Figure 27:
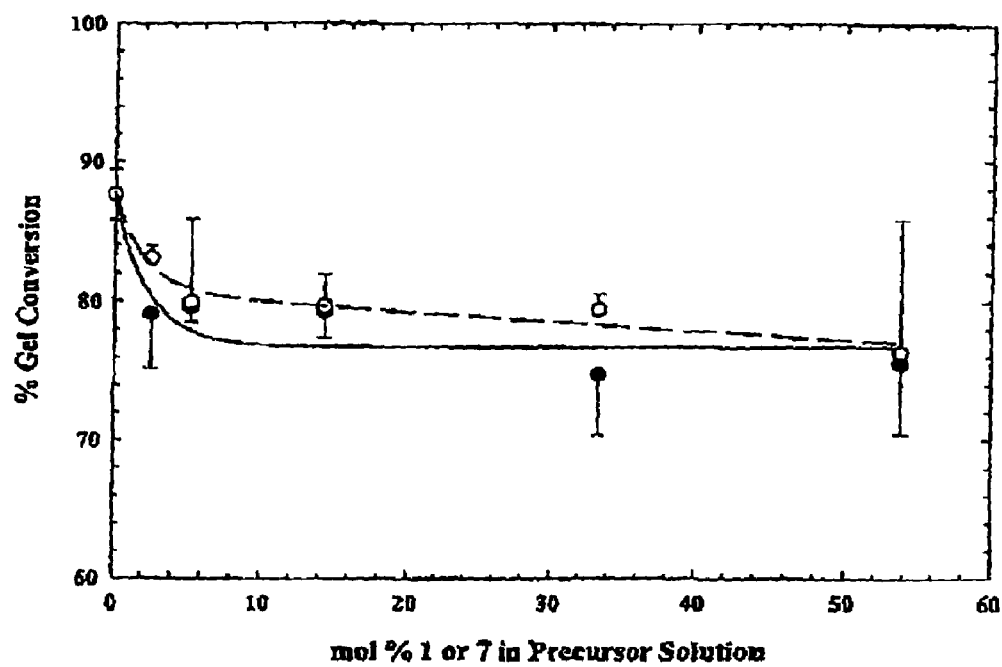
FIG. 27 plots the % gel conversion versus mol % 1 or in the precursor solution.

For example, 53.8 mol % of either 1 or 7 in the precursor solution reduced the gel weight % from 88 to 77 and only 85 mol % of the DOPA was incorporated into the hydrogel. A calorimetric DOPA assay developed by Waite and Benedict performed on the photocured hydrogels revealed the presence of catecholic DOPA in the hydrogel. After photocuring, DOPA-containing gels were dialyzed in 0.5 N HCl to extract unreacted DOPA monomer. To quantify the extent of DOPA incorporation, the dialysate was analyzed according to the DOPA colorimetric assay of Waite and Benedict and the results were used to calculate the amount of DOPA incorporated into the gel network. FIG. 26 shows the mole fraction of DOPA incorporated into the gel network, as a function of mol % monomer 1 and 7 in the precursor solution. There was no significant difference in the mole fraction of DOPA incorporated between samples containing 1 and 7. As much as 24.9 μmol/g of DOPA was incorporated into the PEG hydrogels.

Direct evidence for the presence of DOPA in the gels was obtained by immersing the intact dialyzed hydrogels in nitrite reagent followed by NaOH. The initially colorless gels turned bright yellow after the addition of the nitrite reagent and then red following the addition of excess base. This color transition is typical of catechols, indicating that the unoxidized form of DOPA was incorporated into the hydrogels through photopolymerization. The intensity of the red color also reflects the concentration of DOPA incorporated into the photocured gels.

Contact mechanical tests were performed on the photocured gels in the shape of hemispheres to obtain information on the mechanical properties of the gels. Elastic moduli (E) were calculated by assuming Hertzian mechanics for the specific case of non-adhesive contact between an incompressible elastic hemisphere and a rigid plane, in which case the Hertzian relationship between load ($P_h$) and displacement ($\delta_h$) becomes:

$$P_h = \frac{16R^{1/2}E}{9} \delta_h^{3/2} \quad (1)$$

where R is the radius of curvature of the hemispherical gel. Load versus displacement data was fitted with Equation (1), which allowed the elastic moduli to be calculated based on the proportionality factor of the curve fit. As seen in Table 6, average Young's moduli (E) for DOPA-containing gel of around 50 kPa was obtained.

TABLE 6

Average Young's Moduli for DOPA containing gels

| | DOPA Content* (μmol/g gel) | | Young's Modulus (kPa) | |
|---|---|---|---|---|
| | Average | Std. Dev. | Average | Std. Dev. |
| PEG-DA | | | 72.3 | 7.69 |
| PEG-DA + 1+ | 15.0 | 0.25 | 47.4** | 8.63 |
| PEG-DA + 7+ | 14.5 | 0.056 | 51.4** | 9.91 |

+33 mol % in the precursor solution
*Determined from DOPA assay
**p < 0.001 relative to PEG-DA gels These modulus values are about 30% lower than that of PEG-DA gels, confirming the inhibitory effect of DOPA on radical photopolymerization. Despite the decrease in modulus compared to PEG-DA gels, DOPA-containing gels still exhibited moduli suitable for many biomedical applications. A suitable modulus is one greater than 500 Pa. Another use of the adhesive hydrogels is for localized drug delivery. For example, adhesive hydrogels can be formed on a mucous membrane in the mouth or oral cavity. The hydrogels can be loaded with a drug such as an antibiotic and facilitate slow release of the drug over a period of time. They hydrogel can also be loaded with an analgesic and used to deliver pain relief at a localized site. They hydrogel can also be loaded with a chemotherapy drug and inserted into malignant tissue to deliver localized cancer therapy. The hydrogel can also be loaded with a cell proliferation inhibitor therapeutic drug and used as a coating stent or other vascular device and used to control cell proliferation at the site of an implant of the vascular device.

A tissue adhesive hydrogel capable of being cross-linked in vivo can be used as a tissue sealant for replacing metal or plastic sutures. The adhesive bends to the surrounding tissue at a surgical or injury site and the polymer forms a cohesive link to close the wound. The hydrogel can also be used for repair of bone fractures and cartilage to bone damage.

Other Uses

There are various industrial product uses of these coatings and hydrogels including prevention of marine biofouling (attachment of algae, bacteria, and mussels to surfaces underwater), prevention of bacteria contamination of water streams to industrial plants such as electronic and drug manufacturers, prevention of bacterial contamination of drinking water streams, dental and denture adhesives, underwater adhesives to deliver indicators, coatings for water purity and measurement sensors, paints used for prevention of biofouling.

There are also a number of consumer product and cosmetic uses of these coatings and hydrogels including without limitation use in dental and denture adhesives, use in cosmetics for adhesive to hair, skin, and legs, use in cosmetics such as eye shadow, lip stick, and mascara, use in application of temporary tattoos, and use as resealable adhesives for bags and containers.

Without limitation to any particular synthetic scheme or method of preparation, suitable compositions of this invention can include but are not limited to a urethane moiety between each such terminal monomer and DOPA residue. As described more fully below, such a moiety is a synthetic artifact of the agent/reagent utilized to couple the DOPA residue with the polymeric component. Within the broad aspects of this invention, various other moieties are contemplated, as would be understood by those skilled in the art made aware of this invention, depending upon terminal monomer functionality and choice of coupling agent.

EXAMPLES

General Description

The following non-limiting examples and data illustrate various aspects and features relating to the compositions and/or methods of the present invention, including the production of various polymeric or co-polymeric compositions having incorporated therein one or more DHPD components, as are available through the synthetic methodology described herein. While the utility of this invention is illustrated through the use of several polymeric or co-polymeric systems, it will be understood by those skilled in the art that comparable results are obtainable with various other compositions and/or methods for preparation, as are commensurate with the scope of this invention.

$PEO_{100}PPO_{65}PEO_{100}$ (PLURONIC® F127, avg. $M_w$=12,600), $PEO_{78}PPO_{30}PEO_{78}$ (PLURONIC® F68, avg. $M_w$=8,400), PEG (avg. $M_w$=8000), pentafluorophenol, 1,3-dicyclohexylcarbodiimide (DCC), 4,7,10-trioxa-1,13-tridecanediamine, fluorescein sodium salt ($FNa_2$), and ascorbic acid (AA) were purchased from Sigma (St. Louis, Mo.). L-DOPA, thionyl chloride, methacroyloyl chloride, t-butyldimethylsilyl chloride (TBDMS-Cl), di-t-butyl dicarbonate, methacrylic anhydride, 2,2'-dimethoxy-2-phenyl-acetonephenone (DMPA), acryloyl chloride, 1,8-diazabicyclo[5.4.0]undec-7-ene (DBU), tetrabutylammonium fluoride (TBAF), 4-(dimethylamino)-benzoic acid (DMAB), 1-vinyl-2-pyrrolidone (VP), N,N-disuccinimidyl carbonate, sodium borate, sodium molybdate dihydrate, sodium nitrite, 4-(dimethylamino)pyridine (DMAP), N-hydroxysuccinimide, N,N-diisopropylethylamine, dimethylformamide, and dichloromethane were purchased from Aldrich (Milwaukee, Wis.). Camphorquinone (CQ) was obtained from Polysciences, Inc. (Warrington, Pa.). Acetone was dried over 4 Å molecular sieve and distilled over $P_2O_5$ prior to use. Triethylamine was freshly distilled prior to use. All other chemical reagents were used as received.

L-DOPA methyl ester hydrochloride was prepared according to the procedure of Patel and Price, *J. Org. Chem.*, 1965, 30, 3575, which is incorporated herein by reference. Succinimidyl propionate activated PEG (mPEG-SPA, avg. $M_w$=5000) was obtained from Shearwater Polymers, Inc. (Huntsville, Ala.). Ethyl acetate saturated with HCl was prepared by bubbling HCl gas through ethyl acetate (50 mL) for approximately 10 minutes. 3,4-Bis(t-butyldimethylsiloxyl) L-phenylalanine $(DOPA(TBDMS)_2)$ and 3,4-bis(t-butyldimethylsiloxyl-N-t-butoxycarbonyl-L-phenylalanine (Boc-DOPA$(TBDMS)_2$) were synthesized according to the method of Sever and Wilker, *Tetrahedron*, 2001, 57, (29), 6139-6146, which is incorporated herein by reference.

Glass coverslips (12 mm dia.) used in the following examples were cleaned by immersing in 5% Contrad70 solution, a detergent which is an emulsion of anionic and nonionic surfactants in an allealtine aqueous base (Decon Labs, Inc., Bryn Mawr, Pa.) in an ultrasonic bath for 20 minutes, rinsed with deionized (DI) $H_2O$, sonicated in DI $H_2O$ for 20 minutes, rinsed in acetone, sonicated in acetone for 20 minutes, rinsed in hexanes, sonicated in hexanes for 20 minutes, rinsed in acetone, sonicated in acetone for 20 minutes, rinsed in DI $H_2O$, and sonicated in DI $H_2O$ for 20 minutes. The coverslips were subsequently air-dried in a HEPA-filtered laminar flow hood. To create pristine gold substrates, clean coverslips were sputtered (Cressington 208HR) with 2 nm Cr followed by 10 nm Au (99.9% pure).

Titanium oxide ($TiO_2$) surfaces were prepared by electron beam physical evaporation onto silicon (Si) wafer and cleaned in a plasma chamber prior to testing. Si wafers (MEMC Electronic Materials, St. Peters, Mo., surface orientation (100)) were coated with 100 nm Ti by an Edwards FL400 electron beam evaporator at <$10^{-6}$ Torr. The Si wafer was then cut into 8 mm×8 mm pieces which were subsequently cleaned by ultrasonication in the following media: 5% Contrad70, ultrapure water (ultrapure water is deionized and distilled), acetone, and petroleum ether. The substrates were further cleaned in an oxygen plasma chamber (Harrick Scientific, Ossining, N.Y.) at <200 mTorr and 100 W for 3 minutes.

Both pristine and modified gold surfaces were characterized, as described below, by X-ray photoelectron spectroscopy (XPS). XPS data was collected on an Omicron ESCALAB (Omicron, Taunusstein, Germany) configured with a monochromated A1Kα (1486.8 eV) 300-W X-ray source, 1.5 mm circular spot size, a flood gun to counter charging effects, and an ultrahigh vacuum (<$10^{-8}$ Torr). The takeoff angle, defined as the angle between the substrate normal and the detector, was fixed at 45°. Substrates were mounted on standard sample studs by means of double-sided adhesive tapes. All binding energies were calibrated using either the $Au(4f_{7/2})$ gold peak (84.0 eV) or the C(1s) carbon peak (284.6 eV). Analysis consisted of a broad survey scan (50.0 eV pass energy) and a 10-minute high-resolution scan (22.0 eV pass energy) at 270-300 eV for C(1s). Peak deconvolution and atomic percent calculations were performed with EIS analysis software.

Secondary ion spectra were collected on a TRIFT III™ time-of flight secondary ion mass spectrometer (TOF-SIMS) (Physical Electronics, Eden Prairie, Minn.) in the mass range 0-2000 m/z. A Ga$^+$-source was used at a beam energy of 15 keV with a 100 μm raster size. Both positive and negative spectra were collected and calibrated with a single set of low mass ions using the PHI software Cadence.

To determine relative hydrophilic/hydrophobic nature of the surfaces, contact angle data was collected, as described below, by the sessile drop method. A custom-built contact angle goniometer (components from Rame-Hart, Mountain Lakes, N.J.) equipped with a humidified sample chamber was used to measure both advancing and receding contact angles of ultrapure water (18.2 MΩ-cm; Barnstead, Dubuque, Iowa) on unmodified and modified substrates. For each surface, four measurements were made at different locations and the mean and standard deviation were reported.

Surface Plasmon Resonance (SPR) measurements were made on a BIACORE 2000 (Biacore International AB; Uppsala, Sweden) using bare gold sensor cartridges. The resonance response was calibrated using 0-100 mg/ml NaCl solutions. Dilute solutions (0.1 mM in H$_2$O) of mPEG-DOPA, mPEG-MAPd, and mPEG-OH were injected into the SPR flow cell for 10 minutes after which flow was switched back to pure DI H$_2$O. In a separate experiment to measure protein adsorption to modified substrates, sensor surfaces with preformed PEG films were exposed to 0.1 mg/ml bovine serum albumin (BSA) solution in 10 mM HEPES buffer (0.15 M NaCl, pH=7.2), and subsequently pure buffer.

For use in demonstration of anti-fouling effects, NIH 3T3-Swiss albino fibroblasts obtained from ATCC (Manassas, Va.) were maintained at 37° C. and 10% CO$_2$ in Dulbecco's modified Eagle's medium (DMEM; Cellgro, Herndon, Va.) containing 10% (v/v) fetal bovine serum (FBS) and 100 U/ml of both penicillin and streptomycin.

RP-HPLC preparation was performed using a Waters HPLC system (Waters, Milford, Mass.) on a Vydac 218TP reverse phase column with a gradient of acetonitrile/0.1% trifluoroacetic acid (v/v) water. ESI-MS analysis was performed on a LCQ LC-MS system (Finnigan, Thermoquest, Calif.). MALDI-TOF MS analysis was performed on a Voyager DE-Pro mass spectrometer (Perseptive Biosystem, Mass.). α-Cyano-4-hydroxycinnaminic acid was used as a matrix. NiTi alloy (10 mm×10 mm×1 mm) was obtained from Nitinol Devices & Components (Fremont, Calif.). Si, SiO$_2$ (1500 Å thermal oxide), and GaAs wafers were purchased from University Wafer (South Boston, Mass.).

With regard to the following cell adhesion tests and/or spreading assays, modified and unmodified substrates were pretreated in 12-well TCPS plates with 1.0 ml of DMEM containing 10% FBS for 30 minutes at 37° C. and 10% CO$_2$. Fibroblasts of passage 12-16 were harvested using 0.25% trypsin-EDTA, resuspended in DMEM with 10% FBS, and counted using a hemocytometer. Cells were seeded at a density of 2.9×10$^3$ cell/cm$^2$ by diluting the suspension to the appropriate volume and adding 1 ml to each well. The substrates were maintained in DMEM with 10% FBS at 37° C. and 10% CO$_2$ for 4 hours, after which time unattached cells were aspirated. Adherent cells on the substrates were fixed in 3.7% paraformaldehyde for 5 minutes and subsequently treated with 5 μM 1,1'-dioctadecyl-3,3,3',3'-tetramethylindocarbocyanine perchlorate (DiI; Molecular Probes, Eugene, Oreg.) in DMSO for 30 minutes at 37° C. The stain was then aspirated and substrates were washed (3×) with DMSO for 10 minutes and mounted on glass slides using Cytoseal (Stephens Scientific, Kalamazoo, Mich.) to preserve fluorescence. These experiments were performed in triplicate for statistical purposes. For electron microscopy, some samples were dehydrated with EtOH after fixing, critical-point dried, and sputtered with 3 nm Au.

To quantify cell attachment, substrates were examined with an Olympus BX-40 ($\lambda_{Ex}$=549 nm, $\lambda_{Em}$=565 nm) and color images were captured with a Coolsnap CCD camera (Roper Scientific, Trenton, N.J.). Five images were taken from each of the three substrate-replicates. The resulting images were quantified using thresholding in MetaMorph (Universal Imaging, Downington, Pa.). A one-way ANOVA and Tukey's post-hoc test with 95% confidence intervals (SPSS, Chicago, Ill.) were used to determine statistical significance of the data. The mean and standard deviation of the measurements were reported.

Example 1

Synthesis of Succinimidyl Carbonate PAO, SC-PAO7

PLURONIC® F127 (0.60 mmols) was dissolved in 30 mL of dry dioxane. N,N'-Disuccinimidyl carbonate (6.0 mmols) in 10 mL dry acetone was added. DMAP (6.0 mmols) was dissolved in 10 mL dry acetone and added slowly under magnetic stirring. Activation proceeded 6 hours at room temperature, after which SC-PAO7 was precipitated into ether. The disappearance of the starting materials during the reaction was followed by TLC in chloroform-methanol (5:1) solvent system. The product was purified by dissolution in acetone and precipitation with ether four times. The product yield was 65%. $^1$H NMR (500 MHz, CDCl$_3$): δ ppm 0.96-1.68 (br, —OCHCH$_3$CH$_2$O—), 2.80 (s, —COON(CO)$_2$(CH$_2$)$_2$), 3.15-4.01 (br, —OCH$_2$CH$_2$O—; —OCH CH$_3$CH$_2$O—), 4.40 (s, —OCH$_2$CH$_2$OCOON(CO)$_2$CH$_2$CH$_2$—).

Example 2

Synthesis of DME-PAO7

A slurry of DOPA methyl ester hydrochloride (1.25 mmols) and triethylamine (2.5 mmols) was mixed with SC-PAO7 (0.16 mmols) in 10 mL chloroform. The disappearance of the starting materials during the reaction was followed by TLC in chloroform-methanol-acetic acid (5:3:1) solvent system. After stirring for 1 hour at room temperature, the solvent was evaporated off, and DME-PAO7 was purified by precipitation from cold methanol three times. DME-PAO7 gave a positive Arnow test indicating the presence of catechol hydroxyl groups. The product yield was 75%. $^1$H NMR (500 MHz, CDCl$_3$): δ ppm 0.98-1.71 (br, —OCHCH$_3$CH$_2$O—), 2.83-3.06 (m, —NHCHCH$_2$C$_6$H$_3$(OH)$_2$COOCH$_3$), 3.15-4.02 (br, —OCH$_2$CH$_2$O—; —NHCH(CH$_2$C$_6$H$_3$(OH)$_2$COOCH$_3$), 4.05-4.35 (d, —OCH$_2$CH$_2$OCONH CHCH$_2$C$_6$H$_3$(OH)$_2$COOCH$_3$), 4.55 (br, —NHCHCH$_2$C$_6$H$_3$(OH)$_2$COOCH$_3$), 5.30 (d, —NHCHCH$_2$C$_6$H$_3$(OH)$_2$COO CH$_3$), 6.45-6.80 (1s, 2d, —NHCHCH$_2$C$_6$H$_3$(OH)$_2$COO CH$_3$).

Example 3

Synthesis of DOPA-PAO7

L-DOPA (1.56 mmols) was added to 30 mL 0.1 M Na$_2$B$_4$O$_7$ (pH=9.32) aqueous solution under Ar atmosphere, followed by stirring at room temperature for 30 minutes. SC-PAO7 (0.156 mmols) in 5 mL acetone was added to the resulting mixture and stirred overnight at room temperature. The solution pH was maintained with sodium carbonate during the reaction. The disappearance of the starting materials during the reaction was followed by TLC in chloroform-methanol-acetic acid (5:3:1) solvent system. The solution was acidified to pH 2 with concentrated hydrochloric acid and then extracted three times with dichloromethane. The combined dichloromethane extracts were dried with anhydrous sodium sulfate and filtered, and dichloromethane was evaporated. The product was further purified by precipitation from cold methanol. DOPA-PAO7 gave a positive Arnow test indicating the presence of catechol hydroxyl groups. The product yield was 52%. $^1$H NMR (500 MHz, CDCl$_3$): δ ppm 0.92-1.70 (br, —OCHCH$_3$CH$_2$O—), 2.91-3.15 (m, —NHCHCH$_2$C$_6$H$_3$(OH)$_2$COOCH), 3.20-4.10 (br, —OCH$_2$CH$_2$O—; —OCHCH$_3$CH$_2$O—), 4.1-4.35 (d, —OCH$_2$CH$_2$OCONHCHCH$_2$C$_6$H$_3$(OH)$_2$COOH), 4.56 (m, —NHCHCH$_2$C$_6$H$_3$(OH)$_2$COOH), 5.41 (d, —NHCHCH$_2$C$_6$H$_5$(OH)$_2$COOH), 6.60-6.82 (1s, 2d, —NHCHCH$_2$C$_6$H$_3$(OH)$_2$COOH).

Example 4

Synthesis of Succinimidyl Carbonate PAO8, SC-PAO8

A procedure similar to that described above for the synthesis and purification of SC-PAO7 was used to prepare SC-PAO8. The product yield was 68%. $^1$H NMR (500 MHz, CDCl$_3$): δ ppm 0.95-1.58 (br, —OCHCH$_3$CH$_2$O—), 2.80 (s, —COON(CO)$_2$(CH$_2$)$_2$), 3.10-4.03 (br, —OCH$_2$CH$_2$O—; —OCHCH$_3$CH$_2$O—), 4.40 (s, —OCH$_2$CH$_2$OCOON(CO)$_2$CH$_2$CH$_2$).

Example 5

Synthesis of DME-PAO8

A procedure similar to that described above for the synthesis and purification of DME-PAO7 conjugate was used to make DME-PAO8. The product yield was 76%. $^1$H NMR (500 MHz, CDCl$_3$): δ ppm 0.98-1.50 (br, —OCHCH$_3$CH$_2$O—), 2.85-3.10 (m, —NHCHCH$_2$C$_6$H$_3$(OH)$_2$COOCH$_3$), 3.15-4.01 (br, —OCH$_2$CH$_2$O—; —OCHCH$_3$CH$_2$O—; —NHCH(CH$_2$C$_6$H$_3$(OH)$_2$COOCH$_3$), 4.03-4.26 (d, —OCH$_2$CH$_2$OCONHCHCH$_2$C$_6$H$_3$(OH)$_2$COOCH$_3$), 4.55 (m, —NHCHCH$_2$C$_6$H$_3$(OH)$_2$COOCH$_3$), 5.30 (d, —NHCHCH$_2$C$_6$H$_3$(OH)$_2$COOCH$_3$), 6.45-6.77 (1s, 2d, —NHCHCH$_2$C$_6$H$_3$(OH)$_2$COOCH$_3$).

Example 6

Synthesis of DOPA-PAO8

A procedure similar to that described above for the synthesis of DOPA-PAO7 conjugate was used to prepare and purify DOPA-PAO8. The product yield was 49%. $^1$H NMR (500 MHz, CDCl$_3$): δ ppm 0.92-1.50 (br, —OCHCH$_3$CH$_2$O—), 2.91-3.10 (m, —NHCHCH$_2$C$_6$H$_3$(OH)$_2$COOH), 3.15-3.95 (br, —OCH$_2$CH$_2$O—; —OCHCH$_3$CH$_2$O—), 4.06-4.30 (d, —OCH$_2$CH$_2$OCONHCHCH$_2$C$_6$H$_3$(OH)$_2$COOH), 4.54 (m, —NHCHCH$_2$C$_6$H$_3$(OH)$_2$COOH), 5.35 (d, —NHCHCH$_2$C$_6$H$_5$(OH)$_2$COOH), 6.50-6.80 (1s, 2d, —NHCHCH$_2$C$_6$H$_3$(OH)$_2$COOH).

Example 7

Colorimetric Assay

Coupling efficiencies of DOPA methyl ester and DOPA to PLURONICs® F127 and F68 were determined using the colorimetric method of Waite and Benedict. Briefly, samples were analyzed in triplicate by diluting aliquots of standards or unknown solutions with 1 N HCl to a final volume of 0.9 mL. 0.9 mL of nitrite reagent (1.45 M sodium nitrite and 0.41 M sodium molybdate dihydrate) was added to the DOPA solution, followed immediately by the addition of 1.2 mL of 1 N NaOH. Due to time-dependent changes in absorbance intensity, care was taken to ensure that the time between the addition of NaOH and recording of the absorbance was 3 minutes for all standards and samples. The absorbance was recorded at 500 nm for all standards and samples. DOPA was used as the standard for both the DOPA methyl ester and DOPA conjugates.

Example 8

Rheology

Rheological measurements of the gelation process were performed using a Bohlin VOR Rheometer (Bohlin Rheologi, Cranbury, N.J.). A 30 mm diameter stainless steel cone and plate geometry with a cone angle of 2.5 degrees was used for all measurements. The temperature was controlled by a circulating water bath. Samples were cooled in the refrigerator prior to transfer of 0.5 mL of liquid solution to the apparatus. Measurements of storage and loss moduli, G' and G", were taken in the oscillatory mode at 0.1 Hz and a strain of 0.45%. The heating rate was 0.5° C./min except in the vicinity of the gelation temperature, when it was reduced to 0.1° C./min. The strain amplitude dependence of the viscoelastic data was checked for several samples, and measurements were only performed in the linear range where moduli were independent of strain amplitude. Mineral oil was applied to a ring surrounding the outer surfaces of the sample compartment to prevent dehydration during measurements.

Example 9

Differential Scanning Calorimetry (DSC)

DSC measurements were performed on a TA Instruments DSC-2920 (TA Instruments, New Castle, Del.) calorimeter. Spectra were obtained for three samples of each concentration on heating and cooling cycle. Sample volumes of 20 μl in hermetically sealed aluminum pans were used and scans were recorded at a heating and cooling rate of 3° C./min with an empty pan as reference.

Example 10a

Amino-terminated methoxy-PEG, mPEG-NH$_2$ (2.0 g, 0.40 mmoles, M$_w$=2,000 or 5,000, Sun-Bio PEGShop), N-Boc-L-DOPA dicyclohexylammonium salt (0.80 mmoles), HOBt (1.3 mmoles), and Et$_3$N (1.3 mmoles) were dissolved in 20 mL of a 50:50 mixture of dichloromethane (DCM) and DMF. HBTU (0.80 mmoles) in 10 mL of DCM was then added, and the reaction was carried out under argon at room temperature for 30 minutes. The reaction solution was successively washed with saturated sodium chloride solution, 5% NaHCO$_3$, diluted HCl solution, and distilled water. The crude product was concentrated under reduced pressure and purified by column chromatography on Sephadex® LH-20 with methanol as the mobile phase. The product, mPEG-DOPA, was further purified by precipitation in cold methanol three times, dried in vacuum at room temperature, and stored under nitrogen at −20° C. $^1$H NMR (500 MHz, CDCl$_3$/TMS): δ 6.81-6.60 (m, 3H, C$_6$H$_3$(OH)$_2$—), 6.01 (br, s, 1H, OH—), 5.32 (br, s, 1H, OH—), 4.22 (br, s, 1H, C$_6$H$_3$(OH)$_2$—CH$_2$—CH(N—)—C(O)N—), 3.73-3.38 (m, PEO), 3.07 (m, 2H, PEO-CH2—NH—C(O)—), 2.73 (t, 2H, C$_6$H$_3$(OH)$_2$—CH$_2$—CH(N—)—C(O)N—), 1.44 (s, 9 H, (CH$_3$)$_3$C—), 1.25 (s, 3 H, CH$_3$CH$_2$O—).

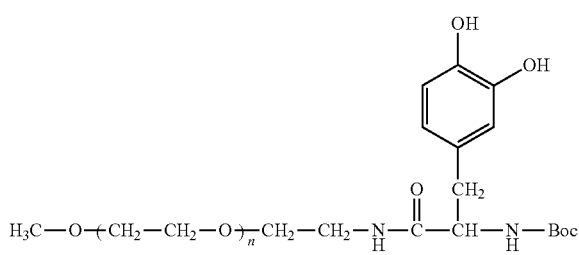

Example 10b

The synthesis and related procedures of the preceding example can be extended, by analogy, using other DOPA-containing peptides and oligopeptides, whether natural or synthetic in origin. Depending upon a particular synthetic sequence, use of an N-terminal protecting group may be optional. As referenced above, various other DOPA-like adhesive components can also be utilized, as would be well-known to those skilled in the art made aware of this invention. For instance, B-amino acids and N-substituted glycine DOPA analogs can be used.

Regardless of a particular DHPD adhesive component, a variety of polymeric components can be used in accordance with the synthetic techniques and procedures described above. The polymeric component can vary in molecular weight limited only by corresponding solubility concerns. As mentioned above, a variety of other polymers can be used for surface anti-fouling and/or particle stabilization, such polymers including but not limited to hyaluronic acid, dextrans and the like. Depending upon solubility requirements and desired surface effect, the polymeric component can be branched, hyperbranched or dendrimeric, such components available either commercially or by well-known synthetic techniques.

While the composition of Example 10a is the amidation product of the referenced starting materials, it should be understood that comparable polymer-DHPD conjugates can be prepared coupling the N-terminus of a DHPD component to an end group, back bone or side chain of a suitably functionalized natural or synthetic polymer, including those described above. For example, and without limitation, as illustrated above, a suitable polymeric component terminating with a carbonate functionality can be used to provide the desired conjugate by reaction with the N-terminus of the desired DHPD component.

Example 11a

The consensus decapeptide repeat sequence (mussel adhesive protein decapeptide, MAPd, $NH_2$-Ala-Lys-Pro-Ser-Tyr-Hyp-Thr-DOPA-Lys-$CO_2H$) of the blue mussel *Mytilus edulis* foot protein 1 (Mefp 1) was synthesized by solid phase peptide synthesis on Rink resin (0.6 mMol/g) using Fmoc protected amino acids, BOP, HOBt, and DIEA as activating agents, and NMP as solvent. Fmoc deprotection was performed using a 25% piperidine solution in NMP for twenty minutes. Couplings of amino acids were performed using two equivalents of the Fmoc-amino acid BOP:HOBt:DIEA in a 1:1:1:1 ratio for twenty minutes, with an initial, ten-minute preactivation step. Upon completion of the decapeptide, the free amine terminus of the decapeptide was coupled to activated methoxy-PEG-$CO_2H$ (mPEG-SPA, $M_w$=2k or 5k, Shearwater Polymers) using carbodiimide chemistry. The PEG-decapeptide conjugates (mPEG-MAPd, 2k or 5k) were cleaved at 0° C. for two hours using 1 M TMSBr in TFA, with EDT, thioanisole, and m-cresol. The crude mPEG-MAPd products were precipitated in ether at 0° C., and purified by preparative HPLC using a Vydac 218TP reverse phase column (220×22 mm×10 µm). The purity of the products was determined to be >90% using analytical HPLC, and the structures confirmed using a PerSeptive Biosystem MALDI-TOF-MS.

Example 11b

The synthesis and procedures of Example 11a can be extended analogously to and consistent with the variations illustrated in Example 10b. In addition, other conjugates can be prepared using DOPA-containing polymers prepared by enzymatic conversion of tyrosine residues therein. Other techniques well-known in the field of peptide synthesis can be used with good effect to provide other desired protein sequences, peptide conjugates and resulting adhesive/anti-fouling effects.

Example 12a

Gold surfaces were modified by adsorption of mPEG-DOPA or mPEG-MAPd (2k, 5k) from solution in DCM or phosphate-buffered saline (PBS; pH=3, 7.4, and 11) at polymer concentrations ranging from 0.1-75 mg/ml. Substrates were placed in a vial and immersed in mPEG-DOPA or mPEG-MAPd solution for up to 24 hours without agitation. Upon removal from solution, substrates were rinsed with the appropriate solvent (DCM or DI $H_2O$) to remove unbound polymer, and dried in vacuo. For comparison, identical surface modifications were performed using PEG-monomethylether (mPEG-OH, avg. $M_w$=5000). Alternatively, a drop of solution containing mPEG-DOPA or mPEG-MAPd (10 mM in PBS, PEG molecular weight=2000) was incubated on a Au-coated glass coverslip (Au thickness ~10 nm) for 30 minutes at 37° C., after which the surface of the coverslip was rinsed (3×) with PBS. Analysis of the modified surfaces by advancing/receding contact angle, XPS, and TOF-SIMS revealed the formation of a chemisorbed layer of mPEG-DOPA or mPEG-MAPd.

Figures 7A, 7B, 7C:
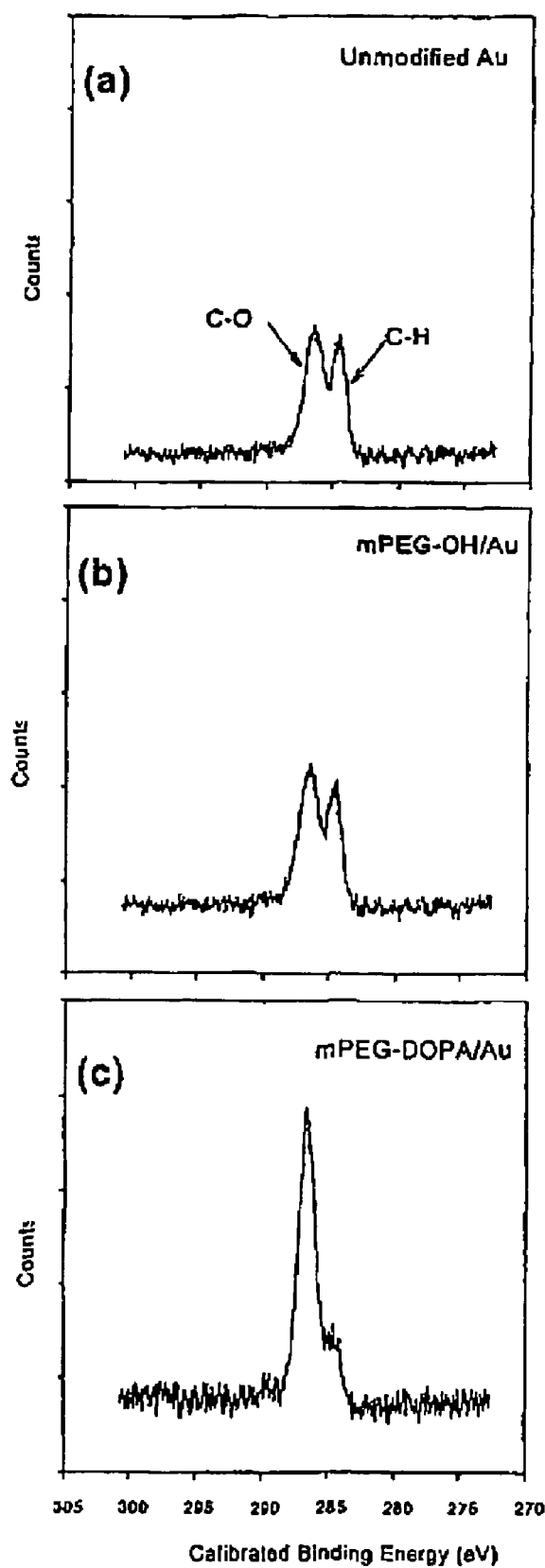
FIGS. 7A-C show high-resolution C(1s) XPS peaks for (A) un-modified Au, (B) m-PEG-OH, and (C) m-PEG-DOPA. A dramatic increase in the ether peak at 286.5 eV in (C) indicated the presence of PEG.

FIGS. 7A-C shows the XPS spectra for the unmodified, mPEG-OH modified, and mPEG-DOPA modified surfaces. As expected, the ether peak at 286.5 eV increased only slightly with the mPEG-OH treatment, while a dramatic increase was observed after adsorption of mPEG-DOPA, indicating a large presence of ether carbons. An ether peak from a pure PEG with the same binding energy has been reported in the literature. The smaller peak at 285.0 eV in FIG. 7 can be attributed to the aliphatic and aromatic carbons in the PEG and DOPA headgroup, as well as some hydrocarbon contamination resulting from the preparation/evacuation process.

Time-of-flight SIMS data corroborated the XPS findings. TOF-SIMS analysis was carried out on unmodified and mPEG-DOPA-modified Au substrates, as well as mPEG-DOPA powder and a gold substrate exposed to mPEG-OH. Data was collected from each substrate for about 4 minutes.

Figure 8A:
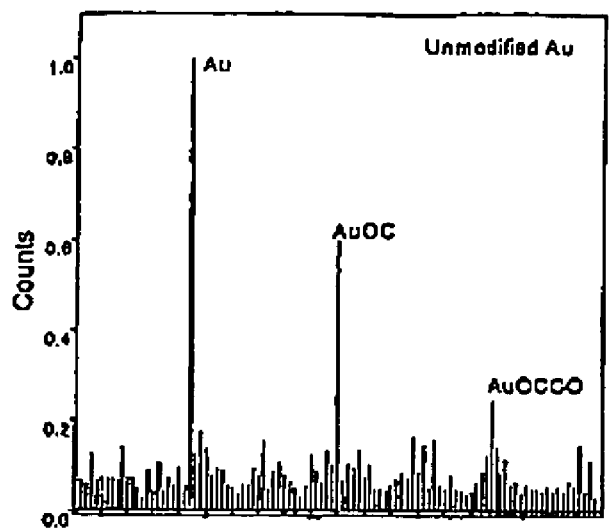
FIGS. 8A-C provide TOF-SIMS positive spectrum showing peaks representing catechol binding of gold. Spectra were normalized to Au peak (m/z~197).
Figure 8B:
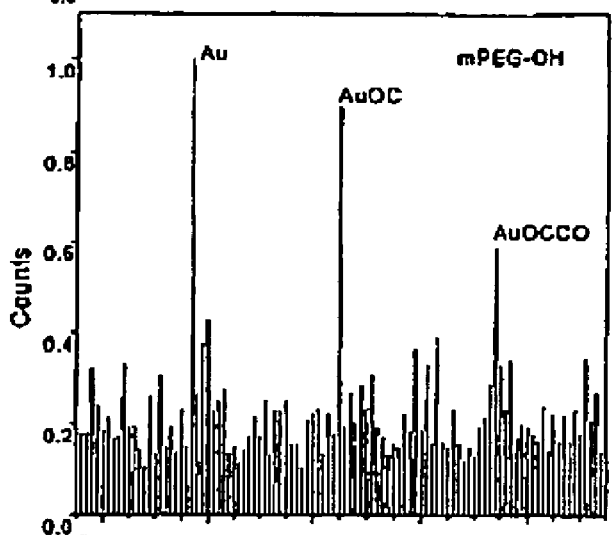
Figure 8C:
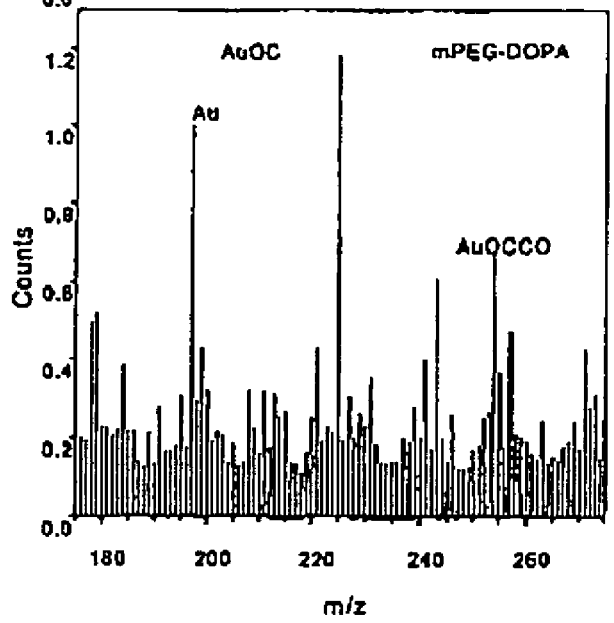

The positive ion spectrum of unmodified Au exhibits $(C_nH_{2n+1})^+$ and $(C_nH_{2n-1})^+$ peaks, typical for hydrocarbon contamination (data not shown). Additional minor contaminants were present, including $NH_4^+$, $Na^+$, and relatively small amounts of $C_aH_bO_c^+$ species. Because of the process used to deposit the Au film, a peak for Cr was seen at m/z~52, in addition to the Au peak at m/z~196.9. Exposing the gold surfaces to mPEG-OH resulted in only modest increases in the peaks representing $C_aH_bO_c^+$ PEG fragments, which are likely attributable to contamination or non-specific absorption of mPEG-OH. This is evidenced by the peaks at m/z~225 (AuOC$^+$) and 254 (AuOCCO$^+$) which did not show dramatic increases when compared to substrates modified with mPEG-DOPA. (FIGS. 8A-C).

Figure 9:
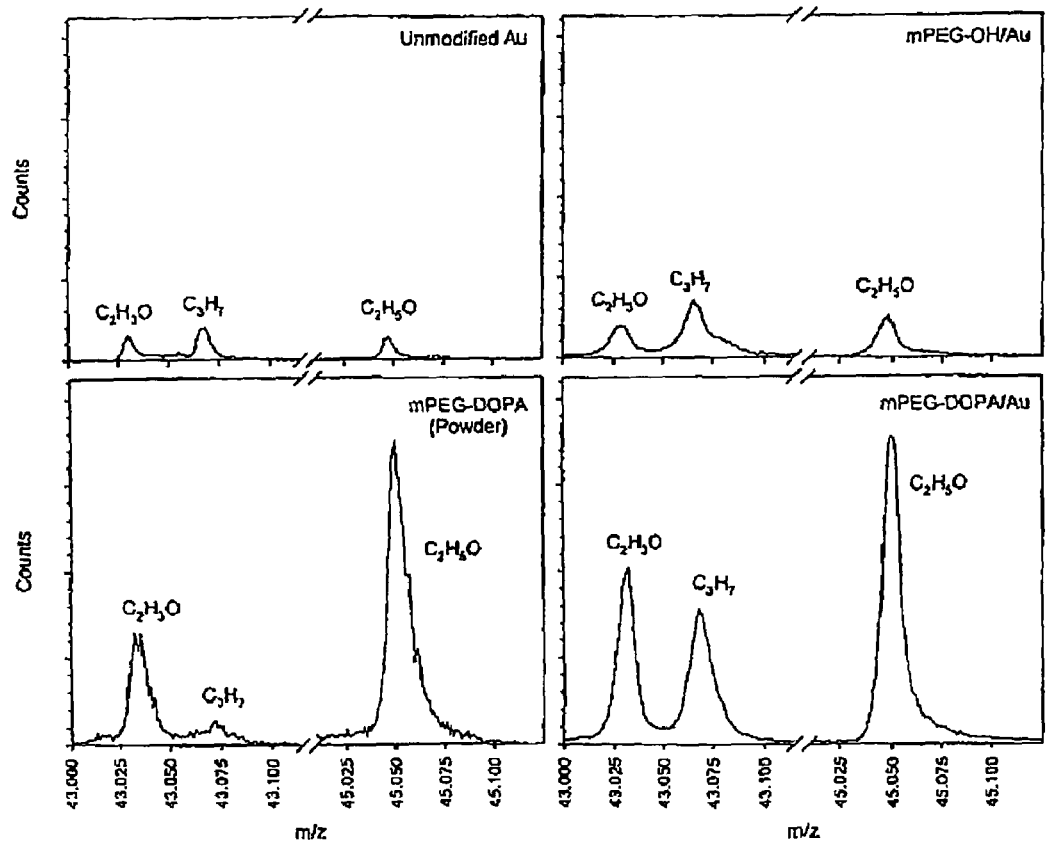
FIG. 9 provides TOF-SIMS spectra showing the positive secondary ion peak at mass m/z~43 for unmodified Au substrate, Au exposed to mPEG-OH, mPEG-DOPA powder and Au exposed to mPEG-DOPA.

The positive ion spectrum of the Au surface modified with mPEG-DOPA was dominated by the presence of $C_aH_bO_c^+$ peaks representing the adsorbed molecule. As illustrated in FIG. 9, the relative abundance of $C_2H_3O^+$ and $C_2H_5O^+$ increased with respect to unmodified and mPEG-OH modified surfaces. There was also a dramatic increase in the relative abundance of $C_3H_7^+$ (m/z~43) and $C_4H_5^+$ (m/z~53), as well, which can likely be attributed to hydrocarbon contamination or the fragmentation of the t-butyl in the Boc protection group.

Figure 10:
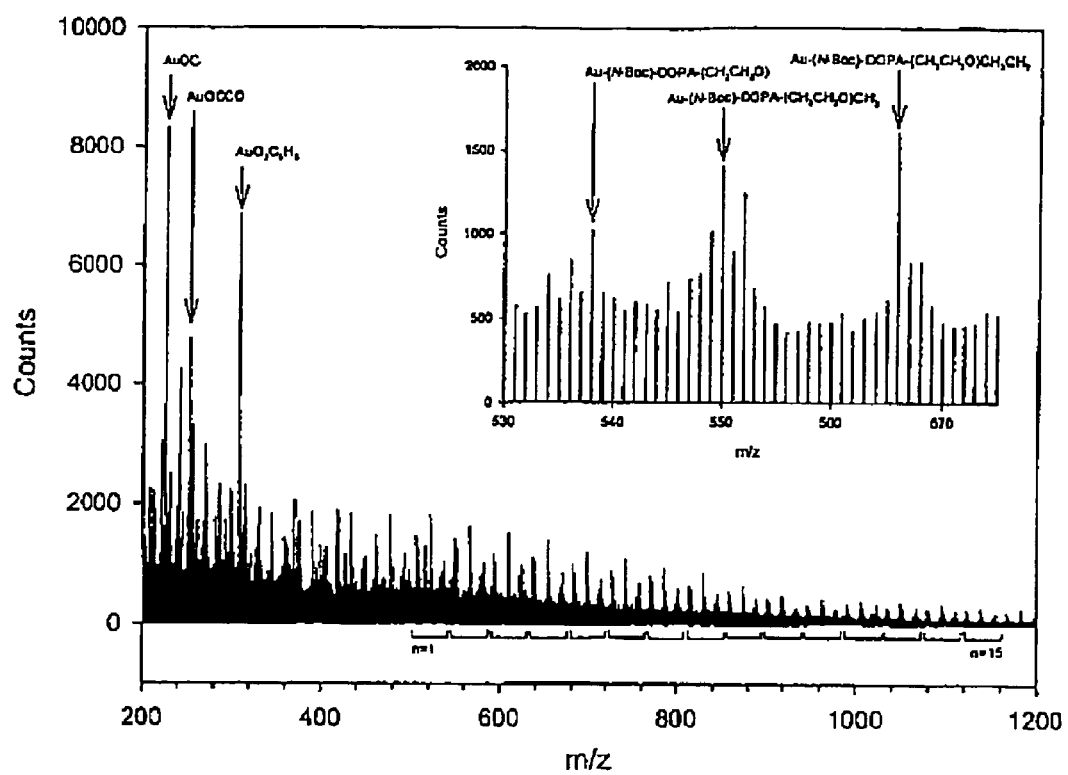
FIG. 10 shows TOF-SIMS spectra showing the positive secondary ion peaks for Au substrate chemisorbed with mPEG-DOPA. Catecholic binding of gold is observed at m/z~225 (AuOC), 254 (AuOCCO), and 309. Less intense $AuO_aC_b$ peaks are seen at m/z~434, 450, 462, and 478. The periodic triplets seen in the m/z range 530-1150 correspond to Au bound to DOPA-$(CH_2CH_2O)_n$, where each subpeak is separated by 14 or 16 amu, representing $CH_2$, $CH_2CH_2$, and $CH_2CH_2O$ in the PEG chain. This pattern was observed for n=1-15.

Perhaps the most notable feature of the positive ion spectrum of the PEGylated Au substrate were the patterned triplet repeats in the high mass range (FIG. 10). Each of these triplet clusters corresponds to an Au-DOPA-$(CH_2CH_2O)_n$ fragment. When further resolved, each subcluster within the triplet represents the addition of $CH_2$, $CH_2CH_2$, or $CH_2CH_2O$, as each of these peaks is about 14-16 amu apart. This repeat pattern was identifiable from n=0-15, beyond which the signal was below detectable limits.

In the negative ion spectra for the pristine Au surface, little of note was observed aside from the strong definable peaks for O$^-$, HO$^-$, and Au$_n^-$ for n=1-3 (data not shown). There was a small amount of hydrocarbon contamination present at m/z~13 (CH$^-$), 24 ($C_2H_2^-$), and 37 ($C_3H^-$). The negative ion spectrum of the PEGylated Au surface was dominated by the peak for $C_7H_{11}O_2^+$ at m/z~126.893. The presence of this peak at modest intensity in the spectrum of the mPEG-OH modified Au suggests that it represents a larger ethylene glycol fragment. The most interesting peaks lie in the high mass range (>200 m/z) and represent the coupling of catecholic oxygen to Au. The spectrum suggests that one Au atom can bind up to six oxygen atoms, corresponding to three DOPAs.

The contact angle data demonstrated a firm dependence on the character of the adsorption solvent used when modifying the gold films with mPEG-DOPA (data not shown). The surface modified in DCM showed a significantly lower θa than the unmodified surface (p<0.001) and the surfaces modified in all aqueous solutions (p<0.05). Generally speaking, as the pH of the aqueous solutions was increased, the hydrophilicity of the treated surfaces was decreased, indicating a diminished ability to PEGylate the surfaces, perhaps due to the propensity of DOPA to be oxidized to its less adhesive quinone form at elevated pH, an interpretation that is supported by previous studies that showed the unoxidized catechol form of DOPA is primarily responsible for adhesion.

Example 12b

Figure 11:
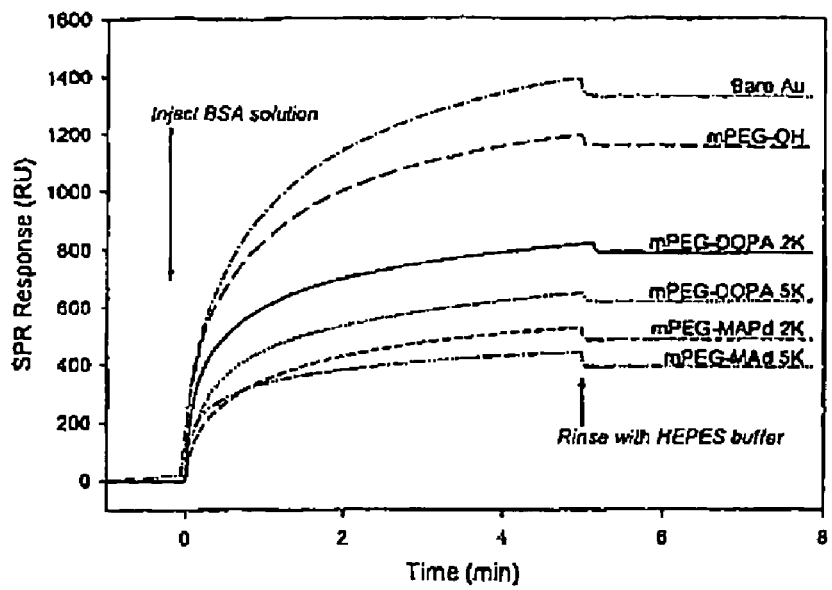
FIG. 11 shows SPR spectra of protein (0.1 mg/ml BSA) adsorption onto modified and unmodified gold surfaces. mPEG-DOPA and mPEG-MAPd modified surfaces exhibited reduced protein adsorption compared to bare gold and mPEG-OH modified surfaces.
Figure 12:
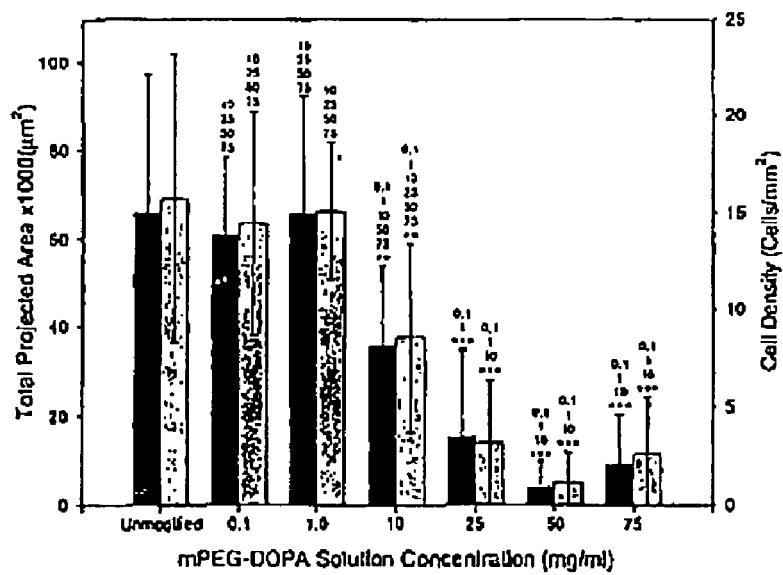
FIG. 12 shows mPEG-DOPA concentration dependence of anti-fouling behavior. Gold surfaces were modified for 24 h at the mPEG-DOPA concentrations indicated, followed by analysis of the density and area of attached cells. (*=p<0.05, =p<0.01, *=p<0.001; black bars=total proj. area, gray bars=surface cell density)
Figure 13:
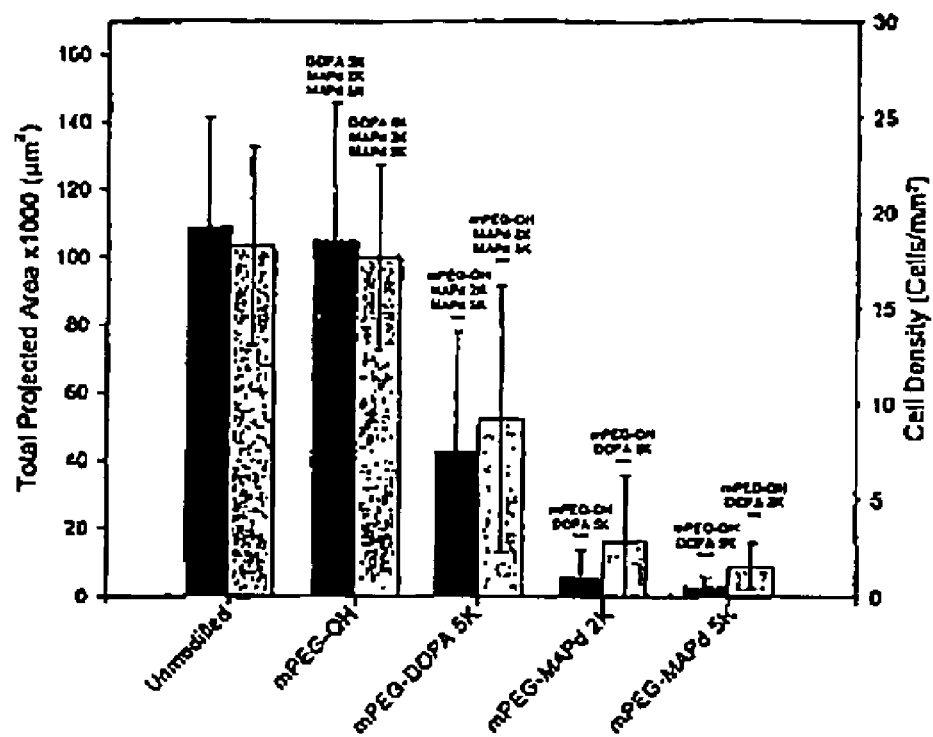
FIG. 13 compares cell attachment and spreading on bare gold, mPEG-OH-treated gold, and gold modified with mPEG-DOPA 5K, mPEG-MAPd 2K, and mPEG-MAPd 5K under optimal conditions (50 mg/ml for 24 h). (black bars=total proj. area, gray bars=surface cell density; ***=p<0.001)

Protein adsorption and attachment/spreading of cells onto untreated and treated coverslips were evaluated as follows. Surface plasmon resonance (SPR) experiments demonstrated that the DOPA-containing polymers were rapidly bound to the gold surface and the resulting modified surfaces possessed an enhanced resistance to protein adsorption (FIG. 11). Protein adsorption onto mPEG-MAPd (5k) modified gold was roughly 70% less than to the unmodified gold surface. Analysis of fibroblasts cultured on modified substrates showed a strong dependence of cell attachment on mPEG-DOPA concentration (FIG. 12), adsorption solvent, and modification time used during preparation of the PEG-modified substrates. Surfaces modified for 24 hours with >25 mg/ml mPEG-DOPA or mPEG-MAPd exhibited a statistically significant reduction in cell attachment and spreading (FIGS. 12-14). The mPEG-MAPd (5k) modified gold surface exhibited a 97% reduction in total projected cellular area and a 91% reduction in the density of cells attached to the surface.

Example 12c

The modification illustrated in Example 12a, optionally varied as referenced in Examples 10b and 11b, can be extended to other noble metals, including without limitation, silver and platinum surfaces. Such application can also be extended, as described herein, to include surface modification of any bulk metal or metal alloy having a passivating or oxide surface. For example, bulk metal oxide and related ceramic surfaces can be modified, as described herein. Such techniques can also be extended to semiconductor surfaces, such as those used in the fabrication of integrated circuits and MEMS devices, as also illustrated below in the context of nanoparticulate stabilization.

Example 13

Silicate glass surfaces (glass coverslips) were modified by adsorption of mPEG-MAPd (2k) from a 10 mM solution in water, using the method described in Example 12a. The cell density of NIH 3T3 cells attached to modified and unmodified glass surfaces were evaluated as described, above. Glass surfaces modified for 24 hours with mPEG-MAPd exhibited a 43% reduction in cell density compared to unmodified glass surfaces (Cell Density (cells/mm$^2$): 75.5+/−6.5 on unmodified glass; 42.7+/−9.8 on mPEG-MAPd modified glass).

Example 14a

To illustrate stabilization of metal oxides and, in particular, metal oxide nanoparticles, 50 mg of mPEG-DOPA (5k) was dissolved in water (18 MΩ-cm, Millipore) and combined with 1 mg of magnetite ($Fe_3O_4$) powder. Similar preparations were also prepared using a mPEG-NH$_2$ (5k) (Fluka) and a mPEG-OH (2k) (Sigma) as controls. Each of these aqueous solutions was sonicated using a Branson Ultrasonics 450 Probe Sonicator for one hour while being immersed in a 25° C. bath. The probe had a frequency of 20 kHz, length of 160 mm, and tip diameter of 4.5 mm. The sample was then removed and allowed to stand at room temperature overnight to allow any unmodified magnetite to precipitate out of solution. Suspensions prepared using the control polymers (mPEG-NH$_2$ and mPEG-OH) rapidly precipitated to yield a brown solid and clear, colorless supernatant. In samples prepared using PEG-DOPA stabilized nanoparticles, the sample was clear and brown. The clear brown supernatant was isolated and dialyzed for three days in water using Spectra/Por® membrane tubing (MWCO:15,000). Following dialysis, the sample was lyophilized and stored under vacuum at room temperature until used.

Example 14b mPEG-DOPA stabilized nanoparticles were characterized by transmission electron microscopy (TEM), thermogravimetric analysis (TGA), fourier transform infrared spectroscopy (FTIR), and UV/vis spectroscopy. TEM results demonstrated that the majority of nanoparticles were of diameter of 5-20 nm (data not shown). TGA analysis of 0.4 mg of mPEG- DOPA stabilized magnetite indicated that the particles contain 17% by weight mPEG-DOPA (data not shown). FTIR performed on untreated magnetite showed relatively little absorbance within the wavelength range from 4000-400 $cm^{-1}$, whereas the mPEG-DOPA treated nanoparticles exhibited absorption bands at 800-1600 $cm^{-1}$ and 2600-3200 $cm^{-1}$, confirming the presence of mPEG-DOPA.

Example 14c

The dry PEG-DOPA stabilized magnetite nanoparticles readily dispersed in aqueous and polar organic solvents (e.g., dichloromethane) to yield clear brown suspensions that were stable for months without the formation of noticeable precipitates. Suspensions of mPEG-DOPA stabilized nanoparticles in various solvents were prepared by dispersing 1 mg of mPEG-DOPA treated magnetite in 1 ml of water (18 MΩ-cm filtered using a Millex® AP 0.22 μm filter (Millipore)), DCM or Toluene. Suspensions were placed in a bath sonicator for ten minutes to disperse the nanoparticles. All three solutions were stable at room temperature for at least six months, whereas control suspensions of unmodified magnetite and magnetite stabilized by mPEG-OH or mPEG-$NH_2$ precipitated out in less than 24 hours in each solvent.

Example 14d

Figure 15:
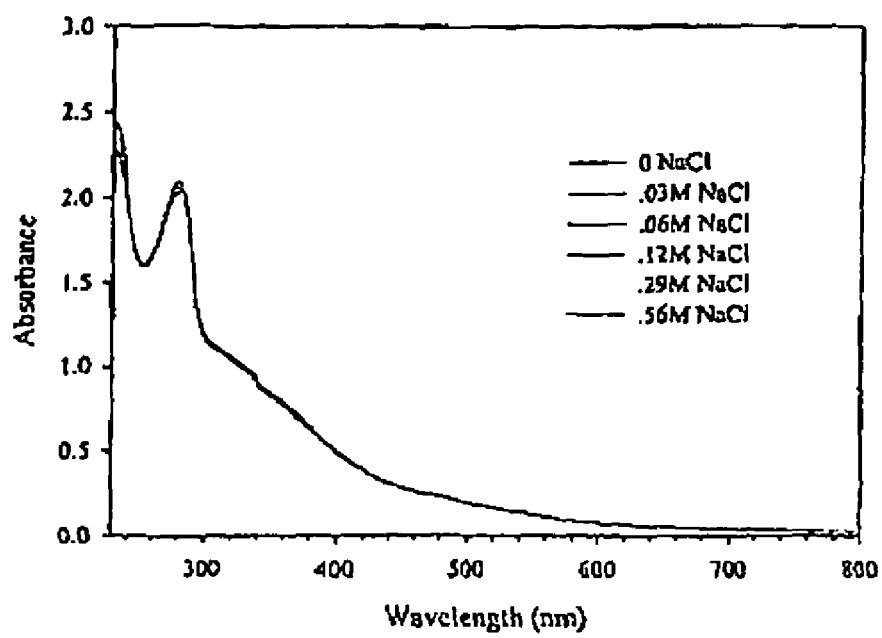
FIG. 15 shows the UV/vis absorption spectrum of mPEG-DOPA stabilized magnetite nanoparticles suspended in several aqueous NaCl solutions at the concentrations as shown and plotted therein. Addition of NaCl did not induce nanoparticle precipitation.

Suspensions of mPEG-DOPA stabilized nanoparticles were also found to be stable under physiologic concentrations of salt. To determine whether mPEG-DOPA could inhibit salt-induced nanoparticle aggregation, 0.3 mg of mPEG-DOPA treated magnetite was placed in a quartz cuvette and combined with 0.7 ml of water (18 MΩ-cm filtered using a 0.25μ filter). Aliquots of saturated NaCl solution (5 μl, 10 μl, 20 μl, 50 μl, 100 μl) were sequentially added to the cuvette and allowed to stand for ten minutes before UV-VIS spectra were taken (FIG. 15). The absorbance spectra of mPEG-DOPA stabilized nanoparticles suspended in solutions containing increasing NaCl concentration were nearly identical, demonstrating that mPEG-DOPA is effective at stabilizing the nanoparticles and preventing aggregation. The peak centered at 280 nm is indicative of the catechol side chain of DOPA.

Example 14e

The procedures and techniques illustrated in examples 14a-14d can be extended to various other metal oxide or ceramic nanoparticles, as would be understood by those skilled in the art made aware of this invention. Likewise, such applications of the present invention can further include use of a wide range of polymer-DHPD conjugates analogous to and consistent with those compositions and variations thereof described in examples 10b and 11b. As illustrated below in the preparation of semiconductor compositions, metal oxide or ceramic nanoparticles can be stabilized in situ upon formation in the presence of a polymer-DHPD conjugate of this invention.

Example 15a

Figure 16:
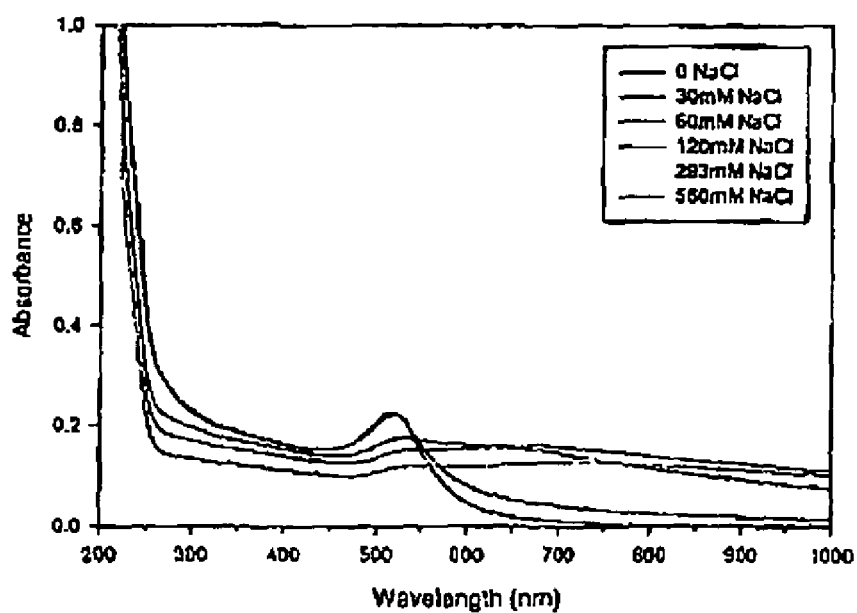
FIG. 16 shows addition of salt to untreated Au nanoparticles induces aggregation. Shown are UV/vis scans of 10 nm untreated Au nanoparticles suspended in aqueous NaCl solutions (concentrations as shown and plotted therein). The attenuation and shift of the 520 nm absorption band with increasing NaCl concentration reflects aggregation of the nanoparticles.
Figure 17:
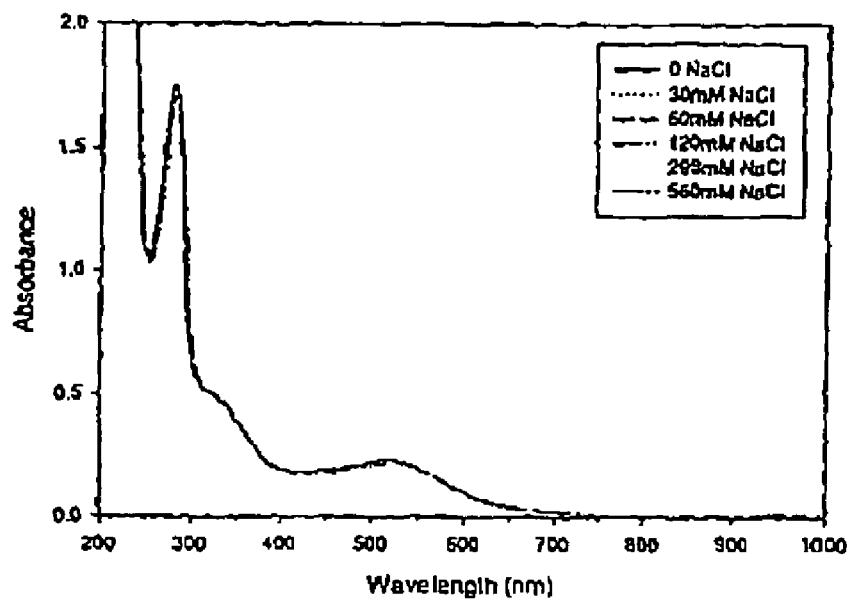
FIG. 17 illustrates addition of salt to mPEG-DOPA stabilized Au nanoparticles does not induce aggregation. Shown are UV/vis scans of 10 nm mPEG-DOPA stabilized Au nanoparticles suspended in aqueous NaCl solutions (concentrations as shown and plotted therein). The lack of attenuation and shift of the 520 nm absorption band with increasing NaCl concentration reflects effective stabilization of the nanoparticles.

Demonstrating stabilization of metal nanoparticles, commercial gold colloid suspension (Sigma, particle size 5 or 10 nm) was placed inside dialysis tubing ($M_w$ cutoff of 8000 for 5 nm and 15000 for 10 nm) and dialyzed in ultrapure water for 2-3 days to remove the sodium azide present in the commercial preparation. The dialyzed suspensions were then placed into small glass vials and mPEG-DOPA added (10 mg/ml). The samples were allowed to stand at room temperature for approximately 2 days, after which the samples were again dialyzed to remove excess mPEG-DOPA. Untreated 10 nm Au nanoparticles were unstable in the presence of NaCl and aggregated (FIG. 16), whereas the treated Au nanoparticles remained stably suspended in the presence of aqueous NaCl (FIG. 17).

Example 15b

Various other metal nanoparticles, including but not limited to, silver, platinum and the like can be stabilized as described in the preceding example. While stabilization was demonstrated using a representative conjugate composition of this invention, various other compositions can be prepared analogous to and consistent with the alternate embodiments described in Examples 10b and 11b. Comparable results can be obtained by in situ formation of the stabilized nanoparticles synthesized from the corresponding metal precursor in the presence of a suitable, adhesive conjugate polymer of this invention.

Example 16a

Figure 18:
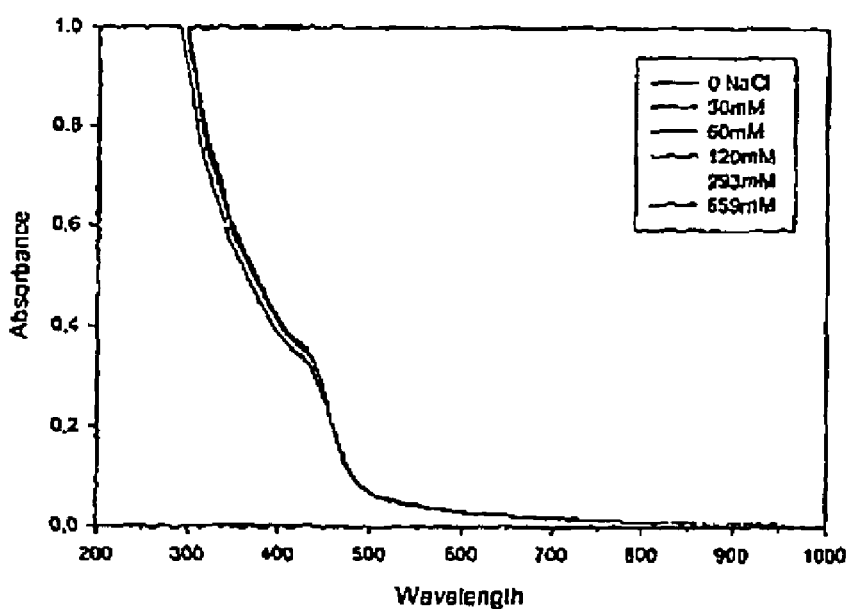
FIG. 18 plots the UV/vis absorption spectrum of mPEG-DOPA stabilized CdS nanoparticles suspended in aqueous NaCl solutions (concentrations as shown and plotted therein.

The data of this example demonstrates stabilization of semiconductor nanoparticles. CdS nanoparticles (quantum dots) were prepared by a standard method based on the slow mixing of dilute $Cd(NO_3)_2$ and $Na_2S$ solutions. Fresh stock solutions (2 mM) of $Cd(NO_3)_2$ and $Na_2S$ were prepared in nanopure water. The $Na_2S$ solution was injected slowly into 50 ml of $Cd(NO_3)_2$ solution using a gastight syringe at a rate of 20 μl $s^{-1}$. The solution turned yellow with the addition of $Na_2S$, and after 2 mL of $Na_2S$ was injected, a yellow precipitate appeared due to the aggregation of CdS nanoparticles. The CdS precipitate was isolated and dried for further use. Using the method described above for magnetite, the dry CdS powder was dispersed in a mPEG-DOPA solution by sonication to yield a clear yellow solution. The yellow aqueous suspension was stored in the dark for several months at room temperature without visible formation of precipitate. Control experiments performed in the absence of polymer and in the presence of mPEG-OH or mPEG-$NH_2$ yielded yellow precipitate and a clear, colorless supernatant. mPEG-DOPA stabilized CdS nanoparticles remained stably suspended in the presence of aqueous NaCl (FIG. 18).

Example 16b

The results of this example illustrate the in situ formation of stabilized semiconductor nanoparticles. CdS nanoparticles (quantum dots) were formed in the presence of mPEG-DOPA by slowly mixing dilute methanolic solutions of $Cd(NO_3)_2$ and $Na_2S$. Freshly prepared stock solutions (2 mM) of $Cd(NO_3)_2$ and $Na_2S$ were prepared in methanol. 25 mg of mPEG-DOPA (PEG molecular weight=2000) was dissolved in 5 ml of 2 mM $Cd(NO_3)_2$ in methanol, then 5 ml of a 2 mM solution of $Na_2S$ was added slowly with a syringe at a rate of 20 μl $s^{-1}$. The solution gradually turned yellow during the addition. No yellow precipitates were observed, and dynamic light scattering revealed particles with an average diameter of 2.5 nm. Control experiments performed in the absence of polymer or in the presence of mPEG-OH yielded yellow precipitate and a clear, colorless supernatant. Various other inorganic particulate substrates can be prepared, as would be understood by those skilled in the art, depending upon material choice and corresponding ionic substitution or exchange reaction, as carried out in the presence of an adhesive composition of the sort described herein.

Example 16c

The polymeric conjugate compositions of this invention can also be used to stabilize a variety of other semiconductor materials. For instance, core-shell nanoparticles can be surface stabilized in accordance herewith.

Example 17

The optimization experiments of Examples 17-20 were performed with mPEG-DOPA-5K. Several parameters were examined to optimize the adsorption of mPEG-DOPA onto gold from solution, including type and pH of solvent, time of adsorption, and mPEG-DOPA solution concentration. Cell attachment and spreading did not vary widely with adsorption solvent used. The number of cells on the substrates and their total projected area was not significantly different between DCM and three different aqueous solutions. The substrates adsorbed in neutral, basic, and organic mPEG-DOPA solutions all possessed significantly enhanced anti-fouling properties when compared to the unmodified substrate ($p<0.01$). Although no differences were observed in cell attachment and spreading between the solutions, the contact angle data would support the use of an organic solvent in an optimal modification protocol as a means to reduce catechol oxidation. Additionally, only the surface modified in DCM demonstrated significantly fewer cells on the surface and lower total projected cellular area.

Example 18

Cell attachment and spreading showed a strong dependence on solution concentration of mPEG-DOPA (FIG. 12). Above 25 mg/ml mPEG-DOPA, significantly fewer cells attached and spread on the modified substrate than on the pristine gold surface ($p<0.001$) and the surface modified in a 10 mg/ml solution ($p<0.05$). Below 10 mg/ml, there were no differences in cell attachment and spreading compared to the unmodified substrate. There were no differences in cell attachment and spreading observed between surfaces modified in mPEG-DOPA solutions ranging from 25-75 mg/ml when compared to each other.

Example 19

Fewer fibroblasts were observed to attach and spread with increasing duration of mPEG-DOPA adsorption, as well. Although cell attachment and spreading appeared to decrease with as little as 5 minutes of substrate modification, an adsorption time of 24 hours resulted in significantly fewer cells attaching and spreading on the PEGylated substrate than on the unmodified substrate ($p<0.001$) and substrates treated for shorter periods ($p<0.05$).

Example 20

Figure 14A:
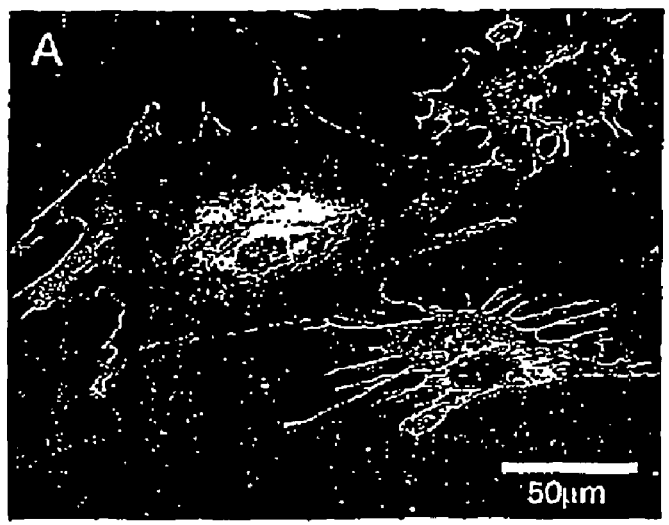
FIGS. 14 A-C are a series of SEM micrographs indicating the morphology of NIH 3T3 fibroblasts on (A) unmodified Au, (B) Au treated with mPEG-OH, and (C) mPEG-DOPA-modified Au. All treatments were at 50 mg/ml in DCM for 24 h.
Figure 14B:
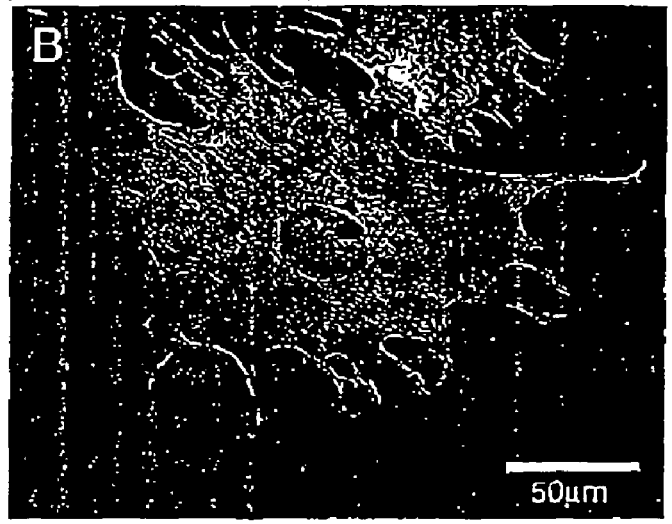
Figure 14C:
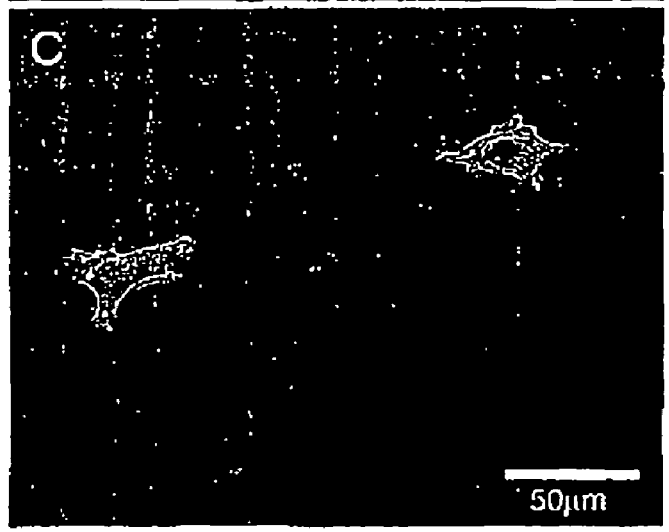

The morphology of fibroblasts cultured on both unmodified and PEG-modified surfaces was examined via electron microscopy (Hitachi 3500 SEM). Fibroblasts on unmodified Au and mPEG-OH-modified Au were generally flat and well spread, while those cultured on mPEG-DOPA modified Au were far less spread (FIGS. 14A-C). It should also be noted that on the mPEG-DOPA surface, a lower number of cellular processes were observed than in the others, structures which contribute to cell adhesion via integrins and focal adhesions. FIG. 13 illustrates the differences in attachment and spreading of fibroblasts on bare Au, mPEG-OH-treated Au, and Au modified with mPEG-DOPA 5K, mPEG-MAPd 2K, or mPEG-MAPd 5K under optimal conditions (50 mg/ml for 24 hours). The surfaces modified with DOPA-containing conjugates have significantly less cellular adhesion and spreading than either of the other two surfaces. The mPEG-MAP 5K modification, though, accounted for a 97% reduction in total projected cellular area and a 91% reduction in density of cells on the surface, a far greater reduction than that achieved by mPEG-DOPA 2K.

The differences in cellular adhesion and spreading between surfaces modified with DOPA- and MAPd-conjugated PEG in FIG. 13 can likely be attributed to the physical characteristics of the associated PEG adlayer. Analysis of the SPR results indicates that MAPd-PEGs form thicker, more robust adlayers with a higher concentration of PEG per unit area than do the DOPA-anchored PEGs of equivalent molecular weight. The thicker adlayers resulting from MAPd-mediated PEGylation are more successful in inhibiting protein adsorption and, in turn, cell adhesion.

Example 21

Synthesis of Boc-DOPA (TBDMS)$_2$-OSu

N-hydroxysuccinimide (NHS) (0.110 g, 0.95 mmol) was added to a solution of Boc-DOPA(TBDMS)$_2$ (0.500 g, 0.95 mmol) in dry dichloromethane (DCM) (8.0 mL). The solution was stirred on an ice bath, and 1,3-dicyclohexylcarbodiimide (DCC) (0.197 g, 0.95 mmol) was added under nitrogen atmosphere. The reaction was stirred for 20 minutes at 0° C. and then warmed to room temperature and stirred for an additional 4 hours. The reaction mixture was filtered to remove the urea byproduct and subsequently evaporated to ⅕ of its original volume. The solution was cooled to 4° C., allowed to sit for 2 hours to precipitate the remaining urea byproduct, filtered and evaporated to give Boc-DOPA(TBDMS)$_2$-OSu as a white foam (0.567 g, 96% yield).

Example 22

Synthesis of Boc-DOPA$_2$(TBDMS)$_4$

Boc-DOPA(TBDMS)$_2$-OSu (0.567 g, 0.91 mmol) was dissolved in dry dimethylformamide (DMF) (2.5 mL), and DOPA(TBDMS)$_2$ (0.405 g, 0.95 mmol) was added at once under a nitrogen atmosphere. The mixture was stirred on an ice bath, and diisopropylethylamine (DIEA) (158 μL, 0.91 mmol) was added dropwise via a syringe. After 20 minutes, the reaction was warmed to room temperature, stirred for an additional 17 hours, filtered (if necessary), diluted with ethyl acetate (EtOAc) (40 mL), transferred to a separatory funnel, and washed with 5% aqueous HCl. The aqueous layer was extracted back with EtOAc. The organic layers were combined and washed with 5% aqueous HCl (3×), H$_2$O (1×), dried with MgSO$_4$, and evaporated to afford Boc-DOPA$_2$(TBDMS)$_4$ as a white foam (0.83 g, 98% yield).

Example 23

Synthesis of Boc-DOPA$_2$(TBDMS)$_4$-OSu

The procedure of Example 21 was repeated using Boc-DOPA$_2$(TBDMS)$_4$ to obtain Boc-DOPA$_2$(TBDMS)$_4$-OSu.

Example 24

Synthesis of Boc-DOPA$_3$(TBDMS)$_6$

The procedure of Example 22 was repeated using Boc-DOPA$_2$(TBDMS)$_4$-OSu to obtain Boc-DOPA$_3$(TBDMS)$_6$.

Example 25

Synthesis of DOPA$_2$

Boc-DOPA$_2$(TBDMS)$_4$ (0.5 g, 0.54 mmol) was dissolved in saturated HCl/EtOAc (3 mL), and the solution was stirred under nitrogen. After 5 hours, additional HCl gas was gently bubbled through the solution for 25 minutes. The reaction was allowed to sit overnight, and subsequently concentrated to ½ of original volume. The resulting precipitate was collected by centrifugation, washed with cold EtOAc (3×), and dried to yield $DOPA_2$ as a white powder (0.15 g, 74% yield). The product was further purified by preparative RP-HPLC, and characterized by ESI-MS.

Example 26

Synthesis of $DOPA_3$

Boc-$DOPA_3$(TBDMS)$_6$ (1.06 g, 0.79 mmol) was dissolved in saturated HCl/EtOAc (3 mL), and the solution was stirred under nitrogen. After 12 hours, additional HCl gas was gently bubbled through the solution for 30 minutes, and the reaction was allowed to continue for 40 hours. More HCl gas was bubbled through the solution for another 30 minutes, and the stirring was stopped. The resulting precipitate was collected by centrifugation, washed with cold EtOAc (3×), and dried to give $DOPA_3$ as a white powder (0.424 g, 96% yield). The product was further purified by preparative RP-HPLC, and characterized by ESI-MS.

Example 27

Synthesis of mPEG-$DOPA_{1-3}$

A solution of 0.1 M borate buffer (50 mL, pH 8.5) was degassed with argon for 20 minutes, and L-DOPA (0.197 g, 1.0 mmol) was added. After the solution was stirred for 15 minutes, methoxy-terminated PEG-SPA (mPEG-SPA) 5K (0.5 g, 0.1 mmol) was added in portions, and the reaction was allowed to stir for 3 hours. The resulting clear solution was then acidified to pH of 1-2 with aqueous HCl, and extracted with DCM (3×). The combined organic layers were washed with 0.1 M HCl, dried over $MgSO_4$ and concentrated. The remaining residue was dissolved in DCM and precipitated with ethyl ether three times to afford mPEG-DOPA as a white powder (0.420 g, 84% yield). The product was characterized by MALDI-MS and $^1$H NMR spectroscopy.

Example 28

Surface Modification

Solid metal substrates (Al, 316L stainless steel and NiTi) were ground and polished, ultimately with 0.04 m colloidal silica (Syton, DuPont). Si wafers were evaporated with either 20 nm $TiO_2$ or 10 nm $TiO_2$/40 nm Au using an Edwards FL400 electron beam evaporator at <$10^{-6}$ Torr and were subsequently diced in 8 mm×8 mm pieces. All substrates were cleaned ultrasonically for 20 minutes in each of the following: 5% Contrad70 (Fisher Scientific), ultrapure $H_2O$, acetone, and petroleum ether. Subsequently, surfaces were further cleaned by exposure to $O_2$ plasma (Harrick Scientific) at 150 mTorr and 100 W for 5 minutes. To prevent the formation of a gold oxide ($Au_2O_3$) layer, some Au substrates were not exposed to $O_2$ plasma. To generate a biopolymer analog surface, glass coverslips (Fisher Scientific) were cleaned as described above and immersed in a 0.01% solution of poly-L-lysine (Sigma) for 5 minutes, rinsed with ultrapure $H_2O$, and dried under nitrogen.

In order to explore a variety of modification conditions with a minimum number of samples, a nine element Robust Design approach was employed. Substrates were modified under cloud point conditions by immersion in mPEG-$DOPA_{1-3}$ solutions in 0.6 M $K_2SO_4$ buffered with 0.1 M MOPS at 50° C. Buffer pH, modification time, and mPEG-DOPA concentration were modified as shown in Table 7. Modified substrates were subsequently rinsed with ultrapure $H_2O$ and dried under a stream of nitrogen.

TABLE 7

| Experiment | Anchoring Group | Buffer pH | Adsorption Time | Polymer Concentration |
| --- | --- | --- | --- | --- |
| 1 | -DOPA | 3.0 | 1 h | 0.5 mg/mL |
| 2 | -DOPA | 6.0 | 4 h | 1.0 mg/mL |
| 3 | -DOPA | 9.0 | 24 h | 3.0 mg/mL |
| 4 | -$DOPA_2$ | 3.0 | 4 h | 3.0 mg/mL |
| 5 | -$DOPA_2$ | 6.0 | 24 h | 0.5 mg/mL |
| 6 | -$DOPA_2$ | 9.0 | 1 h | 1.0 mg/mL |
| 7 | -$DOPA_3$ | 3.0 | 24 h | 1.0 mg/mL |
| 8 | -$DOPA_3$ | 6.0 | 1 h | 3.0 mg/mL |
| 9 | -$DOPA_3$ | 9.0 | 4 h | 0.5 mg/mL |

Example 28a $TiO_2$ Substrates $TiO_2$ substrates were modified under cloud point conditions by immersion in mPEG-$DOPA_{1-3}$ solutions in 0.6 M $K_2SO_4$ buffered with 0.1 M N-morpholinopropanesulfonic acid (MOPS) at 50° C. for 24 hours. Modified substrates were rinsed with ultrapure $H_2O$ and dried under a stream of nitrogen.

Example 28b

316L Stainless Steel (Goodfellow, Devon Pa.) was modified under cloud point conditions by immersion in mPEG-$DOPA_{1-3}$ solutions in 0.6 M $K_2SO_4$ buffered with 0.1 M N-morpholinopropanesulfonic acid (MOPS) at 50° C. for 24 hours. Modified substrates were rinsed with ultrapure $H_2O$ and dried under a stream of nitrogen.

Example 28c $Al_2O_3$ (Goodfellow, Devon Pa.) was modified under cloud point conditions by immersion in mPEG-$DOPA_{1-3}$ solutions in 0.6 M $K_2SO_4$ buffered with 0.1 M N-morpholinopropanesulfonic acid (MOPS) at 50° C. for 24 hours. Modified substrates were rinsed with ultrapure $H_2O$ and dried under a stream of nitrogen.

Example 28d $SiO_2$ (1500 Å thermal oxide, University Wafer, South Boston, Mass.) was modified under cloud point conditions by immersion in mPEG-$DOPA_{1-3}$ solutions in 0.6 M $K_2SO_4$ buffered with 0.1 M N-morpholinopropanesulfonic acid (MOPS) at 50° C. for 24 hours. Modified substrates were rinsed with ultrapure $H_2O$ and dried under a stream of nitrogen.

Example 28e

NiTi alloy (10 mm×10 mm×1 mm) was obtained from Nitinol Devices & Components (Fremont, Calif.) and modified under cloud point conditions by immersion in mPEG-$DOPA_{1-3}$ solutions in 0.6 M $K_2SO_4$ buffered with 0.1 M N-morpholinopropanesulfonic acid (MOPS) at 50° C. for 24 hours. Modified substrates were rinsed with ultrapure $H_2O$ and dried under a stream of nitrogen.

Example 28f

Au (electron beam evaporated onto Si Wafer from University Wafer) was modified under cloud point conditions by immersion in mPEG-DOPA$_{1-3}$ solutions in 0.6 M K$_2$SO$_4$ buffered with 0.1 M N-morpholinopropanesulfonic acid (MOPS) at 50° C. for 24 hours. Modified substrates were rinsed with ultrapure H$_2$O and dried under a stream of nitrogen.

Example 28g

Au$_2$O$_3$ (Au samples as described in Example 28f were exposed to an oxygen plasma to form Au2O3) was modified under cloud point conditions by immersion in mPEG-DOPA$_{1-3}$ solutions in 0.6 M K$_2$SO$_4$ buffered with 0.1 M N-morpholinopropanesulfonic acid (MOPS) at 50° C. for 24 hours. Modified substrates were rinsed with ultrapure H$_2$O and dried under a stream of nitrogen.

Example 28h

GaAs (University Wafer, South Boston, Mass.) was modified under cloud point conditions by immersion in mPEG-DOPA$_{1-3}$ solutions in 0.6 M K$_2$SO$_4$ buffered with 0.1 M N-morpholinopropanesulfonic acid (MOPS) at 50° C. for 24 hours. Modified substrates were rinsed with ultrapure H$_2$O and dried under a stream of nitrogen.

Example 28i p-L-Lys surfaces were made by immersing glass coverslips (Fisher Scientific) in a 0.01% solution of poly-L-lysine (p-L-Lys, Sigma) for 5 minutes, rinsed with ultrapure H$_2$O, and dried under N$_2$. They were then modified under cloud point conditions by immersion in mPEG-DOPA$_{1-3}$ solutions in 0.6 M K$_2$SO$_4$ buffered with 0.1 M N-morpholinopropanesulfonic acid (MOPS) at 50° C. for 24 hours. Modified substrates were rinsed with ultrapure H$_2$O and dried under a stream of nitrogen.

Example 29

Cell Adhesion

3T3 Swiss albino fibroblasts (ATCC, Manassas, Va.) of passage 12-16 were cultured normally at 37° C. and 5% CO$_2$ in Dulbecco's modified Eagle's medium (DMEM) (Cellgro, Herndon, Va.) supplemented with 10% fetal bovine serum (FBS) (Cellgro, Herndon, Va.), 100 g/mL penicillin, and 100 U/mL steptomycin. Prior to cell adhesion assays, fibroblasts were harvested using 0.25% trypsin-EDTA, resuspended in growth medium, and counted with a hermacytometer.

General Procedure for Four-Hour Assay

Test substrates were prepared in 12-well tissue culture polystyrene plates with 1.0 mL DMEM with FBS for 30 minutes at 37° C. and 5% CO$_2$. Cells were seeded onto the substrates at a density of 2.9×10$^3$ cells/cm$^2$ and maintained in DMEM with 10% FBS at 37° C. and 5% CO$_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29a

TiO$_2$ Substrate (4-Hour Assay)

Test substrates were prepared in 12-well tissue culture polystyrene plates with 1.0 mL DMEM with FBS for 30 minutes at 37° C. and 5% CO$_2$. Cells were seeded onto the substrates at a density of 2.9×10$^3$ cells/cm$^2$ and maintained in DMEM with 10% FBS at 37° C. and 5% CO$_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29b

TiO$_2$ Substrate (Long-Term Studies)

For long-term studies on TiO$_2$, substrates were reseeded twice per week at the same density as for the 4-hour assay. At periodic intervals, non-adherent cells were removed by aspirating the medium in each well.

Example 29c

316L Stainless Steel Substrate (4-Hour Assay)

Test substrates were prepared in 12-well tissue culture polystyrene plates with 1.0 mL DMEM with FBS for 30 minutes at 37° C. and 5% CO$_2$. Cells were seeded onto the substrates at a density of 2.9×10$^3$ cells/cm$^2$ and maintained in DMEM with 10% FBS at 37° C. and 5% CO$_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29d

Al$_2$O$_3$ Substrate (4-Hour Assay)

Test substrates were prepared in 12-well tissue culture polystyrene plates with 1.0 mL DMEM with FBS for 30 minutes at 37° C. and 5% CO$_2$. Cells were seeded onto the substrates at a density of 2.9×10$^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29e $SiO_2$ Substrate (4-Hour Assay)

Test substrates were prepared in 12-well tissue culture polystyrene plates with 1.0 mL DMEM with FBS for 30 minutes at 37° C. and 5% $CO_2$. Cells were seeded onto the substrates at a density of $2.9 \times 10^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29f

NiTi Substrate (4-Hour Assay)

Test substrates were prepared in 12-well tissue culture polystyrene plates with 1.0 mL DMEM with FBS for 30 minutes at 37° C. and 5% $CO_2$. Cells were seeded onto the substrates at a density of $2.9 \times 10^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29g

Au Substrate (4-Hour Assay)

Test substrates were prepared in 12-well tissue culture polystyrene plates with 1.0 mL DMEM with FBS for 30 minutes at 37° C. and 5% $CO_2$. Cells were seeded onto the substrates at a density of $2.9 \times 10^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29h $Au_2O_3$ Substrate (4-Hour Assay)

Test substrates were prepared in 12-well tissue culture polystyrene plates with 1.0 mL DMEM with FBS for 30 minutes at 37° C. and 5% $CO_2$. Cells were seeded onto the substrates at a density of $2.9 \times 10^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 29i

GaAs Substrate (4-Hour Assay)

Test substrates were prepared in 12-well tissue culture polystyrene plates with 1.0 mL DMEM with FBS for 30 minutes at 37° C. and 5% $CO_2$. Cells were seeded onto the substrates at a density of $2.9 \times 10^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation, Downington, Pa.). The mean and standard deviation of the measurements are reported.

Example 29j p-L-Lys Substrate (4-Hour Assay)

Test substrates were prepared in 12-well tissue culture polystyrene plates with 1.0 mL DMEM with FBS for 30 minutes at 37° C. and 5% $CO_2$. Cells were seeded onto the substrates at a density of $2.9 \times 10^3$ cells/cm$^2$ and maintained in DMEM with 10% FBS at 37° C. and 5% $CO_2$ for 4 hours. For the 4-hour cell adhesion assay, adherent cells were fixed in 3.7% paraformaldehyde for 5 minutes and subsequently stained with 5 µM 1,1'-dioctadecyl-3,3,3',3'-tetramethylindocarbocyanine perchlorate (DiI) (Molecular Probes, Eugene, Oreg.) in DMSO for 45 minutes at 37° C.

Quantitative cell attachment data was obtained by acquiring 9-16 images (depending on substrate size) from random locations on each substrate using a Leica epifluorescent microscope equipped with a SPOT RT digital camera (Diagnostic Instruments, Sterling Heights, Mich.). The resulting images were quantified in terms of total projected cellular area using thresholding in MetaMorph. (Universal Imaging Corporation™, a subsidiary of Molecular Devices Corporation, Downington, Pa.). The mean and standard deviation of the measurements are reported.

Example 30

Twenty-four-hour Modification of Substrates and Four-hour Assay

Figure 24:
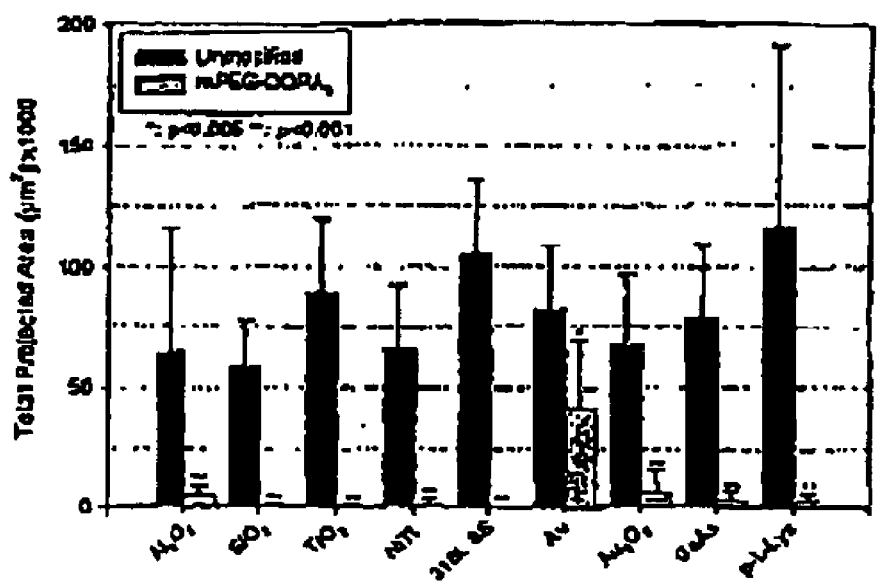
FIG. 24 plots the 4-hour cell attachment to a variety of surfaces modified by mPEG-DOPA$_{1-3}$ using a 24-hour modification at 50° C. at the indicated pHs.

Each surface was modified for 24 hours in a solution of 1.0 mg/mL mPEG-DOPA$_3$ (or mPEG-OH as a control) at 50° C. at the pH values shown in FIG. 24. A four-hour cell adhesion and spreading assay was conducted as described above in Example 9. Results are shown in FIG. 24. Cell adhesion resistance was conferred to all substrates treated with mPEG-DOPA$_3$. Cell adhesion and spreading on substrates treated with mPEG-OH did not differ from the unmodified surfaces (data not shown).

Example 31

Surfaces and Surface Preparation

Silicon wafers (WaferNet GmbH, Germany) were coated with $TiO_2$ (20 nm) by physical vapor deposition using reactive magnetron sputtering (PSI, Villigen, Switzerland). Metal oxide coated wafers were subsequently diced into 1 cm×1 cm pieces for ex-situ ellipsometry measurements. Optical waveguide chips for OWLS measurements were purchased from Microvacuum Ltd. (Budapest, Hungary) and consisted of a AF45 glass substrate (8×12×0.5 mm) and a 200 nm-thick $Si_{0.25}Ti_{0.75}O_2$ waveguiding surface layer. An 8 nm $TiO_2$ layer was deposited on top of the waveguiding layer under the same conditions described above for the silicon wafers. Prior to polymer modification, $TiO_2$-coated silicon wafers and waveguide chips were sonicated in 2-propanol for 10 minutes, rinsed with ultrapure water, and dried under a stream of nitrogen, followed by a 3 minute exposure to $O_2$ plasma (Harrick Scientific, Ossining, USA) to remove all organic components from the surface. After OWLS measurements, waveguides were regenerated for reuse by sonication (10 minute) in cleaning solution (300 mM HCl, 1% detergent; Roche Diagnostics, Switzerland) and subsequent rinsing with ultrapure water to remove adsorbates.

Surface Modification

Surfaces were modified by mPEG-DOPA$_{1-3}$, produced according to Example 27, for 24 hours at a polymer concentration of 1.0 mg/ml using cloud point buffer (CP buffer: 0.6 M $K_2SO_4$ buffered to pH=6.0 with 0.1 M MOPS) at temperatures ranging from 25° C. to 50° C. After modification, substrates were rinsed with water, dried in a stream of $N_2$, and immediately analyzed as described below.

X-ray Photoelectron Spectroscopy (XPS) Measurements

Survey and high resolution spectra were collected on a SAGE 100 (SPECS, Berlin, Germany) using a standard (non-monochromatized) $AlK_\alpha$ X-ray source operating at 325 W (13 kV, 25 mA) and a take-off angle of 0°, defined as the angle between the photoelectron detector and the surface normal. Pass energies of 50 eV and 14 eV were used for survey and high-resolution spectra, respectively. The pressure of the analysis chamber remained below $2 \times 10^{-8}$ Pa during data acquisition. All XPS spectra were referenced to the aliphatic hydrocarbon component of the C1s signal at 284.7 eV. Curve fitting was performed with CasaXPS software using Shirley background subtraction and the sum of a 90% Gaussian and 10% Lorentzian function. Measured intensities (peak areas) were converted to normalized intensities by atomic sensitivity factors, from which atomic compositions of surfaces were calculated. Average values obtained from three substrate replicates is reported in Tables 8-9. Standard deviations were typically <10% of the mean and are omitted for clarity.

TABLE 8

Quantitative Analysis of XPS Data for mPEG-DOPA Modified $TiO_2$ Surfaces

| | atomic concentration (atom %) | | | | | | |
|---|---|---|---|---|---|---|---|
| | | O | | | C | | |
| surface | Ti | $O1s_A$ $TiO_2$ | $O1s_B$ TiOH | $O1s_C$ C—O, $H_2O$ | $C1s_A$ C—C, C—H | $C1s_B$ C—O | $C1s_C$ NHC(=O) |
| Clean $TiO_2$ | 24.3 | 50.9 | 14.1 | 4.1 | 4.5 | 1.2 | 0.9 |
| mPEG-DOPA$_1$ | 17.9 | 36.8 | 5.2 | 13.1 | 2.8 | 23.1 | 1.2 |
| mPEG-DOPA$_2$ | 11.1 | 22.5 | 3.2 | 20.2 | 3.7 | 37.3 | 2.1 |
| mPEG-DOPA$_3$ | 7.4 | 15.9 | 0.5 | 25.3 | 4.0 | 43.7 | 3.2 |

TABLE 9

Atomic Ratios Calculated from XPS Data for mPEG-DOPA Modified $TiO_2$ Surfaces

| surface | C/Ti | $O_A$/Ti | $O_B/O_A$ | $C_B/C_A$ | $C_C/C_B$ | $C_C/C_A$ |
|---|---|---|---|---|---|---|
| clean $TiO_2$ | 0.27 | 2.10 | 0.28 | 0.33 | 0.42 | 0.20 |
| mPEG-DOPA | 1.52 | 2.06 | 0.14 | 8.42 | 0.052 | 0.42 |
| mPEG-DOPA$_2$ | 3.89 | 2.03 | 0.14 | 10.07 | 0.055 | 0.56 |
| mPEG-DOPA$_3$ | 6.87 | 2.14 | 0.03 | 11.00 | 0.074 | 0.80 | atomic ratio[a]

[a]Contributions A, B, and C are defined in Table 7.

Spectroscopic Ellipsometry

For ELM measurements, $TiO_2$-sputtered Si substrates were modified ex-situ as described above, with the temperature of the modification solution varied from 25° C. to 50° C. After modification, substrates were rinsed with $H_2O$, incubated at room temperature in 10 mM HEPES buffer (pH=7.4) for 48 hours, rinsed again with $H_2O$ and dried with $N_2$. To examine protein resistance, modified and unmodified substrates were exposed to pure human serum for 15 minutes, rinsed with water, and dried in a stream of $N_2$. ELM measurements were made on a M-2000D spectroscopic ellipsometer (J. A. Woollam Co., Inc., Lincoln, USA) at 65°, 70°, and 75° using wavelengths from 193-1000 nm prior to and immediately after modification, after HEPES incubation, and after serum exposure. ELM spectra were fit with multilayer models in the WVASE32 analysis software using the optical properties of a generalized Cauchy polymer layer ($A_n$=1.45, $B_n$=0.01, $C_n$=0), to obtain the "dry" thicknesses of adsorbed PEG and serum adlayers. (The "dry" or dehydrated thickness is that measured under ambient conditions after drying with $N_2$.) The average thickness measured from three replicates is reported in Tables 10-11.

TABLE 10

Effect of Adsorption Temperature on Thickness of PEG Adlayers on $TiO_2$[a]

| Adsorption Temperature (° C.) | Thickness (Å) |
|---|---|
| 25 | 10.6 ± 1.8 |
| 28 | 13.9 ± 0.3 |
| 31 | 16.4 ± 1.1 |
| 34 | 19.4 ± 1.9 |
| 37 | 19.6 ± 3.5 |
| 40 | 22.5 ± 2.0 |
| 45 | 24.4 ± 2.0 |
| 50 | 33.8 ± 4.6 |

[a]$TiO_2$ surfaces were exposed to mPEG-DOPA$_3$ (1 mg/ml) for 2 h after which each surface was rinsed for 48 h in HEPES.

TABLE 11

Apparent Thickness (Å) of Organic Adlayers on $TiO_2$ as Measured, by Spectroscopic Ellipsometry

| Treatment[a] | mPEG-DOPA$_3$ adsorption time (min) | | | | | |
|---|---|---|---|---|---|---|
| | 0 | 1 | 30 | 60 | 240 | 1080 |
| Before serum exposure | — | 5.1 | 24.2 | 27.6 | 31.8 | 35.0 |
| After serum exposure | 60.2 | 23.4 | 24.7 | <28.1[b] | <32.3[b] | <35.5[b] |

[a]$TiO_2$ surfaces were exposed to mPEG-DOPA$_3$ (1 mg/ml) for 0–1080 min, rinsed with water, incubated for 48 h in HEPES and then exposed to serum for 15 min.
[b]The net increase in adlayer thickness after serum exposure was less than 0.5 Å, the approximate resolution of the ELM technique.

Optical Waveguide Lightmode Spectroscopy (OWLS)

$TiO_2$-coated waveguides were cleaned in 2-propanol and $O_2$ plasma as described above. Clean waveguides were mounted in the measurement head of an OWLS110 (Microvacuum Ltd.) and stabilized for at least 48 hours at room temperature in cloud point buffer (CP buffer: 0.6 M $K_2SO_4$ buffered to pH=6.0 with 0.1 M MOPS). The stabilization period allowed for the exchange of ions at the $TiO_2$ surface to come to equilibrium and obtain a stable baseline. To monitor polymer adsorption, mPEG-DOPA in CP buffer was injected in stop-flow mode, followed by CP buffer to remove unbound PEG, after which the signal was allowed to stabilize. The incoupling angles, $\alpha_{TM}$ and $\alpha_{TE}$, were recorded and converted to refractive indices ($N_{TM}$, $N_{TE}$) by the manufacturer-supplied software. Real-time changes in the effective refractive index of the sensor were converted to adsorbed mass using de Feijter's formula. The refractive index increment, dn/dc, for each mPEG-DOPA polymer was calculated by linear interpolation between 0.13 cm$^3$/g for pure PEG and 0.18 cm$^3$/g for pure poly(amino acid). For protein adsorption experiments, the temperature of the measurement head was equilibrated at 37° C. until the signal stabilized, after which serum was injected for 15 minutes followed by injection of buffer. Substantial differences in adsorbed mass were not observed with increases in serum exposure time.

Example 32

Synthesis of N-methacryloyl 3,4-dihydroxyl-L-phenylalanine 1.15 g (5.69 mmol) of $Na_2B_4O_7$ was dissolved in 30 ml of water. The solution was degassed with Ar for 30 minutes, after which 0.592 g (3.0 mmol) of L-DOPA was added and stirred for 15 minutes. 0.317 g (3.0 mmol) of $Na_2CO_3$ was then added, the solution was cooled to 0° C., and 0.3 ml (3.0 mmol) of methacryloyl chloride was slowly added with stirring. The pH of the solution was maintained above 9 with $Na_2CO_3$ during the reaction. After stirring for 1 hour at room temperature, the solution was acidified to pH of 2 with concentrated HCl. The mixture was extracted with ethyl acetate three times. After washing with 0.1 N HCl and drying over anhydrous $MgSO_4$, the solvent was removed in vacuo to yield crude light brown solid. The product was further purified by elution from a silica gel column with dichloromethane (DCM) and methanol (95:5). After evaporating the solvent, a white, sticky solid was obtained with a product yield of 35%. $^1$HNMR (500 MHz, acetone-d$_6$): ÿ 7.1 d (1H, —NH—); 6.6-6.8 (3H, $C_6H_3(OH)_2$—); 5.68 s (1H, CHH=); 5.632 s (unknown peak); 5.33 s (1 H, CHH=); 4.67 m (1H, —CH—); 2.93-3.1 m (2H, $CH_2$—); 1.877 s (3 H, —$CH_3$).

Example 33

Synthesis of 3,4-bis(t-butyldimethylsilyloxy)-L-phenylalanine 3.60 g (24.0 mmol) of TBDMS-Cl was dissolved in 18 ml of anhydrous acetonitrile. 1.60 g (8.0 mmol) of L-DOPA was added to the solution, the suspension was stirred and cooled to 0° C., and 3.6 ml of DBU (24.0 mmol) was added. The reaction mixture was then stirred for 24 hours at room temperature. Addition of cold acetonitrile to the reaction solution resulted in a colorless precipitate. The precipitate was filtered and washed with cold acetonitrile several times followed by drying in vacuum. White powder was obtained with a yield of 78%. $^1$H NMR (500 MHz, methanol-d): ÿ 6.7-6.9 (e H, $C_6H_3$(O—Si—)$_2$—); 3.72 (m, 1 H, —CH—); 2.82-3.2 (m, 2 H, —$CH_2$—); 1.0 (d, 18 H, —C($CH_3$)); 0.2 (d, 12 H, Si—$CH_3$).

Example 34

Synthesis of 3,4-bis(t-butyldimethylsilyloxy)-N-t-butyloxycarbonyl-L-phenylalanine 1.60 g (3.77 mmol) of 3,4-bis(t-butyldimethylsilyloxy)-L-phenylalanine was added to 10 ml of water containing 0.34 g (4.05 mmol) of NaHCO$_3$. 0.96 g (4.30 mmol) of di-t-butyl dicarbonate in 10 ml of tetrahydrofuran was added and the reaction mixture was stirred for 24 hours at room temperature. After evaporation of tetrahydrofuran, 10 ml of water was added to the residue. The solution was acidified with dilute HCl to pH of 5 and extracted three times with ethyl acetate. After drying over anhydrous MgSO$_4$, the solvent was removed in vacuo. The crude product was purified by column chromatography (silica gel; eluent; 10% methanol in DCM). A white solid was obtained with a yield of 70% after evaporating the eluting solvent. $^1$H NMR (500 MHz, methanol-d); ÿ 6.68-6.81(3 H, C$_6$H$_3$(O—Si—)$_2$—); 4.28 (m, 1 H, —CH—); 2.78-3.08 (m, 2 H, —CH$_3$—); 1.4 (s, 9 H, —O—C(CH$_3$)$_3$); 1.0 (d, 18 H, —Si—C(CH$_3$)$_3$); 0.2 (d, 12 H, Si—(CH$_3$)$_2$).

Example 35

Synthesis of 3,4-Bis(t-butyldimethylsilyloxy)-N-t-butyloxycarbonyl-L-phenylalanine Pentafluorophenyl Ester 1 g (1.90 mmol) of 3,4-bis(t-butyldimethylsilyloxy)-N-t-butyloxycarbonyl-L-phenylalanine and 0.351 g (1.90 mmol) of pentafluorophernol were dissolved in a solvent mixture of 24 ml of dioxance and 1 ml of DMF, and 0.432 g (2.10 mmol) of DCC was added at 0° C. The solution was stirred for 1 hour at 0° C. and for 1 hour at room temperature, after which the solution was filtered to remove dicyclohexylurea and evaporated in vacuo. The product 4 was purified by column chromatography (silica gel; eluent; hexane/ethyl acetate=11.2). After removing the eluent, pure white, sticky solid was obtained with a yield of 55%. $^1$H NMR (500 MHz, CDCl$_3$); ÿ 6.65-6.81(3 H, C$_6$H$_3$(O—Si—)$_2$—); 4.85 (m, 1 H, —CH—); 3.05-3.2 (m, 2 H, —CH$_3$—); 1.41 (s, 9 H, —O—C(CH$_3$)$_3$); 1.0 (d, 18 H, —Si—C(CH$_3$)$_3$); 0.2 (d, 12 H, Si—(CH$_3$)$_2$).

Example 36

Synthesis of N-(13'-Amino-4',7',10'-trioxatridecanyl)-t-butyloxycarbonyl-3',4'-bis(t-butyldimethylsilyloxy)-L-phenylalanamide 0.869 g (1.26 mmol) of 3,4-Bis(t-butyldimethylsilyloxy)-N-t-butyloxycarbonyl-L-phenylalanine pentafluorophenyl ester in 10 ml of DCM was added dropwise to a mixture of 2.07 ml (9.44 mmol) of 4,7,10-trioxa-1,13-tridecanediamine and 1.32 ml (9.44 mmol) of Et$_3$N in 1 ml DMF over 30 minutes at 0° C. The solution was stirred at room temperature for another 2 hours, and then the solvent was removed under vacuum. The crude product was loaded onto silica gel and eluted with DCM, 5% methanol in DCM, 10% methanol in DCM, and 15% methanol in DCM. The solvent was removed under vacuum to yield 5 as a white solid. The yield was 63%. $^1$H NMR (500 MHz, acetone-d$_6$); ÿ 7.38 (m, 1 H, —CONH—); 6.60-6.80 (3 H, C$_6$H$_3$(O—Si—)$_2$—); 5.26 (m, 1 H, —CONH—); 4.30 (m, 1 H, —CH—); 3.4-3.8 (m, 12 H, —CH$_2$O—; 3.03-3.4 (m, 4 H, —CH$_2$—NH—, —CH$_2$—NH$_2$); 2.78-3.02(m, 2 H, —CH$_2$—); 2.0 (m, 2 H, —CH$_2$—); 1.7 (m, 2 H, —CH$_2$—); 1.39 (s, 9 H, —O—C(CH$_3$)$_3$); 1.0 (d, 18 H, Si—C(CH$_3$)$_3$); 0.2 (d, 12 H, Si—C(CH$_3$)$_2$).

Example 37

Synthesis of N-(13-(N'-t-Butyloxycarbonyl-L-Amino-3',4'-bis(t-butyldimethylsilyloxy)-4,7,10-trioxatridecanyl)-methacrylamide 0.57 g (0.79 mmol) of N-(13'-Amino-4',7',10'-trioxatridecanyl)-t-butyloxycarbonyl-3',4'-bis(t-butyldimethylsilyloxy)-L-phenylalanamide and 0.166 ml (1.18 mmol) of Et$_3$N were dissolved in 5 ml of anhydrous chloroform, to which 0.176 ml (1.18 mmol) of methacrylic anhydride was added. The solution was stirred at room temperature for 3 hours, then solvent was removed in vacuo. Pure 6 was obtained by column chromatography (silica gel; eluent: ethyl acetate) as a white, sticky solid with a yield of 61%. $^1$H NMR (500 MHz, CDCl$_3$); ÿ 6.60-6.80 (3 H, C$_6$H$_3$(O—Si—)$_2$—); 6.40 (m, 1 H, —CONH—); 5.71 s (1H, CHH=); 5.30 s (1H, CHH=); 5.096 (m, 1 H, —CONH—); 4.21 (m, 1 H, —CH—); 3.2-3.65 (m, 16 H, —CH$_2$O, —CH$_2$—NH—CH$_2$—NH$_2$); 2.80-2.99 (m, 2 H, —CH$_2$—); 1.96 s (3 H, —CH$_3$); 1.81 (m, 2 H, —CH$_2$—); 1.68 (m, 2 H, —CH$_2$—); 1.40 (s, 9 H, —O—C(CH$_3$)$_3$); 1.0 (d, 18 H, Si—C(CH$_3$)$_3$); 0.2 (d, 12 H, Si—C(CH$_3$)$_2$).

Example 38

Synthesis of N-(13-(N'-t-Boc-L-3',4'dihydroxylphenylalaninamido)-4,7,10-trioxatridecanyl)-methacrylamide To a 10 ml round bottom flash were added 0.344 g (0.433 mmol) of N-(13-(N'-t-Butyloxycarbonyl-L-Amino-3',4'-bis(t-butyldimethylsilyloxy)-4,7,10-trioxatridecanyl)-methacrylamide, 3 mL of THF, and 0.137 g (0.433 mmol) of TBAF. The solution was stirred at room temperature for 5 minutes, then 3 ml of 0.1 N HCl was added. The solution was extracted three times with DCM, after which the solvent was evaporated in vacuum. 7 was obtained as a white solid by column chromatography (silica gel; eluent: 7% methanol in DCM) with a yield of 63%. $^1$H NMR (500 MHz, acetone-d$_6$); ÿ 7.90 (m, 1 H, —CONH—); 7.23-7.40 (d 2 H, C$_6$H$_2$(OH)$_2$—); 6.56-6.76 (3 H, C$_6$H$_2$(OH)$_2$—; 5.930 (m, 1 H, —CONH—); 5.71 s (1H, CHH=); 5.30 s (1H, CHH=); 4.20 (m, 1 H, —CH—); 3.1-3.60 (m, 16 H, —CH$_2$O, —CH$_2$—NH—, —CH$_2$—NH$_2$); 2.70-2.95 (m, 2H, —CH$_2$—); 1.96 s (3 H, —CH$_3$); 1.78 (m, 2 H, —CH$_2$—); 1.65 (m, 2 H, —CH$_2$—); 1.39 (s, 9 H, —O—C(CH$_3$)$_3$).

Example 39

Synthesis of PEG-Diacrylate (PEG-DA)

40 g (5 mmol) of PEG was dried by azeotropic evaporation in benzene and then dissolved in 150 mL of DCM. 4.18 mL (30 mmol) of Et$_3$N and 3.6 mL (40 mmol) of acryloyl chloride was added to the polymer solution. The mixture was refluxed with stirring for 5 hours and allowed to cool at room temperature overnight. Ether was added to the mixture to form a faint yellow precipitate. The crude product was then dissolved in saturated NaCl solution, which was heated to 60° C. to form two layers. DCM was added to the top layer and MgSO$_4$ was added to remove moisture. After filtration of MgSO$_4$, the volume of the solvent was reduced in vacuum and the sample was precipitated in ether. The final product was dried in vacuum and stored at −15° C. The yield was 75%. $^1$H NMR (500 MHz, D$_2$O): δ 6.47 (d, 1 H, CHH=C—); 6.23 (m, 1 H, C=CH—C(=O)—O—); 6.02 (d, 1H, CHH=C—); 4.35 (m, 2 H, —CH$_2$—O—C(=O)—C=C); 3.23-3.86 (PEG CH$_2$)

Example 40

Photopolymerization of PEG-DA

Precursor solutions of PEG-DA, 1, 7, and photoinitiator were prepared and mixed immediately before photopolymerization. Stock solutions of PEG-DA (200 mg/mL) and 1 (40 mg/mL) were dissolved in N$_2$-purged phosphate buffered saline (PBS, pH 7.4), where 7 (60 mg/mL) was dissolved in 50:50 PBS/95% ethanol previously purged with N$_2$. To prepare the final polymerization mixture, solutions of 1 or 7 were combined with PEG-DA to achieve a final concentration of PEG-DA and DHPD derivatives of 150 mg/mL. 100 µL of mixture was then added to a disc-shaped mold (100 µL, diameter=9 mm, depth=2.3 mm, Secure Seal® SA8R-2.0, Grace Bio Lab, Inc., OR) and irradiated for up to 20 minutes either with an UV lamp (Black Ray® Lamp, 365 nm, Model UVL-56, UVP, CA) or a blue light lamp (VIP®, 400-500 nm, BISCO Inc., IL). For UV initiated photocuring, DMPA (600 mg/mL in VP) was added to the polymeric solution to make a final concentration of 34 mM. Visible light-induced curing was performed using either CQ (100 mg/mL in VP, final concentration=150 mM) with DMAB (30 mg/mL in VP, final concentration=151 mM), or FNa$_2$ (188 mg/mL in PBS, final concentration=2 mM) with AA (100 mg/mL in PBS, final concentration=17 mM) as the photoinitiator. The final VP concentration was adjusted to be between 135 and 300 mM.

After irradiation, the gels were blotted with filter paper to remove the liquid surface layer and weighed. Percent gel conversion was then determined by dividing the weight of the gel by the weight of 100 µL of the precursor solution.

Example 41

Determining DOPA Incorporation

The amount of DOPA incorporated into the photopolymerized gel was determined using a modification of the colorimetric DOPA assay developed by Waite and Benedict. Photocross-linked gels were stirred in 3 mL of 0.5 N HCl to extract DOPA monomers that were not incorporated into the gel network. 0.9 mL of the nitrite reagent (1.45 M sodium nitrite and 0.41 M sodium molybdate dihydrate) and 1.2 mL of 1M NaOH were added to 0.9 mL of the extraction solution, and the absorbance (500 nm) of the mixture were recorded using a Hitachi U-2010 UV-Vis spectrophotometer with 2 to 4 minutes of NaOH addition. Standard curves were constructed using known 1 to 7 concentrations.

Example 42

Mechanical Test

Hydrogels were formed in the shape of a hemisphere by loading 25 µL of the polymer mixture onto a glass slide treated with 1H, 1H,2H,2H-perfluorooctyltrichlorosilane. Gels were irradiated for 10 minutes, dialyzed in 0.15 M HCl for at least 24 hours to extract unincorporated DOPA monomers, and then equilibrated in PBS for greater than 15 minutes prior to testing. To determine the gel modulus, hemispherical gel caps were attached to one end of a steel cylinder (diameter=6 mm, length=30 mm) using superglue. The other end of the cylinder was attached to a piezoelectric stepping motor (IW-701-00, Burleigh Instruments, N.Y.) aligned in series with a 50 g load transducer (FTD-G-50, Schaevitz Sensors, Va.) with a resolution of approximately 0.1 mN. A fiber optic displacement sensor (RC100-GM2OV, Philtec, Inc., MD) measured the axial movement of the steel rod. A TiO$_2$-coated Si wafer was positioned below the hydrogel, and the TiO$_2$ surface was flooded with PBS in order to maintain the hydration of the gel. The indenter was advanced at 5 µm/s until a maximum compressive load of 4 mN was measured.

Elastic moduli were calculated by assuming Hertzian mechanics for the specific case of non-adhesive contact between an incompressible elastic hemisphere and a rigid plane, in which case the Hertzian relationship between load ($P_h$) and displacement ($\delta_h$) becomes:

$$P_h = \frac{16R^{1/2}E}{9}\delta_h^{3/2} \qquad (1)$$

where R and E are the radius of curvature and the elastic modulus of the hemispherical gel, respectively. The radius of curvature of the gels was determined from height and width measurements obtained from a photograph of the gel.

Example 43

Chemical Oxidation of PEG-DOPA Into a Hydrogel 4-arm-PEG-amine (PEG-(NH$_2$)$_4$, $\overline{M}_n$=10,000) was purchased from SunBio, Inc. (Walnut Creek, CAv) while linear PEG-bis-amine (PEG-(NH$_2$)$_2$, $\overline{M}_w$=3,400) and methoxy-PEG-amine (mPEG-NH$_2$, $\overline{M}_w$=5,000) were purchased from Shearwater Polymers, Inc. (Huntsville, Ala.). Sephadex® LH-20 was obtained from Fluka (Milwaukee, Wis.). N-Boc-L-DOPA dicyclohexylammonium salt, sodium periodate (NaIO$_4$), mushroom tyrosinase (MT, EC 1.14.18.1), and horseradish peroxidase (HRP, EC 1.11.1.17) were acquired from Sigma Chemical Company (St. Louis, Mo.). Triethylamine (Et$_3$N), hydrogen peroxide (30 wt %, H$_2$O$_2$), sodium molybdate dihydrate, and sodium nitrite were purchased from Aldrich Chemical Company (Milwaukee, Wis.). L-Dopa was purchased from Lancaster (Windham, N.H.). 1-Hydroxybenzotriazole (HOBt) was obtained from Novabiochem Corp. (La Jolla, Calif.) and O-(Benzotriazol-1-yl)-N,N,N',N'-tetramethyluronium hexafluorophosphate (HBTU) was acquired from Advanced ChemTech (Louisville, Ky.).

Synthesis of DOPA-Modified PEG

Linear and branched DOPA-modified PEG's containing up to four DOPA endgroups were synthesized using standard carbodiimide coupling chemistry as described below. The structure of the four DOPA-modified PEG's are shown in FIG. 1.

Synthesis of PEG-(N-Boc-DOPA)$_4$, I. PEG-(NH$_2$)$_4$ (6.0 g, 0.60 mmoles) was reacted with N-Boc-L-DOPA dicyclohexylammonium salt (4.8 mmoles), HOBt (8.0 mmoles), and Et$_3$N (8.0 mmoles) in 60 mL of a 50:50 mixture of dichloromethane (DCM) and dimethylformamide (DMF). HBTU (4.8 mmoles) in 30 mL of DCM was then added and the coupling reaction was carried out under argon at room temperature for one hour. The solution was successively washed with saturated sodium chloride solution, 5% NaHCO$_3$, diluted HCl solution, and distilled water. The crude product was concentrated under reduced pressure and purified by column chromatography on Sephadex® LH-20 with methanol as the mobile phase. The product was further purified by precipitation in cold methanol three times, dried in vacuum at room temperature, and stored under nitrogen at −20° C. $^1$H NMR (500 MHz, CDCl$_3$/TMS): δ 6.81-6.77 (m, 2H, C$_6$H$_2$(OH)$_2$—), 6.6 (d, 1H, C$_6$H$_2$H(OH)$_2$—), 6.05 (br, s, 1H), 5.33 (br, s, 1H), 4.22 (br, s, 1H, C$_6$H$_3$(OH)$_2$—CH$_2$—CH(N—)—C(O)N—), 3.73-3.41 (m, PEO), 3.06 (m, 2H, PEO-CH$_2$—N—C(O)—), 2.73 (t, 2H, C$_6$H$_3$(OH)$_2$—CH$_2$—CH—), 1.44 (s, 9 H, (CH$_3$)$_3$C—). GPC-MALLS: $\overline{M}_w$=11,900, $\overline{M}_w$/$\overline{M}_n$=1.01.

Synthesis of PEG-(DOPA)$_4$, II. 3.0 g of I (0.25 mmoles) was dissolved in 15 mL of DCM at room temperature. 15 mL of TFA was added to the mixture to react for 30 minutes under argon. After evaporating the solvent in a rotary evaporator, the product was precipitated with cold methanol three times, dried in vacuum at room temperature, and stored under nitrogen at −20° C. $^1$H NMR (500 MHz, D$_2$O): δ 6.79 (d, 1H, C$_6$H$_2$H(OH)$_2$—), 6.66 (s, 1H, C$_6$H$_2$H(OH)$_2$—), 6.59 (d, 1H, C$_6$H$_2$H(OH)$_2$—), 4.00 (t, 1H, C$_6$H$_3$(OH)$_2$—CH$_2$—CH(N—)—C(O)N—), 3.70-3.34 (M, PEO), 3.24 (m, 2H, PEG-CH$_2$—N—C(O)—), 3.01-2.88 (m, 2H, C$_6$H$_3$(OH)$_2$—CH2—CH(N—)—C(O)N—). GPC-MALLS: $\overline{M}_w$=11,400, $\overline{M}_w/\overline{M}_n$=1.02.

Synthesis of PEG-(N-Boc-DOPA)$_2$, III. PEG-(NH$_2$)$_2$ (5.0 g, 1.5 mmoles), N-Boc-L-DOPA dicyclohexylammonium salt (5.9 mmoles), HOBt (9.8 mmoles), and Et$_3$N (9.8 mmoles) were dissolved in 50 mL of a 50:50 mixture of DCM and DMF. HBTU (5.9 mmoles) in 25 mL of DCM was then added, and the reaction was carried out under argon at room temperature for 30 minutes. Recovery and purification of the product was performed as described above for I. $^1$H NMR (500 MHz, CDCl$_3$/TMS): δ 6.81-6.77 (m, 2H, C$_6$H$_2$(OH)$_2$—), 6.59 (d, 1H, C$_6$H$_2$H(OH)$_2$—), 6.05 (br, s, 1H), 5.33 (br, s, 1H), 4.22 (br, s, 1H, C$_6$H$_3$(OH)$_2$—CH$_2$—CH(N—)—C(O)N—), 3.73-3.42 (M, PEO), 3.06 (m, 2H, PEO-CH$_2$—N—C(O)—), 2.74 (t, 2H, C$_6$H$_3$(OH)$_2$—CH$_2$—CH(N—)—C(O)N—), 1.44 (s, 9 H, (CH$_3$)$_3$CO—). GPC-MALLS: $\overline{M}_w$=4,600, $\overline{M}_w/\overline{M}_n$=1.02.

Synthesis of methoxy-PEG-(N-Boc-DOPA), IV. mPEG-NH$_2$ (2.0 g, 0.40 mmoles), N-Boc-L-DOPA dicyclohexylammonium salt (0.80 mmoles), HOBt (1.3 mmoles), and Et$_3$N (1.3 mmoles) were dissolved in 20 mL of a 50:50 mixture of DCM and DMF. HBTU (0.80 mmoles) in 10 mL of DCM was then added, and the reaction was carried out under argon at room temperature for 30 minutes. Recovery and purification of the product was performed as described above for I. $^1$H NMR (500 MHz, CDCl$_3$/TMS): δ 6.81-6.60 (m, 3H, C$_6$H$_3$(OH)$_2$—), 6.01 (br, s, 1H, OH—), 5.32 (br, s, 1H, OH—), 4.22 (br, s, 1H, C$_6$H$_3$(OH)$_2$—CH$_2$—CH(N—)—C(O)N—), 3.73-3.38 (m, PEO), 3.07 (m, 2H, PEO-CH$_2$—NH—C(O)—), 2.73 (t, 2H, C$_6$H$_3$(OH)$_2$—CH$_2$—CH(N—)—C(O)N—), 1.44 (s, 9 H, (CH$_3$)$_3$C—), 1.25 (s, 3 H, CH$_3$CH$_2$O—). GPC-MALLS: $\overline{M}_w$=6,100, $\overline{M}_w/\overline{M}_n$=1.02.

DOPA Content Determination

The DOPA content of the DOPA-modified PEGs was determined by integration of relevant peaks in the $^1$H NMR spectrum, and by a colorimetric DOPA assay. In the NMR method, the DOPA content was measured by comparing the integral value of Boc methyl protons at δ=1.44 to the PEG methylene protons at δ=3.73-3.38. The DOPA assay was based on the previously described method of Waite and Benedict. Briefly, PEG-DOPA aqueous solutions were treated with nitrite reagent (1.45 M sodium nitrite and 0.41 M sodium molybdate dihydrate) followed by the addition of excess NaOH solution. The absorbance (500 nm) of the mixture was recorded using a Hitachi U-2010 UV/vis spectrophotometer, within 2 to 4 minutes of NaOH addition. A standard curve was constructed using solutions of known DOPA concentration.

Formation of PEG-DOPA Hydrogels

To form PEG-DOPA hydrogels, sodium periodate (NaIO$_4$), horseradish peroxidase and hydrogen peroxide (HRP/H$_2$O$_2$), or mushroom tyrosinase and oxygen (MT/O$_2$) were added to solutions of PEG-DOPA (200 mg/mL) in phosphate buffered saline (PBS, pH 7.4). For gelation induced by MT, the PBS was sparged with air for 20 minutes prior to adding MT. Gelation time was qualitatively determined to be when the mixture ceased flowing, as measured by inversion of a vial containing the fluid.

Oscillatory Rheometry

Oscillatory rheometry was used to monitor the process of gelation and to determine the mechanic properties of the hydrogels. Cross-linking reagent was added to aqueous solution of PEG-DOPA and the well-mixed solution was loaded onto a Bohlin VOR rheometer. The analysis was performed at a frequency of 0.1 Hz, a strain of 1%, and a 30 mm diameter cone and plate fixture with a cone angle of 2.5°.

Spectroscopic Evaluation of DOPA Oxidation

DOPA-modified PEG was dissolved in 10 mM PBS solution (bubbled with argon for HRP/H$_2$O$_2$ and NaIO$_4$ or air for MT experiments). After adding the oxidizing reagent, the time-dependent UV/vis spectra of the solution were monitored at wavelengths from 200 to 700 nm at a scan rate of 800 nm/min. All samples were initially blanked against PBS buffer and recorded at room temperature using a Hitachi U-2010 UV/vis spectrophotometer.

Molecular Weight Analysis

Molecular weights were determined by GPC-MALLS on a DAWN EOS (Wyatt Technology) using Shodex-OH Pak columns in an aqueous mobile phase (50 mM PBS, 0.1 M NaCl, 0.05% NaN$_3$; pH=6.0) and a Optilab DSP (Wyatt Technology) refractive index detector.

For molecular weight calculations, the experimentally determined dn/dc value of IV (0.136) was used.

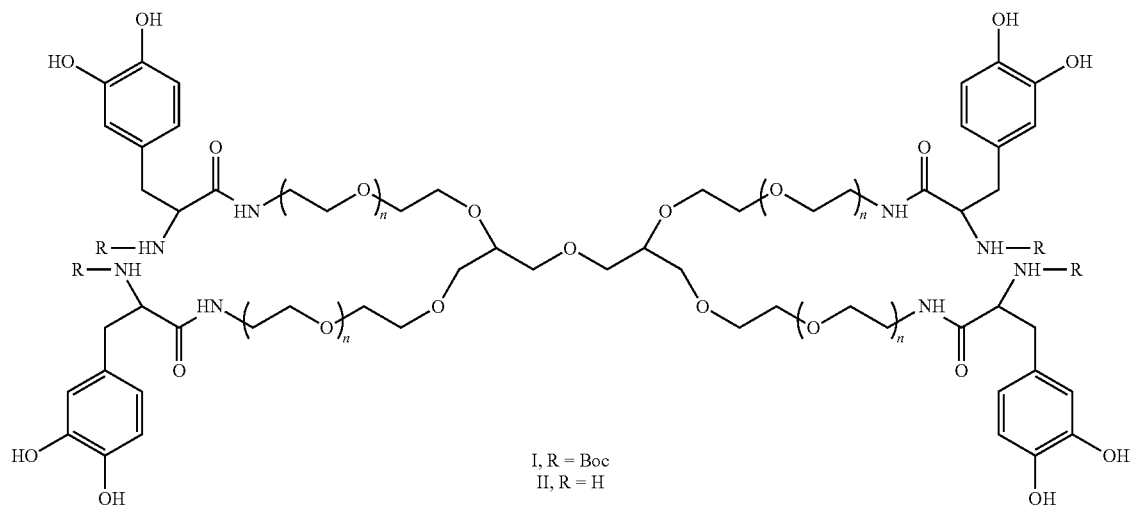

I, R = Boc
II, R = H

-continued

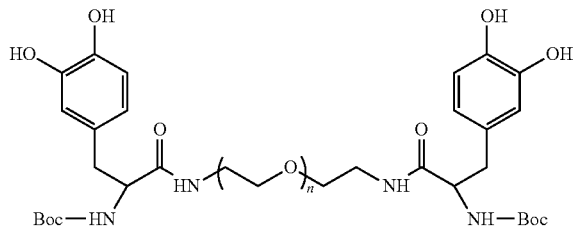

III

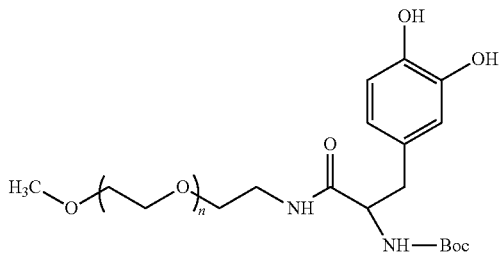

IV

Example 44

Materials and Methods

Tip Modification

Before the surface modification of silicon nitride (Si3N4) tips, cleaning procedures were performed using O2 plasma (name of a machine) for 3 min and subsequently they were transferred to a piranha solution (sulfuric acid:H2O2=8:2) for 30 min. They moved to 20% (v/v) 3-aminopropyltrimethoxysilane in toluene to be functionalized with amines for 30 to 60 min after rinsing with H2O. Two polyethylene glycol (PEG) derivatives were chosen for PEGylation on the AFM tips: mPEG-N-hydroxy succinimide (NHS) (Mw 2000) and Fmoc-PEG-NHS (Mw 3400) (Nektar Inc.). Mixture (Fmoc-PEG-NHS:mPEGNHS=1:5-10, 5 mM) of PEGs were prepared in 50 mM sodium phosphate buffer, 0.6 M K2SO4, pH 7.8 and chloroform. PEGylation reactions were conducted sequentially first in a sodium phosphate buffer at 40° C. and subsequently in chloroform for 3 hrs in each step. The reason to use PEG mixture is to prevent multiple DOPA binding on TiO2. Fmoc-PEG-NHS provides an amine for Boc-DOPA conjugation after Fmoc cleavage. Piperidine (20% v/v in NMP) was used to deprotect Fmoc for 5 min and subsequently cantilevers were transferred to BOP/HOBt/DOPA (a molar ratio of 1:1:1, final 8 mM in NMP) solution with 10 μL DIPEA. The same procedure was used for Tyrosine modification.

AFM Experiment

All data were collected in AFM instrument (Asylum Research, Santa Barbara, Calif.) on top of an inverted Nikon microscope. The spring constant (around 45, 100, and 300 pN/nm by manufacture's information) of an individual cantilever was calibrated by applying the equipartition theorem to the thermal noise spectrum (S1). A drop of water was applied to a pre-cleaned (sonication in organic solvent and O2 plasma) TiO2 surface. Force-distance curves containing PEG elasticity and contour length were selected for further statistical analysis. For the DOPAquinone experiments, all experiments are done in 20 mM Tris, pH 9.8.

Dynamic Force Experiments

Loading rate dependent force measurement revealed the energy landscape of DOPA binding (17). A slope (=kBT/xb) of the linear plot (force vs. ln(loading rate)) determines the distance of energy barrier xb along the applied force axis. The binding energy barrier is calculated by the force of logarithmic intercept at zero loading rate from the force transition occurred by pulling rate change and xb from the slope. Silicon nitrite AFM cantilevers (Bio-Levers, Olympus, Japan) were used because of their small string constants (~5 pN/nm and ~28 pN/nm). The lowest loading rate of 2 nN/sec in our study was achievable using the pulling rate of 400 nm/sec and the cantilever (~5 pN/nm). The highest loading rate (1500 nN/sec) was produced by 5 μm/sec operation of piezoelectric device and the use of stiff cantilever (300 pN/nm, Veeco). Surface characterization Surfaces were analyzed by X-ray photoelectron microscopy (XPS), (Omicron, Taunusstein Germany) equipped with a nomochromated Al Kα (1486.8 eV) 300 W X-ray source and an electron gun to eliminate charge build-up. Silicon nitride surfaces (0.7×0.7 cm2) prepared in the high temperature chamber (ask to Keun Ho) were cleaned and modified as the same procedures described in AFM tip modification. The photoelectron signal from carbon 1s orbital was the major indicator for surface modification considering all abundant species of Si, O, and N in Si3N4 surfaces.

With respect to examples 45-46, Ultrapure water (resistivity=18.2 MΩ, pH=6.82) used in all experiments was obtained from a NANOpure Infinity® system from Barnstead/Thermolyne Corporation (Dubuque, Iowa). OEGMEMA monomers (Aldrich) were passed through an activated basic alumina (Aldrich) column to remove the inhibitor. Other reagents for initiator synthesis and polymerization were purchased from commercial sources and used without further purification.

Example 45

ATRP Initiator Synthesis

The synthesis of a representative catechol-terminated ATRP initiator is shown in Scheme 4. A 250 mL round-bottomed flask was charged with 120 mL of 0.1 M borate buffer, and the solution was degassed with Ar for 30 min. Dopamine HCl (2.28 g, 12.0 mmol) was added. The reaction mixture was stirred for 15 min and the pH was sadjusted to 9-10 with Na$_2$CO$_3$ (3.99 g, 32 mmol). The resulting solution was cooled in an ice bath. Bromoaceopropionate (2.59 g, 12.0 mmol) was added dropwise via a syringe, and the mixture was stirred for 24 hours under Ar, maintaing a pH of 9-10. The solution was then acidified to pH=2 with 6 M aqueous HCl, extracted with EtOAc three times, dried (MgSO$_4$), filtered, and concentrated by a rotary evaporator. The crude product was purified by silica gel column chromaorgraphy (4% MeOH in CHCl$_3$) to give colorless viscous liquid that was further purified by crystallization from MeOH/H$_2$O to afford white crystals: 1.20 g, 34.7%. $^1$H NMR (in CDCl$_3$, δ in ppm): 6.51-6.69 (3H, m), 4.40 (1H, q, 7 Hz), 3.31-3.39 (2H, m), 2.61-2.66 (2H, m), 1.71 (3H, d, 7 Hz). $^{13}$C NMR (in CDCl$_3$, δ in ppm): 172.45, 146.35, 144.92, 131.88, 121.25, 117.03, 116.48, 44.16, 42.75, 35.68, 22.59.

Scheme 4. Synthetic Scheme and Structure of the Catechol-terminated ATRP Initiator.

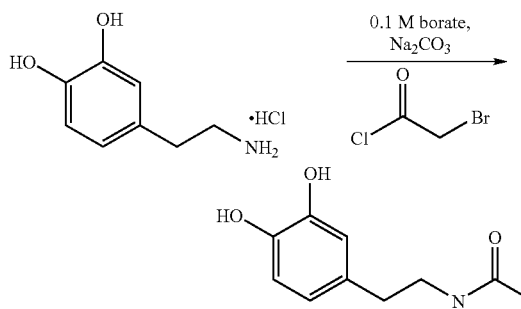

Substrate preparation. Si-wafer (MEMC Electronic Materials, St. Peters, Mo., surface orientation (100)) were coated with 100 nm Ti by an Edwards FL400 electron beam evaporator at $<10^{-6}$ Torr. The wafer was then cut into 8 mm×8 mm (or, alternatively 1 cm×2 cm) pieces which were subsequently cleaned by ultrasonication in the following media: 5% Contrad70 (Fisher), ultrapure water, acetone, and petroleum ether. The substrates were further cleaned in an oxygen plasma chamber (Harrick Scientific) at <200 mTorr and 100 W for 3 min.

Initiator Immobilization

Freshly cleaned Ti/TiOx surfaces were immersed in 1 mg/mL initiator aqueous solution at room temperature. The adsorption process was held for 12 hours in the dark. The substrates were rinsed with copious ultrapure water to remove unattached initiator and dried with nitrogen flow. Without limitation, it is believed a native titanium oxide forms spontaneously, hence reference to this non-limiting substrate as $Ti/TiO_x$.

Surface-initiated Polymerization

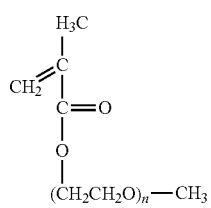

Structure of OEGMEMA monomer n = 4,
Mn ~ 300

The monomer used in this example was oligo(ethylene glycol) methyl ether methacrylate (OEGMEMA, Mn~300), which was first passed through a basic alumina gel column to remove the inhibitor. As would be understood in the art, other monomers can be utilized; e.g., varying by length of alkene oxide side chain and/or side chain termnination. Here, without limitation, n can range from about 4 to about 9. The modified substrates were placed in a 3-neck flask under Ar flow. 2 mL OEGMEMA monomer (7 mmol), 2 mL ultrapure water, 1.45 uL N,N,N',N',N"-Pentamethyldiethylenetriamine (PMDETA, 7 μmol), and 1 mg CuBr (7 μmol) were charged into another flask and purged with Ar flow for 1 hour. This solution was then injected into the flask that contained substrates via a degassed syringe. The polymerizations were performed at room temperature under Ar protection with stirring from a magnetic stirrer. The mixture remained light blue and stable throughout the reaction. At various times, the substrates were taken out of the polymerization solution and washed with copious ultrapure water, followed by drying with nitrogen flow. The polymer-grafted samples were further dried under vacuum overnight before further analysis. Inhibitor immobilization and polymerization are illustrated in scheme 5, below.

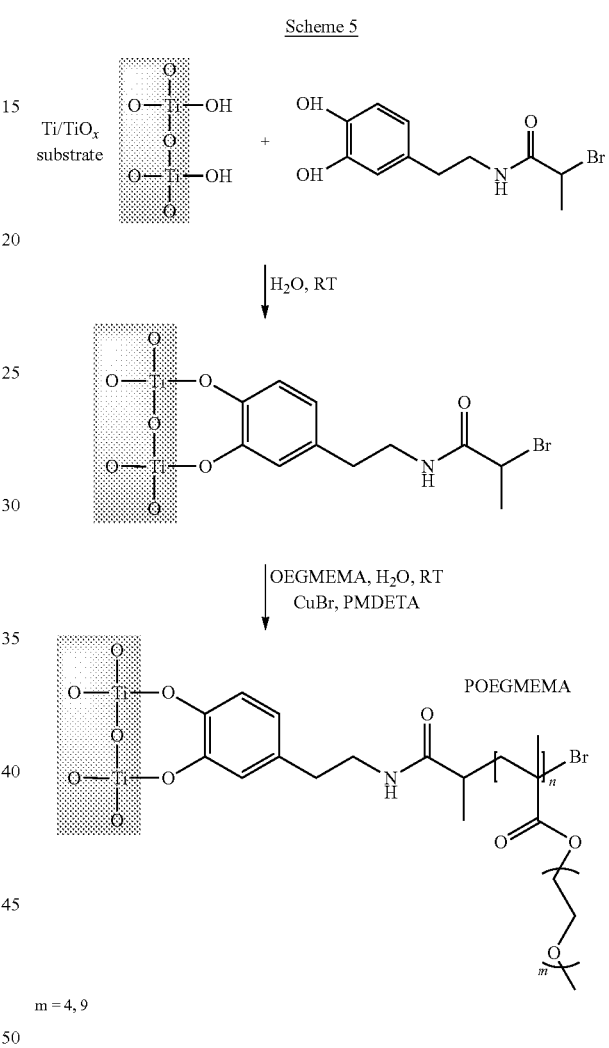

Scheme 5 m = 4, 9

Polarization-modulation Infrared Reflection-adsorption Spectroscopy (PM-IRRAS)

PM-IRRAS measurements were performed on a Thermo Nicolet NEXUS 870 Fourier transform infrared spectrometer equipped with a tablet optics module (TOM) and a mercury-cadmium-tellurium (CAT) detector. With unmodified 100 nm Ti substrates as the reference, spectra of polymer-grafted samples were obtained from 1024 scans at a resolution of 4 $cm^{-1}$, 80° beam incidence angle, and 50 kHz modulation frequency.

Changes in surface composition after SI-ATRP were confirmed by contact angle and PM-IRRAS measurements. $O_2$ plasma cleaned substrates showed highly hydrophilic nature with a water contact angle of less than 10°. It increased to an average value of 58° after the modification by the initiator layer. This angle decreased to around 50°, indicating the increase in the hydrophilicity for the grafted POEGMEMA layer.

Figure 37:
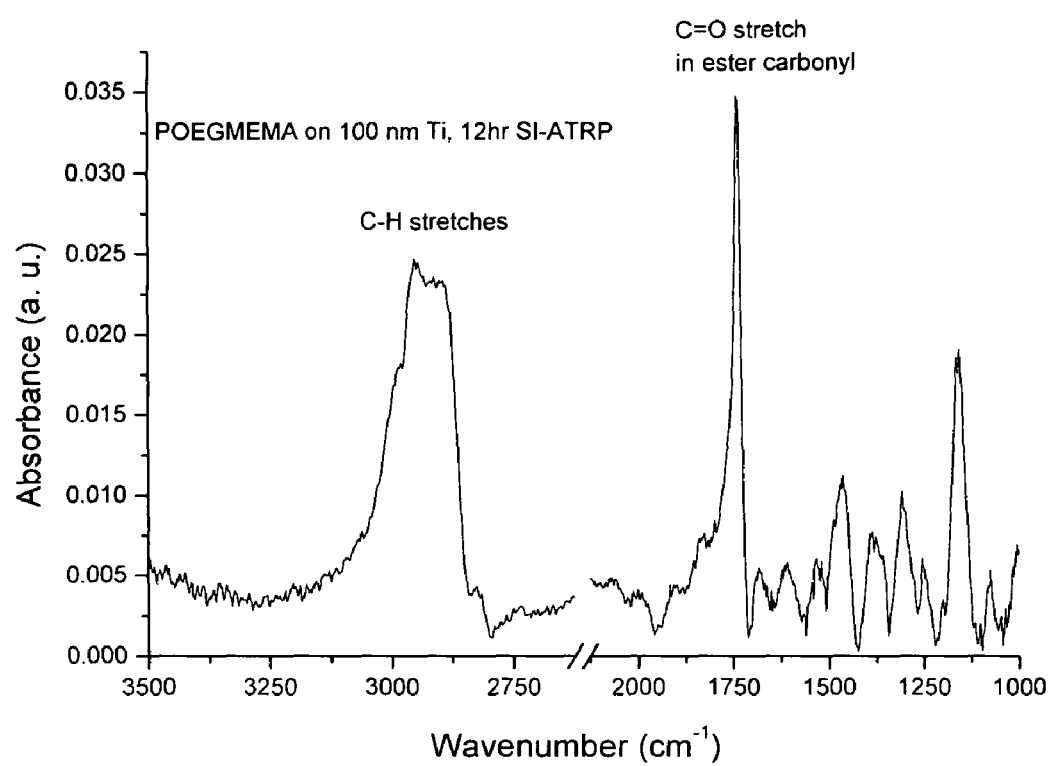
FIG. 37 plots the PM-IRRAS spectrum of the grafted POEGMEMA layer.

A PM-IRRAS spectrum of the grafted POEGMEMA layer is shown in FIG. 37. (Bands associated with the polymer backbone are assigned as follows.) Typical features of the methyl methacrylate polymer include strong absorptions at 2850-2990 cm$^{-1}$ due to C—H symmetric and asymmetric stretching, a sharp peak at 1738 cm$^{-1}$ from C=O stretch in the ester group, and peaks at 1360-1470 cm$^{-1}$ from $CH_2$ and $CH_3$ deformation. Other features associated with the OEG side chain include bands at 1070-1260 cm$^{-1}$ from C—O—C stretches in both the ether and ester groups and a small peak at 2825 cm$^{-1}$ due to C—H stretch in the methyl ether end group. Moreover, the absence of an absorption from the vinyl group (at 1640 cm$^{-1}$ on the spectrum of the monomer, not shown in the figure.) further confirmed the occurrence of SI-ATRP.

X-ray Photoelectron Spectroscopy (XPS)

Figure 38:
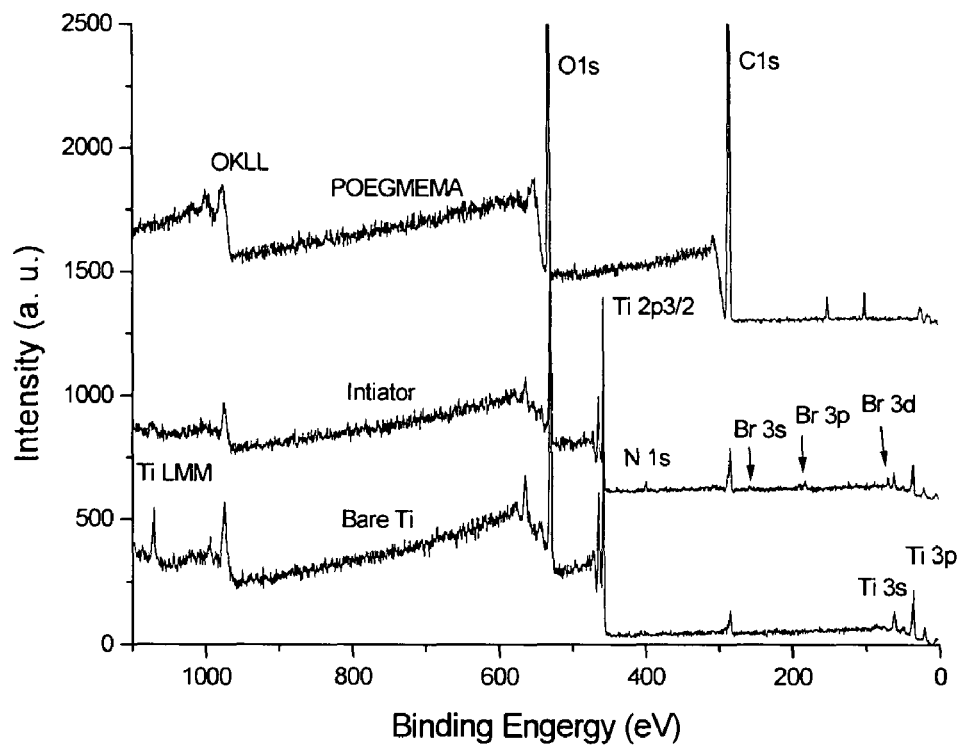
FIG. 38 has two plots the XPS spectra of the grafted POEGMEMA layer on $TiO_2$ (Binding Energy vs. Intensity).
Figure 38:
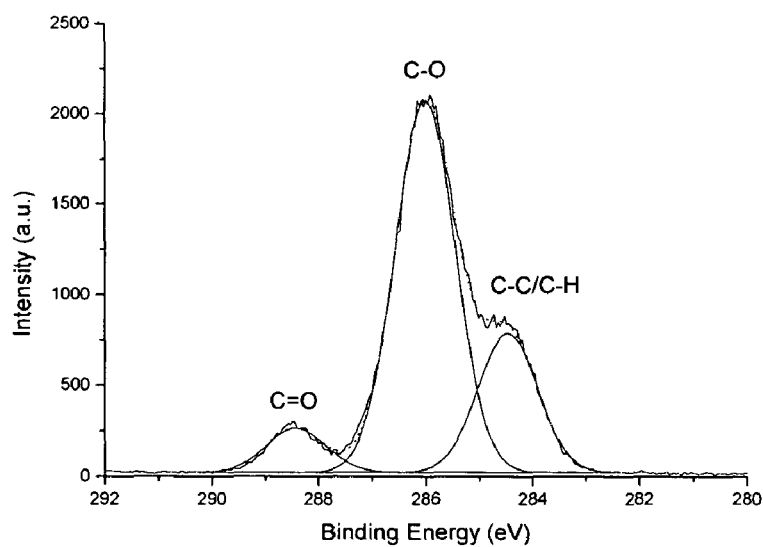

XPS data were collected on an Omicron ESCALAB (Omicron, Taunusstein, Germany) configured with a monochromated Al Kα (1486.8 eV) 300-W X-ray source, 1.5 mm circular spot size, a flood gun to counter charging effects, and an ultrahigh vacuum (<10$^{-8}$ Torr). The takeoff angle, defined as the angle between the substrate normal and the detector, was fixed at 45°. Substrates were mounted on standard sample studs by means of double-sided adhesive tapes. All binding energies were calibrated using C(1s) carbon peak (284.6 eV). Analysis consisted of a broad survey scan (50.0 eV pass energy) and a 10-min high-resolution scan (22.0 eV pass energy) at 270-300 eV for C(1s). Two spectra are shown in FIG. 38.

Example 46

Cell Culture

T3-Swiss albino fibroblasts obtained from ATCC (Manassas, Va.) were maintained at 37° C. and 10% $CO_2$ in Dulbecco's modified Eagle's medium (DMEM; Cellgro, Herndon, Va.) containing 10% fetal bovine serum (FBS) and 100 µg/mL of penicillin and 100 U/mL of streptomycin. Immediately before use, fibroblasts of passage 12-16 were harvested using 0.25% trypsin-EDTA, resuspended in DMEM with 10% FBS, and counted using a hemocytometer.

Quantification of Cell Adhesion

Figure 39:
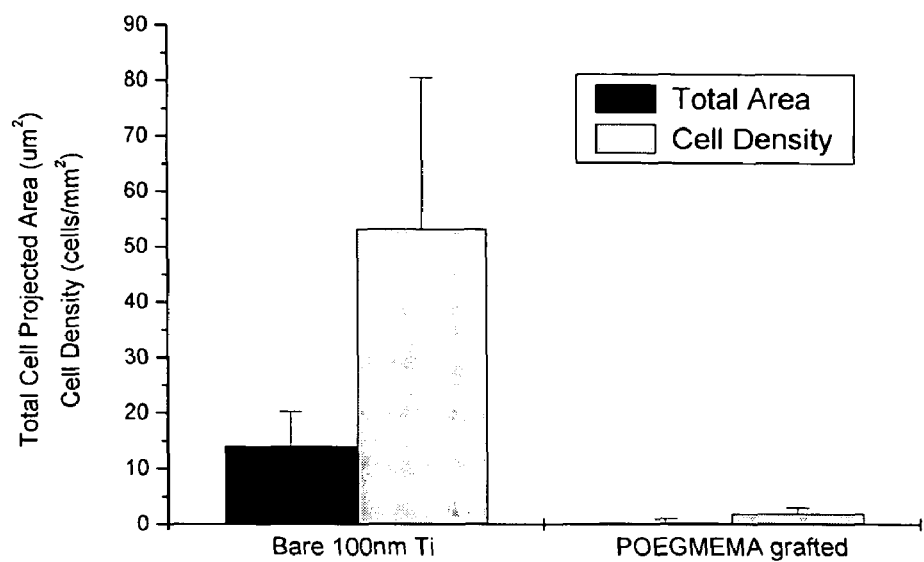
FIG. 39 shows the cell attachment to unmodified $TiO_2$ and grafted POEGMEMA layer on $TiO_2$.
Figure 40:
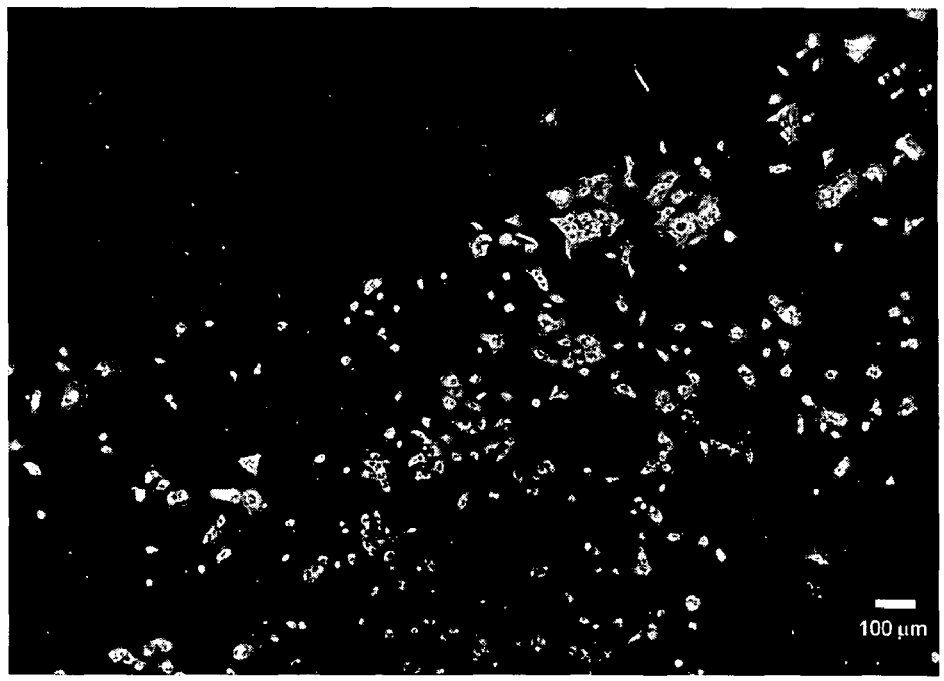
FIG. 40 shows the fluorescence microscopy image of fibroblast cell attachment (4 hour) on a Ti substrate modified in the upper left corner by SI-ATRP of OEGMEMA (100-nm).

Substrates were pretreated in 12-well TCPS plates with 1.0 mL of DMEM containing FBS for 30 min at 37° C. and 10% $CO_2$. Cells were seeded onto the substrates at a concentration of 10×10$^3$ cells/mL and maintained for 4 hours in DMEM with 10% FBS at 37° C. and 10% $CO_2$. Nonadherent cells were removed by aspirating the medium in each well. Adherent cells were fixed in 3.7% paraformaldehyde for 5 min and subsequently stained with 5 µM 1,1'-dioctadecyl-3,3,3',3'-tetramethylindocarbocyanine perchlorate (DiI; Molecular Probes, Eugene, Oreg.) in DMSO for 45 min. Quantitative cell attachment data were obtained by acquiring 9 images from random locations on each sample using an Olympus BX-40 ($\lambda_{Ex}$=549 nm, $\lambda_{Em}$=565 nm) and a Coolsnap CCD camera (Roper Scientific, Trenton, N.J.). The resulting images were quantified using threshholding in Metamorph (Universal Imaging, Downington, Pa.). Cell attachment is shown in FIGS. 39 and 40.

It should be pointed out that control experiments performed in the absence of initiator indicated that the polymer layer was not found on unmodified, bare Ti substrates, which were treated with the same SI-ATRP procedures except the initiator immobilization step. Therefore, the POEGMEMA polymer were indeed grafted from our biomimetic initiator layer. This conclusion is further supported by a partially modified sample after the cell adhesion experiment as shown in FIG. 40. This sample was prepared by only submerging part (upper left) of a Ti substrate in the initiator solution while leaving the other part (lower right) unmodified in the air, followed by the subsequent SI-ATRP and cell adhesion assay. It is clear that cells readily attached to the unmodified portion of the substrate, but not the area modified by the grafted POEGMEMA. Thus the nonfouling advantage is an exclusive result from our SI-ATRP method. Moreover, we propose that our SI-ATRP method could be employed for patterning/printing applications.

What is claimed is:

1. A surface-initiated atom transfer radical polymerization (ATRP) method of surface modification comprising the steps:
    a) providing a surface;
    b) applying a polymerization initiator to the surface, wherein the polymerization initiator comprises:

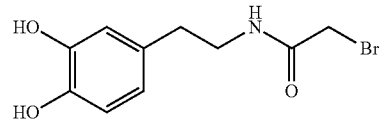

wherein the polymerization initiator is substantially immobilized to the surface after application;
    c) reacting a monomer comprising

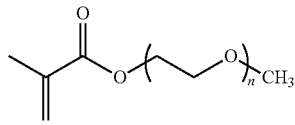

wherein n is 4 or 9,
with the surface immobilized polymerization initiator to produce a surface-bound polymer, wherein the surface-bound polymer is a reaction product of the monomer and the surface immobilized polymerization initiator comprising:

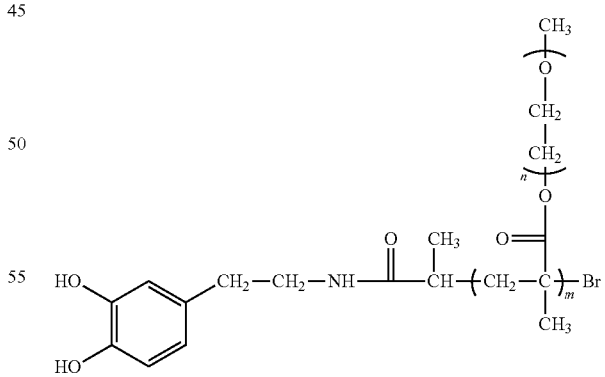

wherein m is 4 or 9.

2. A method according to claim 1 wherein the surface to be modified is titanium.

3. A method according to claim 1 wherein the surface to be modified is at least a portion of a medical device.

4. A method according to claim 1 wherein the surface to be modified is the hull of a ship.

5. A method according to claim 3 wherein the surface to be modified is at least a portion of a cardiovascular stent.

6. A method of using a catecholic compound for surface-initiated atom transfer radical polymerization, said method comprising the steps:

providing a substrate;

modifying the surface of said substrate with a medium comprising a catecholic-terminated alkyl halide comprising:

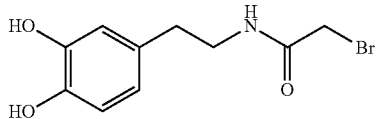

wherein the catecholic-terminated alkyl bromide is substantially immobilized to the surface after application; and reacting said modified surface comprising the immobilized catecholic-terminated alkyl halide and a monomer comprising:

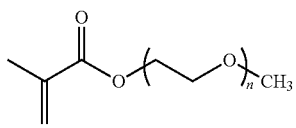

wherein n is 4 or 9, to provide a surface-bound polymer, wherein the surface-bound polymer is a reaction product of the monomer and the surface immobilized catecholic-terminated alkyl halide comprising:

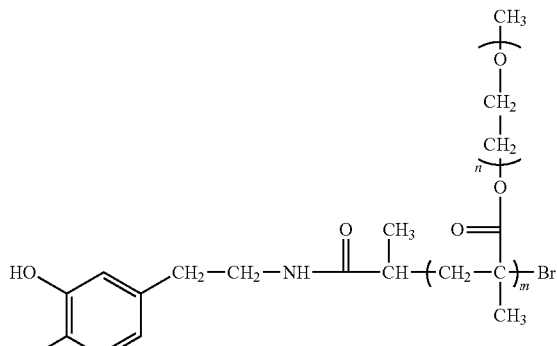

wherein m is 4 or 9.

7. The method according to claim 6 wherein said medium comprises an aqueous solution of said alkyl halide.

8. The method according to claim 6 wherein said substrate comprises titanium.

9. The method according to claim 6 wherein said substrate comprises at least a portion of a medical device.

10. The method according to claim 9 wherein said substrate comprises at least a portion of a cardiovascular stent.

11. The method according to claim 6 wherein said reaction is adjusted by at least one of monomer concentration and reaction time.

* * * * *

UNITED STATES PATENT AND TRADEMARK OFFICE
CERTIFICATE OF CORRECTION

| | | |
|---|---|---|
| PATENT NO. | : 7,858,679 B2 | |
| APPLICATION NO. | : 11/179218 | |
| DATED | : December 28, 2010 | |
| INVENTOR(S) | : Phillip B. Messersmith et al. | |

It is certified that error appears in the above-identified patent and that said Letters Patent is hereby corrected as shown below:

Column 1, lines 21-25 should be replaced with the following: --This invention was made with government support under Grant Numbers R01 DE014193, DE013030, and DE012599 awarded by the National Institutes of Health. The government has certain rights in the invention.--

Signed and Sealed this
Seventeenth Day of May, 2011

David J. Kappos
*Director of the United States Patent and Trademark Office*